United States Patent
Ismagilov et al.

(10) Patent No.: US 12,122,996 B2
(45) Date of Patent: Oct. 22, 2024

(54) DEVICE FOR ADDITIVE DELIVERY OF REAGENTS AND RELATED METHODS AND SYSTEMS

(71) Applicant: CALIFORNIA INSTITUTE OF TECHNOLOGY, Pasadena, CA (US)

(72) Inventors: Rustem F. Ismagilov, Pasadena, CA (US); Eugenia Khorosheva, Pasadena, CA (US); Dmitriy V. Zhukov, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 16/141,707

(22) Filed: Sep. 25, 2018

(65) Prior Publication Data

US 2019/0118177 A1    Apr. 25, 2019

Related U.S. Application Data

(60) Provisional application No. 62/562,684, filed on Sep. 25, 2017, provisional application No. 62/562,894, filed on Sep. 25, 2017.

(51) Int. Cl.
| | |
|---|---|
| *B01L 3/00* | (2006.01) |
| *C12N 15/10* | (2006.01) |
| *C12Q 1/6806* | (2018.01) |
| *C12Q 1/6855* | (2018.01) |
| *G01N 33/58* | (2006.01) |
| *G01N 33/68* | (2006.01) |
| *C40B 30/04* | (2006.01) |
| *C40B 40/08* | (2006.01) |
| *C40B 70/00* | (2006.01) |

(52) U.S. Cl.
CPC .... *C12N 15/1065* (2013.01); *B01L 3/502715* (2013.01); *B01L 3/502738* (2013.01); *C12Q 1/6806* (2013.01); *C12Q 1/6855* (2013.01); *G01N 33/58* (2013.01); *G01N 33/68* (2013.01); *B01L 2200/027* (2013.01); *B01L 2200/141* (2013.01); *B01L 2200/16* (2013.01); *B01L 2300/0816* (2013.01); *B01L 2300/0861* (2013.01); *B01L 2300/161* (2013.01); *B01L 2400/065* (2013.01); *C40B 30/04* (2013.01); *C40B 40/08* (2013.01); *C40B 70/00* (2013.01)

(58) Field of Classification Search
CPC .... C12N 15/1065; G01N 33/58; G01N 33/68; C12Q 1/6806; C12Q 1/6855; C12Q 2523/101; C12Q 2525/191; C12Q 2565/514; B01L 3/502738; B01L 3/502715; B01L 2300/0816; B01L 2400/065; B01L 2200/16; B01L 2300/161; B01L 2300/0861; B01L 2200/027; B01L 2200/141; C40B 30/04; C40B 40/08; C40B 70/00
See application file for complete search history.

(56) References Cited

U.S. PATENT DOCUMENTS

| | | |
|---|---|---|
| 2007/0026439 A1 | 2/2007 | Faulstich et al. |
| 2009/0021728 A1 | 1/2009 | Heinz et al. |
| 2009/0266421 A1* | 10/2009 | Linder .............. B01L 3/502746 137/1 |
| 2014/0329698 A1* | 11/2014 | Bignell ................ C12Q 1/6874 506/4 |
| 2015/0225786 A1 | 8/2015 | Litterst et al. |
| 2016/0114322 A1 | 4/2016 | Ismagilov et al. |
| 2016/0281134 A1 | 9/2016 | Wu |
| 2016/0288121 A1* | 10/2016 | Ismagilov .............. C12Q 1/703 |
| 2017/0159136 A1 | 6/2017 | Church et al. |
| 2019/0144854 A1 | 5/2019 | Ismagilov et al. |
| 2020/0263234 A1 | 8/2020 | Seelig et al. |

FOREIGN PATENT DOCUMENTS

| | | |
|---|---|---|
| WO | 91/19567 A1 | 12/1991 |
| WO | 2014/152155 A1 | 9/2014 |
| WO | 2017/034970 A1 | 3/2017 |
| WO | 2019/060914 A2 | 3/2019 |

OTHER PUBLICATIONS

Collins, D.J. et al., "The Poisson Distribution and Beyond: Methods for Microfluidic Droplet Production and Single Cell Encapsulation", Lab on a Chip, 15(17), pp. 3439-3459, (2015).
Kirchner, J.J. et al., "Interstrand Cross-Linking of Duplex DNA by Nitrous Acid: Covalent Structure of the dG-to-dG Cross-Link at the Sequence 5'-CG", Journal of the American Chemical Society, 114(11); pp. 4021-4027, (1992).
Kozlov, I.A. et al., "Efficient Strategies for the Conjugation of Oligonucleotides to Antibodies Enabling Highly Sensitive Protein Detection", Biopolymers, 73(5), pp. 621-630, (2004).
Neugebauer, J.M., "Detergents: An Overview", Methods in Enzymology, vol. 182, pp. 239-253, (1990).
Richards, F.M. et al., "Glutaraldehyde as a Protein Cross-Linking Reagent", Journal of Molecular Biology, 37(1), pp. 231-233, (1968).
Strauss, J.H. et al., "Denaturation of RNA with DimethylSulfoxide", Biopolymers, 6(6), pp. 793-807, (1968).
Yin, H. et al., "Microfluidics for Single Cell Analysis", Current Opin. Biotechnol., 23(1), pp. 110-119, (2012).

(Continued)

Primary Examiner — Christopher M Gross

(74) Attorney, Agent, or Firm — Steinfl + Bruno LLP

(57) ABSTRACT

A device for allowing compartmentalized reactions with minimized cross-contamination between the compartments, utilizing a delivery of material by loading wells to pooling wells, such that the pooling wells can be additively provided with reactants while maintaining isolation between the pooling wells. The use of geometric properties is used to facilitate transmission of fluids/droplets without the need for hydrophilic surfaces.

10 Claims, 33 Drawing Sheets

Specification includes a Sequence Listing.

(56) References Cited

OTHER PUBLICATIONS

Restriction Requirement for U.S. Appl. No. 16/141,901, filed Sep. 25, 2018 on behalf of CIT. Mail date: Dec. 17, 2019. 6 pages.
Abbyad et al., "Rails and anchors: guiding and trapping droplet microreactors in two dimensions", Lab on a Chip,2011, 11, 813-821.
Behbehani G.K. et al., "Transient partial permeabilization with saponin enables cellular barcoding prior to surface marker staining" Cytometry Part A, 2014, vol. 85, pp. 1011-1019.
Bindu, S. et al., "A Comparative Study on Permeabilization Treatments for in situDetermination of Phytase ofRhodotorula Gracilis", Letters in Applied Microbiology, 27, pp. 336-340,(1998).
Blackstock, D. et al., "Halo-Tag Mediated Self-Labeling of Fluorescent Proteins to Molecular Beacons for Nucleic Acid Detection", Chem. Commun., 50, pp. 13735-13738, (2014).
Chen, W. et al., "Reactive Oxygen Species (ROS) Inducible DNA Cross-Linking Agents and Their Effect on Cancer Cells and Normal Lymphocytes", J. Med. Chem, 57, pp. 4498-4510, (2014).
Coste, F. et al., "Crystal Structure of a Double-Stranded DNA Containing a Cisplatin Interstrand Cross-Link at 1.63 A Resolution: Hydration at the Platinated Site", Nucleic Acids Research, vol. 27, No. 8, pp. 1837-1846, (1999).
Dangla, R. et al., "Trapping Microfluidic Drops in Wells of Surface Energy", Physical Review Letters, 107, 124501, (2011), 5 pages.
Dekker, J. et al., "Capturing Chromosome Conformation", Science, vol. 295, pp. 1306-1311, (2002). 7 pages.
Dev, V.G. et al., "Nucleolus Organizers in MUS Musculus Subspecies and in the RAG Mouse Cell Line", Genetics, 86, pp. 389-398, (1977).
Du, W. et al., "SlipChip", Lab Chip, 9(16), pp. 2286-2292, (2009). 14 pages.
Engreitz, J.M. et al., "RNA-RNA Interactions Enable Specific Targeting of Noncoding RNAs to Nascent Pre-mRNAs and Chromatin Sites", Cell, 159, pp. 188-199, (2014).
Engreitz, J.M. et al., "The Xist lncRNA Exploits Three-Dimensional Genome Architecture to Spread Across the X-Chromosome", Science, 341(6147), 1237973, (2013). 18 pages.
Frei A.P. et al., "Highly multiplexed simultaneous detection of RNAs and proteins in single cells", Nature Methods,Mar. 2016, vol. 13, No. 3, pp. 269-275, 19 pages.
G-Biosciences, Detergents: Handbook & Selection Guide to Detergents & Detergent Removal, Geno Technology Inc., (2018).
Ge, S. et al., "Digital, Ultrasensitive, End-Point Protein Measurements with Large Dynamic Range via Brownian Trapping with Drift", J. Am. Chem. Soc., 136, pp. 14662-14665, (2014).
Greenwood, C. et al., "Proximity Assays for Sensitive Quantification of Proteins", Biomolecular Detection and Quantification, 4, pp. 10-16, (2015).
Guainazzi, A. et al., "Using Synthetic DNA Interstrand Crosslinks to Elucidate Repair Pathways and Identify New Therapeutic Targets for Cancer Chemotherapy", Cell Mol. Life Sci., 67(21), pp. 3683-3697, (2010). 21 pages.
Harris, M.E. et al., "RNA CrossLinking Methods", Methods Enzymol., 468, pp. 127-146, (2009). 15 pages.
Hoffman, E.A. et al., "Formaldehyde Crosslinking: A Tool for the Study of Chromatin Complexes", Journal of Biological Chemistry, vol. 290, No. 44, pp. 26404-26411, (2015). 9 pages.
Hosic, S. et al., "Microfluidic Sample Preparation for Single Cell Analysis", Analytical Chemistry, 88(1), pp. 354-380, (2016). 58 pages.
International Search Report for International Application No. PCT/US2018/052676 filed on Sep. 25, 2018 on behalf of California Institute of Technology Mail Date: Jan. 23, 2019 7 pages.
International Search Report for International Application No. PCT/US2018/052733 filed on Sep. 25, 2018 on behalf of California Institute of Technology Mail Date: Apr. 18, 2019 4 pages.
Kang, Y. et al., "Single Prokaryotic Cell Isolation and Total Transcript Amplification Protocol for Transcriptomic Analysis", Nature Protocols, vol. 10, No. 7, pp. 974-984, (2015). 12 pages.

Kang, Y. et al., "Transcript Amplification from Single Bacterium for Transcriptome Analysis", Genome Research, Cold Spring Harbor Laboratory, 21, pp. 925-935, (2011). Retrieved on Jan. 7, 2019.
Kennedy-Darling, J. et al., "Measuring the Formaldehyde Protein-DNA Cross-Link Reversal Rate", Analytical Chemistry, 86(12), pp. 5678-5681, (2014).
Le, T.B. et al., "High-Resolution Mapping of the Spatial Organization of a Bacterial Chromosome", Science, vol. 342, pp. 731-734, (2013). 5 pages.
Lee, S.H. et al., "Effective Mixing in a Microfluidic Chip Using Magnetic Particles", Lab on a Chip, 9(3), pp. 479-482, (2009).
Li, L. et al., "Dead-End Filling of SlipChip Evaluated Theoretically and Experimentally as a Function of the Surface Chemistry and the Gap Size Between the Plates for Lubricated and Dry SlipChips", Langmuir, 26(14), pp. 12465-12471, (2010). 17 pages.
Ling, G. et al., "DNase I Digestion of Isolated Nulcei for Genome-Wide Mapping of DNase Hypersensitivity Sites in Chromatin", Methods Molecular Biology, 977, pp. 21-33, (2013). 12 pages.
Liu, W. et al., "SlipChip for Immunoassays in Nanoliter Volumes", Anal. Chem., 82(8), pp. 3276-3282, (2010). 14 pages.
Los, G.V. et al., "HaloTag: A Novel Protein Labeling Technology for Cell Imaging and Protein Analysis", ACS Chemical Biology, vol. 3, No. 6, pp. 373-382, (2008).
Ma, L. et al., "Gene-Targeted Microfluidic Cultivation Validated by Isolation of a Gut Bacterium Listed in Human Microbiome Project's Most Wanted Taxa", PNAS, 111(27), pp. 9768-9763, (2014).
Ma, L. et al., "Individually Addressable Arrays of Replica Microbial Cultures Enabled by Splitting SlipChips", Integr. Biol. (Camb.), 6(8), pp. 796-805, (2014) . 23 pages.
Macosko, E.Z. et al., "Highly Parallel Genome-Wide Expression Profiling Individual Cells Using Nanoliter Droplets", Cell, 161, pp. 1202-1214, (2015).
Motyan, J.A. et al., "Research Applications of Proteolytic Enzymes in Molecular Biology", Biomolecules, 3, pp. 923-942, (2013).
Nagano, T. et al., "Comparison of Hi-C Results using In-Solution Versus In-Nucleus Ligation", Genome Biology, 16, p. 175, (2015). 13 pages.
Nagano, T. et al., "Single Cell Hi-C Reveals Cell-to-Cell Variability in Chromosome Structure", Nature, 502(7469), pp. 59-64, (2013). 14 pages.
Nagano, T. et al., "Single-Cell Hi-C for Genome-Wide Detection of Chromatin Interactions that Occur Simultaneously in a Single Cell", Nature Protocols, vol. 10, No. 12, pp. 1986-2003, (2015).
New England Biolabs. "Restriction Endonucleases." 2018 Sep. 19, 2018]; Available from: https://www.neb.com/products/restriction-endonucleases. Accessed on Sep. 18, 2019.
New England Biolabs. "Types of Restriction Endonucleases." 2018 Sep. 19, 2018]; Available from: https://www.neb.com/products/restriction-endonucleases/restriction-endonucleases/types-of-restriction . . . Accessed on Sep. 18, 2019.
Nilsson, J. et al., "Review of Cell and Particle Trapping in Microfluidic Systems", Analytica Chimica Acta 649, pp. 141-157, (2009).
Pamme, N., "Magnetism and Microfluidics", Lab Chip, 6, pp. 24-38, (2006).
Pompano, R.R. et al., "Control of Initiation, Rate, and Routing of Spontaneous Capillary-Driven Flow of Liquid Droplets through Microfluidic Channels on SlipChip", Langmuir, 28(3), pp. 1931-1941, (2012). 23 pages.
ProteoChem, DSG Crosslinker Protocol and Product Information Sheet, Loves Park, IL., USA, (2014). 1 page.
Quinodoz, S.A. "Split-Pool Recognition of Interactions by Tag Extension [SPRITE] for DNA: Experimental Protocols" SPRITE Protocol, Jan. 21, 2018, 34 pages.
Quinodoz, S.A. et al., "Higher-Order Inter-Chromosomal Hubs Shape 3D Genome Organization in the Nucleus", Cell, 174(3), pp. 744-757, e24, (2018).
Ramani V. et al., "Massively multiplex single-cell Hi-C" Nature Methods,2017, 7 pages.
Ramani, V. et al., "High-Throughout Determination of RNA Structure by Proximity Ligation", Nat. Biotechnol., 33(9), pp. 980-984, (2015). 18 pages.

(56) References Cited

OTHER PUBLICATIONS

Ramani, V. et al., "Mapping Three-Dimensional Genome Architecture through in situ DNase Hi-C", Nature Protocols, 11(11), pp. 2104-2121, (2016). 32 pages.
Rao, S.S. et al., "A 3D Map of the Human Genome at Kilobase Resolution Reveals Principles of Chromatin Looping", Cell 159, pp. 1665-1680, (2014).
Rotem, A. et al., "Single-Cel ChIP-seq Reveals Cell Subpopulations Defined by Chromatin State", Nat. Biotechnol., 33(11), pp. 1165-1172, (2015). 25 pages.
Schramm, L.L. et al., "Surfactants and Their Applications", Annu. Rep. Prog. Chem., Section C, 99, pp. 3-48, (2003).
Selck, D.A. et al., "Increased Robustness of Single-Molecule Counting with Microfluidics, Digital Isothermal Amplification, and a Mobile Phone Versus Real-Time Kinetic Measurements", Anal. Chem., 85(22), pp. 11129-11136, (2013). 19 pages.
Shahi P. et al., "Abseq: Ultrahigh-throughput single cell protein profiling with droplet microfluidic barcoding", *Scientific Reports*, Mar. 14, 2017, vol. 7, Article No. 44447, pp. 1-12.
Shen, F. et al., "Digital Isothermal Quantification of Nucleic Acids via Simultaneous Chemical Initiation of Recombinase Polymerase Amplification Reactions on SlipChip", Analytical Chemistry, 83(9), pp. 3533-3540, (2011). 17 pages.
Shen, F. et al., "Digital PCR on a SlipChip", Lab on a Chip, 10, pp. 2666-2672, (2010). 15 pages.
Shen, F. et al., "Multiplexed Quantification of Nucleic Acids with Large Dynamic Range Using Multivolume Digital RT-PCR on a Rotational SlipChip Tested with HIV and Hepatitis C Viral Load", Journal of the American Chemical Society, 133(44), pp. 17705-17712, (2011). 17 pages.
Shen, F. et al., "Nanoliter Multiplex PCR Arrays on a SlipChip", Analytical Chemistry, 82(11), pp. 4606-4612, (2010). 16 pages.
Shishkin, A.A. et al., "Simultaneous Generation of Many RNA-Seq Libraries in a Single Reaction", Nature Methods, 12(4), pp. 323-325, (2015). 10 pages.
Sigma Aldrich. "Cell Dissociation with Trypsin." ,2018 Sep. 19, 2018]; Available from: https://www.sigmaaldrich.com/technical-documents/articles/biology/cell-dissociation-with-trypsin.html. Accessed on Sep. 18, 2019.
Sigma Aldrich. "Removal of Adherent Cells from a Culture Surface Using Trypsin." 2018 Sep. 19, 2018]; Available from: https://www.sigmaaldrich.com/technical-documents/protocols/biology/removal-of-adherent-cells.html Accessed on Sep. 18, 2019.
Singh, V. et al., "Genetically Encoded Multispectral Labeling of Proteins with Polyfluorophores on a DNA Backbone", J. Am. Chem. Soc., 135(16), pp. 6184-6191, (2013). 19 pages.
Soderberg, O. et al., "Direct Observation of Individual Endogenous Protein Complexes in situ by Proximity Ligation", Nature Methods, vol. 3, No. 12, pp. 995-1000, (2006). 7 pages.
Stone, M.P. et al., "Interstrand DNA Cross-Links Induced by Alpha, Beta-Unsaturated Aldehydes Derived From Lipid Peroxidation and Environmental Sources", ACC Chem. Res., 41(7), pp. 793-804, (2008). 28 pages.
Sun, B. et al., "Measuring Fate and Rate of Single-Molecule Competition of Amplification and Restriction Digestion, and Its Use for Rapid Genotyping Tested with Hepatitis C Viral RNA", Angew Chem. Int. Ed. Engl., 53(31), pp. 8088-8092, (2014). 11 pages.
Sun, B. et al., "Mechanistic Evaluation of the Pros and Cons of Digital RT-LAMP for HIV-1 Viral Load Quantification on a Microfluidic Device and Improved Efficiency via a Two-Step Digital Protocol", Analytical Chemistry, 85(3), pp. 1540-1546, (2013). 14 pages.
Taanman, J.W. "The Mitochondrial Genome: Structure, Transcription, Translation, and Replication", Biochimica et Biophysica Acta, 1410(2), pp. 103-123, (1999).
Thermo Fisher Scientific Inc., Instructions: Imidoester Crosslinkers: DMA, DMP, DMS, DTBP, Rockford, IL., USA, (2012). 2 pages.
Tian, B. et al., "Two-Step Cross-Linking for Analysis of Protein-Chromatin Interactions", Methods in Molecular Biology, vol. 809, pp. 105-120, (2012). 17 pages.
Weibrecht, I. et al., "Proximity Ligation Assays: A Recent Addition to the Proteomics Toolbox", Expert Review of Proteomics, 7(3), pp. 401-409, (2010). 10 pages.
Wikipedia. "Crosslinking of DNA." 2018 [cited 2018]Sep. 19, 2018; Available from: https://en.wikipedia.org/wiki/Crosslinking_of_DNA. Accessed on Sep. 18, 2019.
Written Opinion for International Application No. PCT/US2018/052676 filed on Sep. 25, 2018 on behalf of California Institute of Technology Mail Date: Jan. 23, 2019 10 pages.
Written Opinion for International Application No. PCT/US2018/052733 filed on Sep. 25, 2018 on behalf of California Institute of Technology Mail Date: Apr. 18, 2019 8 pages.
Xin, Y. et al., "Use of the Fluidigm C1 Platform for RNA Sequencing of Single Mouse Pancreatic Islet Cells", PNAS, vol. 113, No. 12, pp. 3293-3298, (2016).
Non-Final Office Action for U.S. Appl. No. 16/141,901, filed Sep. 25, 2018 on behalf of California Institute of Technology. Mail date: Apr. 29, 2020. 15 Pages.
Clancy S. "Chemical Structure of RNA" *Nature Education*, vol. 7(1),2008, 4 pages.
Clancy S. "RNA Functions" Nature Education, vol. 1(1), 2008, 4 pages.
Final Office Action for U.S. Appl. No. 16/141,901, filed Sep. 25, 2018 on behalf of California Institute of Technology Mail Date: Jan. 25, 2021 14 pages.
Non-Final Office Action for U.S. Appl. No. 16/141,901, filed Sep. 25, 2018, on behalf of California Institute of Technology. Mail Date: Jul. 21, 2021. 14 Pages.
Final Office Action for U.S. Appl. No. 16/141,901, filed Sep. 25, 2018 on behalf of California Institute of Technology Mail Date: Apr. 5, 2022 14 pages.
Advisory Action for U.S. Appl. No. 16/141,901, filed Sep. 25, 2018, on behalf of California Institute of Technology. Mail Date: Sep. 21, 2022. 5 Pages.
Notice of Allowance for U.S. Appl. No. 16/141,901, filed Sep. 25, 2018 on behalf of California Institute of Technology Mail Date: Nov. 25, 2022 16 pages.

\* cited by examiner

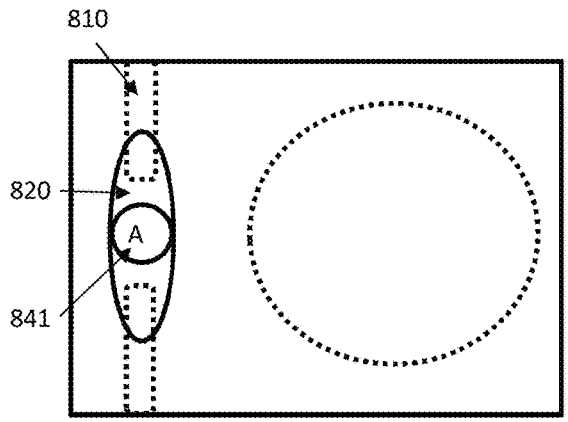
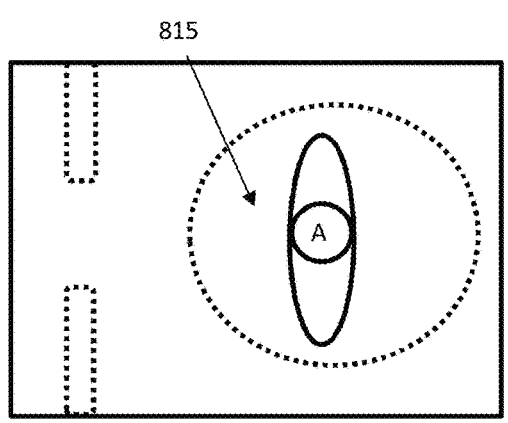
FIG. 8A  FIG. 8B
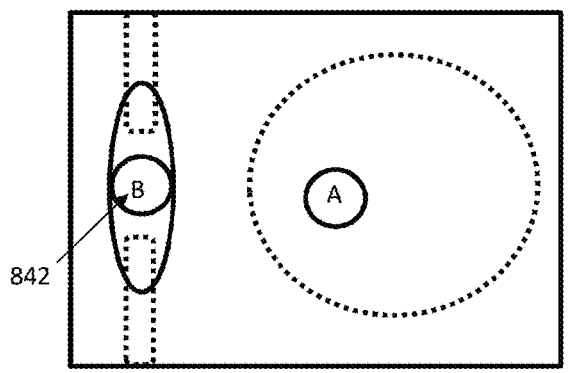
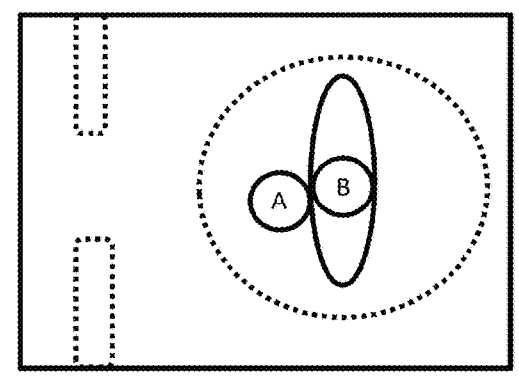
FIG. 8C  FIG. 8D
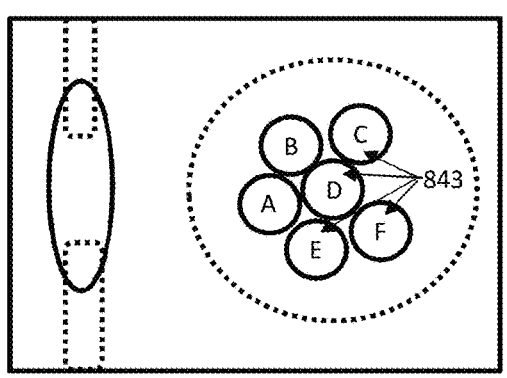
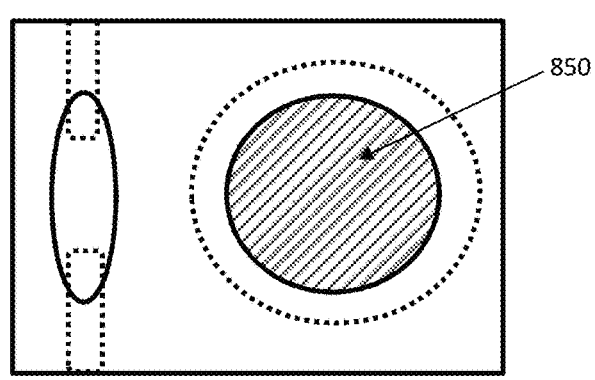
FIG. 8E  FIG. 8F Detection probability of spike-in control (ERCC) for SlipChip RNAseq and Drop-seq methods.

RNA-Seq reads from single mouse ES v6.5 cells to illustrate the connection between on-device images and sequening.

Using repaired human RNA (67.2 pg/8nL well) to check for on-device bias. Barcodes are shown acording to spatial placement within device. (A) total reads per barcode; (B) gene count per barcode. Squencng depth: 3.7e7 paired-end reads.

DEVICE FOR ADDITIVE DELIVERY OF REAGENTS AND RELATED METHODS AND SYSTEMS

CROSS-REFERENCE TO RELATED APPLICATIONS

The present application claims priority to U.S. Provisional Application No. 62/562,684, entitled "Methods and Devices for Studying Single Cell Dynamics and Interactions of Nucleic Acids" filed on Sep. 25, 2017, and to Provisional Application No. 62/562,894, entitled "Methods and Devices for Single Cell Sequencing and Analysis of Nucleic Acids" filed on Sep. 25, 2017 the entire disclosure of each of which is incorporated herein by reference in its entirety.

STATEMENT OF GOVERNMENT GRANT

This invention was made with government support under Grant No. HL130007 and under Grant No. EB012946 awarded by the National Institutes of Health. The government has certain rights in the invention.

FIELD

The present disclosure relates to microfluidics devices and in particular it relates to a device for additive delivery of reagents and related methods and systems.

BACKGROUND

The present invention relates to fluidic devices for compartmentalizing samples. In particular, such devices allow for multiple reactions to be performed while minimizing contamination.

Fluidic devices and systems are useful for conducting various types of reactions for small sample volumes by compartmentalizing a sample into isolated compartments. Such devices and systems are useful for various types of assays, such as single cell analysis, single molecule analysis, and multiplex reactions.

Despite developments in the field, however providing simplified fluidic devices and systems capable of utilizing small isolated chambers for performing multiple reaction steps with efficient delivery of multiple reagents in an all-hydrophobic surface device, without cross-contamination between steps, is still challenging.

SUMMARY

A fluidic device for compartmentalizing samples and related systems and methods of use thereof are provided which in several embodiments allow additive delivery of reagents, which minimize cross-contamination and/or allows separate delivery of multiple reagents.

In a first aspect, a device is described, the device comprising: a first plate comprising a first surface; and a second plate with a second surface, the first surface in contact with the second surface, both the first surface and the second surface being hydrophobic.

In the device of the first aspect, the first plate has on the first surface a loading channel and pooling wells, each comprising a trap well, and the second plate has on the second surface channel-loaded loading wells.

In the device of the first aspect, the channel-loaded loading wells are configured to be aligned in a one-to-one correspondence with the pooling wells when the first plate and the second plate are in a first position with respect to each other.

In the device of the first aspect, the channel-loaded loading wells are further configured to be aligned with the loading channel such that material in the loading channel can access the channel-loaded loading wells when the first plates and the second plate are in a second position with respect to each other.

In a second aspect, a device is described, the device comprising: a first plate comprising a first surface; and a second plate with a second surface, the first surface in contact with the second surface, both the first surface and the second surface being hydrophobic.

In the device of the second aspect, the first plate has on the first surface a loading channel and pooling wells, and the second plate has on the second surface channel-loaded loading wells.

In the device of the second aspect, the channel-loaded loading wells are configured be aligned in a one-to-one correspondence with the pooling wells when the first plate and the second plate are in a first position with respect to each other.

In the device of the second aspect, the channel-loaded wells are further configured to be aligned with the loading channel such that material in the loading channel can access the channel-loaded loading wells when the first plates and the second plate are in a second position with respect to each other, and the loading wells have a greater depth than the loading channel.

In a third aspect, a device is described, the device comprising: a first plate comprising a first surface; and a second plate with a second surface, the first surface in contact with the second surface, both the first surface and the second surface being hydrophobic.

In the device of the third aspect, the first plate has on the first surface a loading channel and pooling wells; and the second plate having on the second surface channel-loaded loading wells.

In the device of the third aspect, the channel-loaded loading wells are configured be aligned in a one-to-one correspondence with the pooling wells when the first plate and the second plate are in a first position with respect to each other.

In the device of the third aspect, the channel-loaded wells are further configured to be aligned with the loading channel such that material in the loading channel can access the channel-loaded loading wells when the first plates and the second plate are in a second position with respect to each other.

In the device of the third aspect, the channel-loaded loading wells each have a side opposite a direction from the loading channel to the pooling wells the direction perpendicular to the loading channel, the side comprising two walls at equal angles from a bisector of the each channel-loaded loading wells parallel to the direction from the loading channel to the pooling wells, the equal angles each being less than 90 degrees.

In a fourth aspect, a method for providing microfluidic mixing is described. The method comprises: providing a device comprising: a first plate comprising a first surface; and a second plate with a second surface, the first surface in contact with the second surface; the first plate having on the first surface a first set of wells; and the second plate having on the second surface a second set of wells.

The method of the fourth aspect further comprises sliding the first plate relative to the second plate in a first direction, placing the first set of wells co-centered with the second set of wells; and sliding the first plate relative to the second plate in a second direction orthogonal to the first direction, creating a continuous channel from the first set of wells and the second set of wells.

In a fifth aspect, a method for providing microfluidic mixing is described. The method comprises: providing a device, the device comprising: a first plate comprising a first surface; and a second plate with a second surface, the first surface in contact with the second surface; the first plate having on the first surface a loading channel and pooling wells; and the second plate having on the second surface channel-loaded loading wells and an elution channel; wherein the channel-loaded loading wells are configured be aligned in a one-to-one correspondence with the pooling wells when the first plate and the second plate are in a first position with respect to each other and are configured to be aligned with the loading channel such that material in the loading channel can access the channel-loaded loading wells when the first plates and the second plate are in a second position with respect to each other.

The method of the fifth aspect also comprises sliding the first plate relative to the second plate in a first direction to allow loading of the loading wells from the loading channel; sliding the first plate relative to the second plate in the first direction to allow drop-in from the loading wells to the pooling wells; and sliding the first plate relative to the second plate in a second direction opposite the first direction to allow elution of the pooling wells using the elution channel.

In a sixth aspect, a method for ligating an adaptor to nucleic acid is described, the method comprising: providing a device, the device comprising: a first plate comprising a first surface; and a second plate with a second surface, the first surface in contact with the second surface; the first plate having on the first surface a loading channel and pooling wells; and the second plate having on the second surface a first set of channel-loaded loading wells, a second set of channel-loaded loading wells, and adapter wells, the adapter wells each being pre-spotted with uniquely barcoded adapters for each adapter well; wherein the channel-loaded loading wells are configured to be aligned with the loading channel such that material in the loading channel can access the channel-loaded loading wells when the first plates and the second plate are in a first position with respect to each other and are configured be aligned in a one-to-one correspondence with the pooling wells when the first plate and the second plate are in a second position with respect to each other, and the adapter wells are configured to be aligned in a one-to-one correspondence with the pooling wells when the first plate and the second plate are in a third position with respect to each other; loading at least two of the pooling wells with biological material comprising nucleic acid; sliding the first plate and the second plate to the second position and loading the first set of channel-loaded loading wells with an extraction buffer or a digestion buffer through the loading channel; sliding the first plate and the second plate to the first position and dropping-in the extraction buffer or digestion buffer from the first set of channel-loaded loading wells to the pooling wells; sliding the first plate and the second plate to the third position and dropping-in the adapters from the adapter wells to the pooling wells; loading the second set of channel-loaded loading wells with ligation mix through the loading channel; sliding the first plate and the second plate relative to each other to a fourth position, such that the second set of channel-loaded loading wells are aligned in a one-to-one correspondence with the pooling wells and dropping-in the ligation mix from the second set of channel-loaded loading wells to the pooling wells, while the at least two pooling wells contain both the nucleic acid and corresponding adapters.

The method of the sixth aspect can also comprise wherein the loading the pooling wells with nucleic acid is done through the loading channel.

The method of the sixth aspect can also comprise wherein the loading of the second set of channel-loaded loading wells is performed while the first plate and the second plate are in the third position.

The devices, methods and systems herein described in several embodiments allow microfluidics with multiple reactants together in isolated chambers with reduced loss of material compared with microfluidic devices configured to add materials through channels directly to pooling wells where reactions are performed.

The devices, methods and systems herein described in several embodiments allow microfluidics with multiple reactants minimizing cross-contamination between chambers.

The devices, methods and systems herein described in several embodiments allow microfluidics using only hydrophobic surfaces, allowing an easy cleaning of microfluidic chambers.

The devices, methods and systems herein described in several embodiments allow using the broad choice and concentration of detergents and reagents selected to lyse variable types of samples (e.g. eukaryotic cells, cell nuclei, or prokaryotic cells) simultaneously in multiplex manner.

The devices, methods and systems herein described in several embodiments allow imaging of the samples loaded inside device and tracking the wells identities through specific barcoding. The devices, methods and systems herein described in several embodiments allow using multiple step by step biochemical reactions that require variable (often incompatible) buffers be performed efficiently in additive manner, without intermediate clean ups. The devices, methods and systems herein described in several embodiments allow using multiple step by step biochemical reactions that require variable (often incompatible) temperature conditions be performed efficiently in additive manner, without intermediate clean ups. The devices, methods and systems herein described in several embodiments allow efficient extraction of nucleic acids, and efficient downstream reparation, and ligation reactions in the additive manner, as well as efficient reverse transcription, digestion, tailing, or amplification, with no need for any intermediate clean ups. It provides for the rich choice of strategies for barcoding nucleic acids from single cells and enables targeting both polyadenylated RNA and non-polyadenylated RNA.

The devices, methods and systems herein described can be used in connection with various applications wherein microfluidics is desired. For example, the devices, methods and systems herein described can be used in single-cell research, single-molecule assays, cell-cell interaction studies, clonal micro-colony studies, combinatorial approaches to protein crystallization, chemical synthesis, kinetics studies, bio-medical diagnostics, and titration. Additional exemplary applications include uses of the methods and systems and related compositions, herein described in several fields including basic biology research, applied biology, bio-engineering, aetiology, medical research, medical diagnostics, therapeutics, and in additional fields identifiable by a skilled person upon reading of the present disclosure.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and example sections, serve to explain the principles and implementations of the disclosure. Exemplary embodiments of the present disclosure will become more fully understood from the detailed description and the accompanying drawings, wherein:

FIGS. 8A-8F show an example device used for additive combination of material.

FIGS. 25 and 26 represent dose-response plots of ERCC spike-in transcripts from two single-cell *E. coli* experiments. The reads are averaged across all barcodes.

FIGS. 27 and 28 represent probability of detection curves, based on ERCC spike-in detection data from two single-cell *E. coli* experiments (FIG. 27 is related to data shown in FIG. 25, FIG. 28 is related to data shown in FIG. 26). From these fits, device 1 had 14 copies for 50% probability of detection; device 2 had 21 copies for 50% probability of detection.

FIG. 29 shows example read coverages for two difference spike-in transcripts (ERCC00025 and ERCC00116) of different abundance in two different wells on device (barcodes E04 and G04). This illustrates the full-length coverage capability of the method

DETAILED DESCRIPTION

Figure 1:
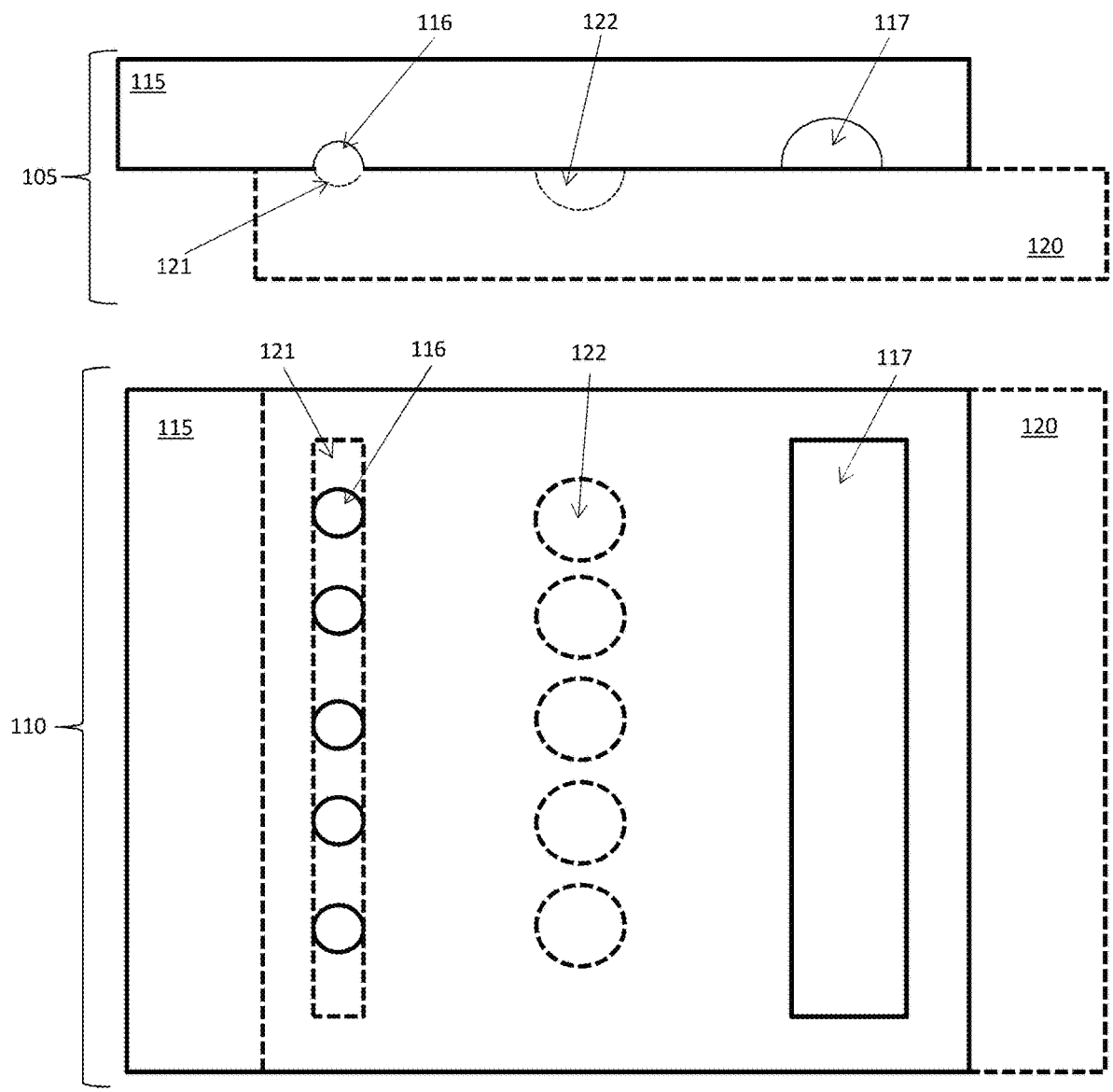
FIG. 1 shows an example device (not to scale) in position to load loading wells, side (cross-sectional) and top views.

In order to facilitate multiple reaction steps in isolated chambers, a microfluidic device can be arranged with two opposing plates-one plate consisting of loading wells, the other plate including a loading channel and of pooling wells configured to align with the loading wells in a one-to-one correspondence. This allows loading of the loading wells by the loading channel when the plates are aligned in one configuration and depositing from the loading wells to the pooling wells in another configuration. These configurations can be "slid" back and forth to add more reaction steps (or just more reactants) in the pooling wells while keeping the pooling wells isolated from each other.

"Device" as used herein refers to a microfluidic device including two plates in contact with each other, such that wells and/or channels are present at the interface of the plates.

"Plate" as used herein refers to half of a device, a monolithic sheet with wells and/or channels shaped on one of its major surfaces. The plates of the device can be made of any suitable material for microfluidics. Suitable materials include, but are not limited to, polymeric materials, such as silicone polymers (e.g., polydimethylsiloxane and epoxy polymers), polyimides (e.g., commercially available Kapton® (poly(4,4'-oxydiphe-55 nylene-pyromellitimide) from DuPont and Upilex™ (poly(biphenyl tetracarboxylic dianhydride)), from Ube Industries), polycarbonates, polyesters, polyamides, polyethers, polyurethanes, polyfluorocarbons, fluorinated polymers (e.g., polyvinylfluoride, polyvinylidene fluoride, polytetrafluoroethylene, polychlorotrifluoroethylene, perfluoroalkoxy polymer, fluorinated ethylene-propylene, polyethylenetetrafluoroethylene, polyethylenechlorotrifluoroethylene, perfluoropolyether, perfluorosulfonic acid, perfluoropolyoxetane, 65 FFPM/FFKM (perfluorinated elastomer [perfluoroelastomer]), FPM/FKM (fluorocarbon [chlorotrifluoroethylenevinylidene fluoride]), as well as copolymers thereof), polyetheretherketones (PEEK), polystyrenes, poly(acrylonitrile-butadiene-styrene)(ABS), acrylate and acrylic acid polymers such as polymethyl methacrylate, and other substituted and unsubstituted polyolefins (e.g., cycloolefin polymer, polypropylene, polybutylene, polyethylene (PE)(e.g., cross-linked PE, high-density PE, medium-density PE, linear low-density PE, low-density PE, or ultra-high-molecular-weight PE)), polymethylpentene, polybutene-I, polyisobutylene, ethylene propylene rubber, ethylene propylene diene monomer (M-class) rubber, and copolymers thereof (e.g., cycloolefin copolymer); ceramics, such as aluminum oxide, silicon oxide, zirconium oxide, and the like); semiconductors, (e.g. silicon, gallium arsenide); glass; metals; as well as coated combinations and composites of the above (e.g., a block composite, e.g., an A-B-A block composite, an A-B-C block composite, or the like, of any materials described herein), and laminates of the above (such as polymer laminates or polymermetal laminates (e.g. polymer coated with copper, a ceramic-in-metal, or a polymer-in-metal composite)).

"Chambers" as used herein refers to etched/carved out portions of the plates that can act as wells or channels or both.

"Wells" as used herein refers to isolated volume compartments of any size created by voids in the plate.

"Channels" as used herein refers to long voids in the material of the plate that can allow input or output of fluids from the device. A channel can connect to multiple wells at once, but a well will only connect to a single other well or a single channel at a time, depending on the relative positions of the plates on the device. Channels can also include vias through the plate to facilitate flowing a liquid through the channel from outside the device.

As used herein, "loading channels" (or "connecting channels") refers to channels used to input material to the device for depositing into a well, and "elution channels" refers to channels used to wash out material from the device, either to eject material from wells or to clean out other channels.

As used herein, "loading well" (or "carrier wells") refers to smaller wells that are used to drop in objects and reagents into pooling wells. Loading wells can be "channel-loaded", indicating that they receive their material from a channel after assembly of the device, or "pre-loaded", indicating they are loaded (pre-spotted) with material before assembly of the device.

As used herein, "adapter well" refers to a pre-loaded loading well that has been spotted with an adapter (genetic linker) for delivery to a pooling well.

As used herein, "pooling well" (or "mixing well" or "reaction well") refers to larger wells that are used to gather the reagents for reaction. Pooling wells are larger than loading wells in volume, as they have to accommodate multiple reagents being delivered either by multiple loading wells, or by a set of loading wells being reused for multiple loads of reagents, and they have to provide a surface tension driving force between the loading wells and the pooling wells, such that non-wetting droplets transfer from the loading wells to the pooling wells without the use of hydrophilic surfaces.

Because of the difference in well depths between loading wells and pooling wells (e.g. 100 µm pooling well versus 50 µm loading wells), multistep device allows delivery of reagents in additive fashion, rather than one-time loading where the entire well gets filled to capacity. Loading on the multistep device can be achieved by either dropping in different reagents using the same array of loading wells over and over, or by using different arrays of other volumes, or combination of the two.

As used herein, "alignment well" is a well that is used for ensuring correct positioning the plates before and after sliding, but is not used for loading or pooling material. An alignment well is aligned with alignment protuberances in the opposite plate, such that the protuberances fit in the corresponding alignment wells.

As used herein, "trapping well" refers to an area in the pooling well that has increased depth compared to the rest of the pooling well. A trapping well in the sense of the disclosure is not a separate well as such, but a decrease in depth in another well. The depth of a trapping well is expressed as the difference in depth from the corresponding well.

"Sliding" as used herein refers to the changing of relative positions of the plates of the device, thereby changing the alignment of wells and/or channels of one plate with wells and/or channels of the other plate. The plates remain in contact during sliding. Sliding is facilitated by the plates being immersed in oil during assembly of the device. Since the positioning of the plates is relative to each-other, the absolute motion of each plate is irrelevant to the sliding (e.g. moving the top plate in one direction and keeping the bottom plate still is equivalent to moving the bottom plate in the opposite direction, or moving both plates in opposite directions).

As used herein, "loading" refers to the filling of wells by the use of the channels. Loading is achieved by aligning channel-loaded loading wells in one plate with connecting (loading) channels in the other plate. This prevents cross-contamination between wells during manipulation. For example, the size, shape, and spacing of the features can be selected so that any adaptor wells do not come in contact with the channels during manipulation. Also, the connecting channels and loading wells are of slightly different depths (e.g. 50 µm for loading wells versus 40 µm for the loading channel) to promote filling of the loading wells. For example, for a PDMS (polydimethylsiloxane) oil used between the plates, the loading channel can have a depth as low as 20 µm, but generally the shallower the depth, the slower the loading time from loading channel to loading well.

As used herein, "drop-in" or "dropping-in" refers to the depositing of material from either a channel-loaded loading well or a pre-loaded loading well into a pooling well. In the case of an adapter well, it can refer to allowing the adapters to hydrate and mix in with the pooling well, rather than physically "dropping in".

Poisson distribution loading of loading wells: cell encapsulation (i.e. loading a single object to an individual well) can be performed wherein droplets are produced continuously at high rates by pumping fluids through microfluidic structures (loading channels and loading wells) of known geometry. Typically, the number of cells encapsulated per droplet can be estimated by Poisson statistics, such that loading wells can be filled with a singular object (cell, nucleus, virus, phage, etc.). Alternative methods include active (molecular) trapping and trapping by size. Sec, for example, "Review of cell and particle trapping in microfluidic systems" by J. Nilsson et al. (*Analytica Chimica Acta*, Volume 649, Issue 2, 7 Sep. 2009, Pages 141-157)[2], the contents of which are incorporated by reference herein.

Transfer of material from loading wells to pooling wells can be performed by capillary action. There is a simple physical model developed to describe the flow of nonwetting droplets from loading wells to pooling wells, based on the balance of capillary pressure and pressure due to flow resistance. Qualitatively, a nonwetting droplet (θ>90°) is driven forward by capillary pressure if there is greater curvature at the back of the droplet than at its front. The capillary pressure, at the liquid-liquid interface between a nonwetting aqueous droplet and immiscible wetting oil is determined by the liquid-liquid interfacial tension, the three-phase contact angle, and the geometry of the device. A general explanation of the capillary action in microfluidics can be found in "Control of Initiation, Rate, and Routing of Spontaneous Capillary-Driven Flow of Liquid Droplets through Microfluidic Channels on SlipChip", by Rebecca R. Pompano et al. (Langmuir, vol. 28(3), pp. 1931-1941, 2012) [3], the contents of which are incorporated by reference herein.

The term "nucleic acid" as used herein indicates a polymeric form of nucleotides of any length, either ribonucleotides or deoxyribonucleotides, that comprise purine and pyrimidine bases, or other natural, chemically or biochemically modified, non-natural, or derivatized nucleotide bases. Nucleic acids of the embodiments of the current disclosure include Deoxyribonucleic acid (DNA), ribonucleic acid (RNA), or DNA copies of RNA (complementary DNA or cDNA), which can be isolated from natural sources, recombinantly produced, or artificially synthesized. The nucleic acids can exist as single-stranded or double-stranded and any chemical and biochemical modifications thereof, provided only that the modification does not interfere with amplification of the resulting nucleic acids. For example, the backbone of the nucleic acid can comprise sugars and phosphate groups or modified or substituted sugar or phosphate groups, and a nucleic acid can comprise modified nucleotides, such as methylated nucleotides and nucleotide analogs. A polynucleotide of 5 to 50 nucleotide is also called a protein oligomer, peptide, or oligopeptide. In particular, the term oligonucleotide usually indicates a polynucleotide with less than 30 nucleotides. Nucleic acid can be found in biological material (cells, cell nuclei, viruses, etc.).

The term "sample" as used herein indicates a limited quantity of something that is indicative of a larger quantity of that something, including but not limited to fluids from an isolate or a specimen such as biological environment, cultures, tissues, commercial recombinant proteins, synthetic compounds or portions thereof. In particular biological sample can comprise one or more cells of any biological lineage, as being representative of the total population of similar cells in the sampled individual. Individuals biological organism that can be sampled comprise any single multicellular organism, such as plants or animals and in particular higher animals more particularly vertebrates such as mammals and in particular human beings. Exemplary biological samples (aka "biological material") comprise the following: adherent or suspension cell lines (and in particular embryonic stem cells or differentiated pluripotent stem cells), viruses, check tissue, whole blood, dried blood spots, organ tissue, plasma, urine, mucus, mucosal secretions, vaginal fluids and secretions, urethral fluids and secretions, feces, skin, hair, or tumor cells, among others identifiable by a skilled person. Biological samples can be obtained using sterile techniques or non-sterile techniques, as appropriate for the sample type, as identifiable by persons skilled in the art. Some biological samples can be obtained by contacting a swab with a surface on a human body and removing some material from said surface, examples include throat swab, urethral swab, oropharyngeal swab, cervical swab, vaginal swab, genital swab, anal swab. Depending on the type of biological sample and the intended analysis, biological samples can be used freshly for sample preparation and analysis or can be fixed using fixative. Preferably, in methods and systems herein described the sample comprises live cells.

FIG. 1 shows an example device (not to scale—the channels and wells would be much smaller) including two plates (115, 120), shown in cross-sectional side view (105) and top down view (110). To aid understanding of the correspondence between the views, the features of the top plate (115) are shown with solid lines, and the features of the bottom plate (120) are shown in dashed lines.

FIG. 1 shows the device with plates (115, 120) positioned for loading of the channel-loaded loading wells (116). The loading wells (116) are aligned with the loading channel (121) of the opposite plate. This allows the loading of material from the loading channel (121) to the loading wells (116). Pooling wells (122) are positioned in-line longitudinally with corresponding loading wells (116), so that when the plates (115, 120) are slid together, the loading wells (116) will be over corresponding pooling wells (122) (See FIG. 2). An eluting channel (117) is in the plate (115) that is opposite the pooling wells (122).

Typically, loading is performed with some type of fluid-transferring instrument (e.g. a micropipette) at the device inlet, which can be combined with another fluid-transferring device at the outlet creating negative relative pressure to speed up the process. This device can be slid either before removing these instruments (sliding under pressure induces more complete loading), or after removing these instruments, or by removing one instrument, sliding one side, then removing the second instrument, and sliding the other side of the device. In case of sliding after removing the instruments, once the externally-induced pressure drop is gone, the non-wetting sample phase will begin assuming the most energetically favorable conformation, as dictated by its surface energy. If the loading wells (116) and the loading channels (121) are both made of equal depth, the non-wetting sample phase will have no energetic incentive to occupy one feature over the other and can be evenly distributed in both (e.g. filling ~50% of the volume of each loading well and ~50% of the volume of each loading channel). Another possibility is that the non-wetting phase can distribute itself randomly within these features, due to presence of microscopic surface defects and/or particles. To make the loading more robust to these factors and reproducible, both from well-to-well in a single loading event, and from loading-to-loading of each well, the loading wells (116) can be made more deep than the loading channels (121), thereby making it more energetically favorable for the wetting phase to occupy the loading wells than the slightly shallower loading channels, making loading well filling more complete and reproducible even with hydrophobic surfaces for both plate surfaces (i.e. for both the loading channels and loading wells). Some examples of depths: 50 μm deep loading wells, 40 μm deep loading channels; 40 μm deep loading wells, 30 μm deep loading channels; 100 μm deep loading wells, 50 µm deep loading channels; and 150 µm deep loading wells, 100 µm deep loading channels.

Figure 2:
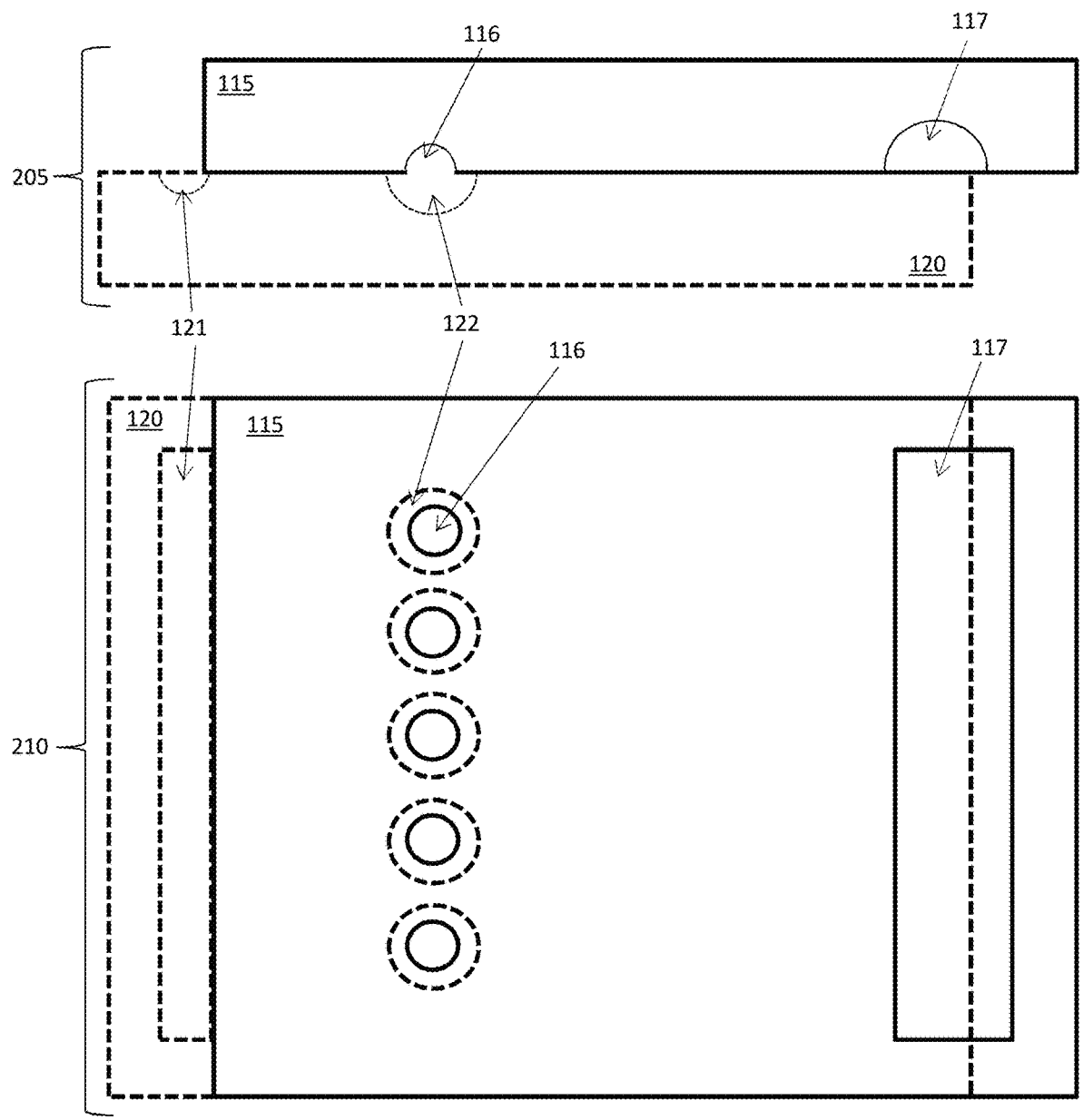
FIG. 2 shows the example device of FIG. 1 in position to drop in from loading wells to pooling wells, side (cross-sectional) and corresponding top views.

FIG. 2 shows the example device of FIG. 1, where the plates (115, 120) have been slid into a different position, as shown in the new cross-sectional side view (205) and the new top view (210). In the different position, the loading wells (116) are over the corresponding pooling wells (122) allowing the contents of the loading wells (116) to drop into the pooling wells (122) in an isolated manner. The transfer from the loading wells (116) to the pooling wells (122) can be due to capillary action, given the relative size difference between the smaller loading wells (116) and the larger pooling wells (122).

Figure 5:
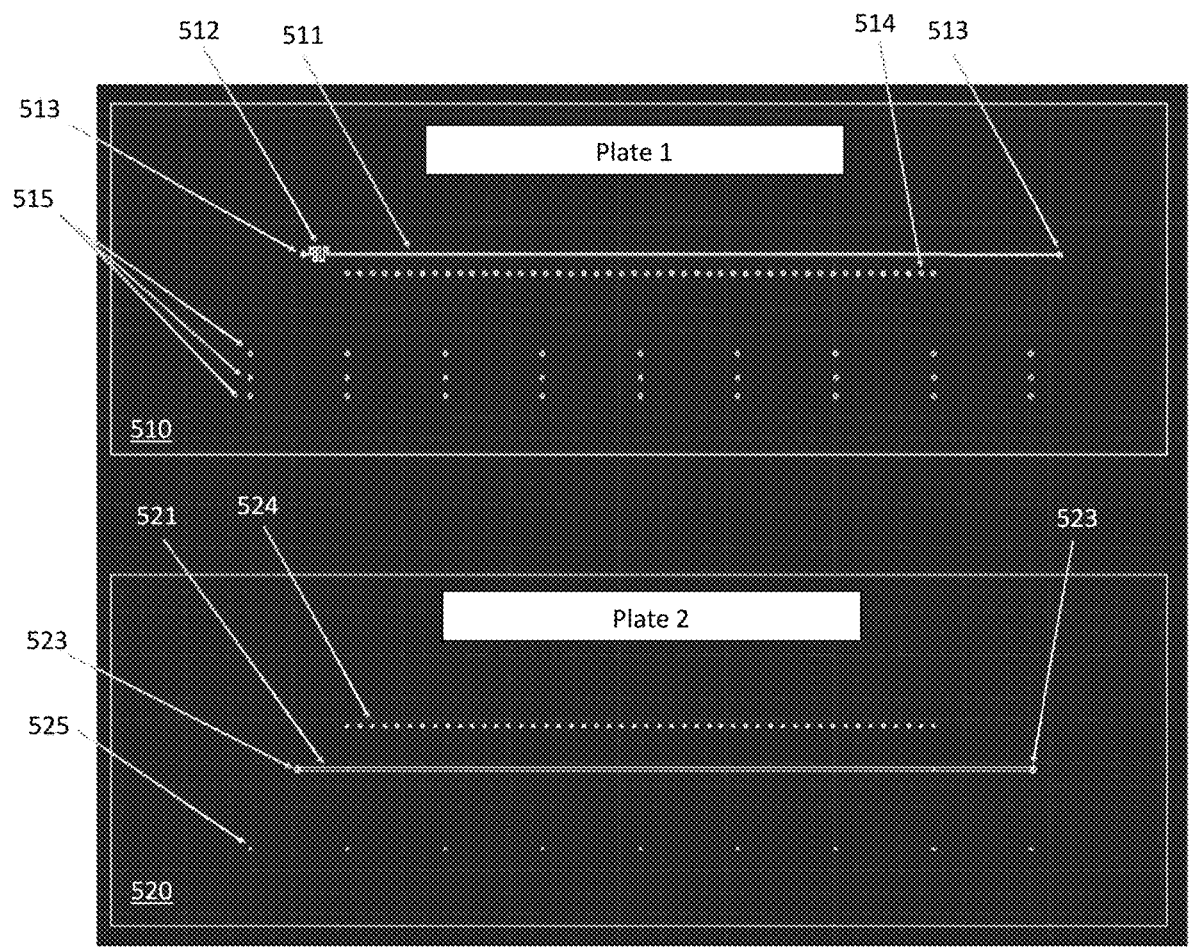
FIG. 5 shows a schematic of the plates of an example device, including alignment wells.

FIG. 5 shows an example schematic of two plates used to create a device. Plate 1 (510) contains the loading channel (511), pooling wells (514), and alignment wells (515). The loading channel (511) includes vias (513) at either end and a serpentine structure (512) at the outlet of the loading channel (511) to increase backpressure and ensure proper complete loading. The alignment wells (515) are positioned to allow precise alignment after each slide of the plates. There are three rows because there are three positions to be aligned: loading well to loading channel, loading well to pooling well, and pooling well to elution channel. Plate 2 (520) includes loading wells (524), an elution channel (521), and alignment protuberances (525) to fit in the corresponding alignment wells (515). As with the loading channel (511), the elution channel has vias (523) for allowing fluid to be pumped through. Note that the pooling wells (514) are significantly larger than the loading wells (524), and the elution channel (521) is noticeably wider (cross-sectionally) than the loading channel (511). This is due to the difference in the roles those features take, microfluidically.

Since the droplets, especially early-on in the protocol, are much lower in volume than the volume of the pooling wells, it is helpful to have these droplets to be in a predictable location (and one that will be most convenient for merging, especially earlier on, before the droplets get big in the pooling well) within each pooling well. For some applications (e.g. single-cell RNA sequencing, abbreviated as scRNAseq) it is desired to have a narrow distribution of times for all merging events to happen in some steps of the protocol (e.g. lysis buffer addition in scRNAseq protocol). Without the traps, the drop-in device would still work for some purposes (e.g. non-merging droplets, reactions not sensitive to time), but the time that it would take for each droplet to merge can have a wider distribution, since the droplets to be merged can end up closer to one another in some pooling wells and on different sides in other pooling wells. Then, with a regular array of droplets, in traps, in pooling wells, merging with the next set of droplets being dropped-in becomes more synchronized across the entire device.

Also, this regular array could be beneficial for automated imaging. In this device, these traps are located closer to the side of the reactor well that will first come in contact with the loading well, to maximize the likelihood of the droplet to be deposited into the trap. An example of this is shown in FIGS. 6A and 6B.

Figure 6A:
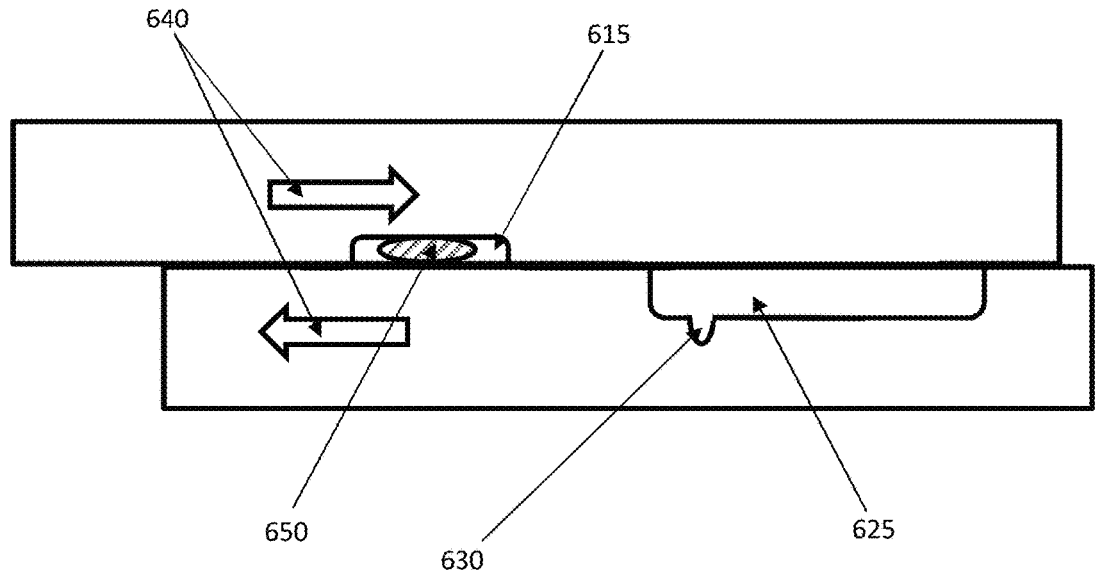
FIGS. 6A and 6B show an example of a trapping well.

FIG. 6A shows two plates that can slide (arrows 640 showing relative direction of sliding), where a droplet (650) has been loaded in a loading well (615).

Figure 6B:
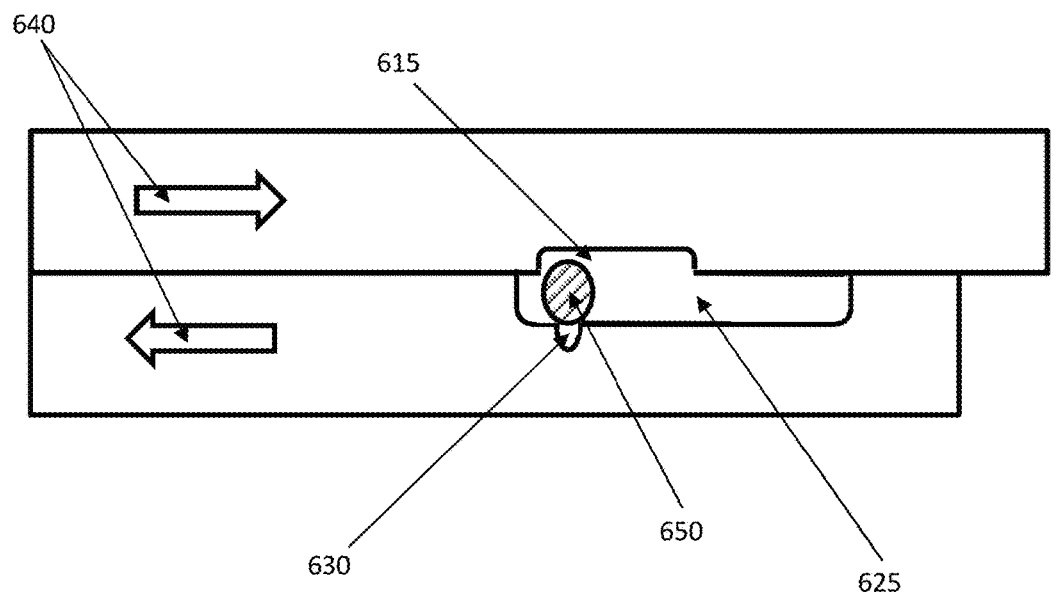

FIG. 6B shows, after the slide, the droplet (650) being dropped-in from the loading well (615) to the pooling well (625). A trapping well (630) holds the droplet (650) in place. Example dimensions include a 100 µm pooling well (625), a 50 µm loading well (615), and a 70 µm trapping well (630).

The use of a change in depth to anchor a droplet is generally explained in "Rails and anchors: guiding and trapping droplet microreactors in two dimensions" by Paul Abbyad et al. (Lab on a Chip, Issue 5, 2011)[4] and "Trapping Microfluidic Drops in Wells of Surface Energy" by Remi Dangla et al. (Physical Review Letters 107, 2011)[5], both of which are incorporated by reference herein. As used in the configuration shown in FIGS. 6A and 6B, the trapping wells help with localization of the droplet in the pooling well, which in turn helps for synchronized merging (i.e. merging/reactions occurring in different pooling wells at nearly the same time).

Some examples of trap well depths: 100 µm deep pooling well, 70 µm deep trap, 50 µm deep loading well; 100 µm deep pooling well, 70 µm deep trap, 40 µm deep loading well; 120 µm deep pooling well, 50 µm deep trap, 40 µm deep loading well; and 200 µm deep pooling well, 70 µm deep trap, 60 µm deep loading well.

Figure 7A:
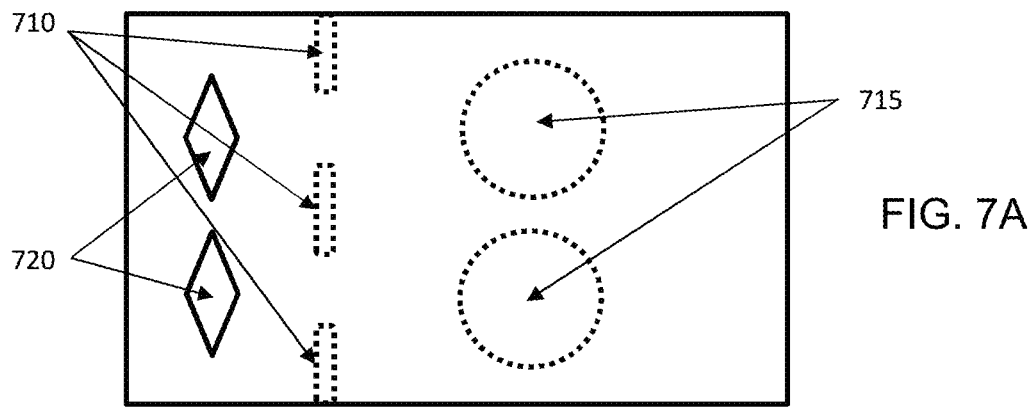
FIGS. 7A-7D show an example of the device with non-contiguous channels.
Figure 7B:
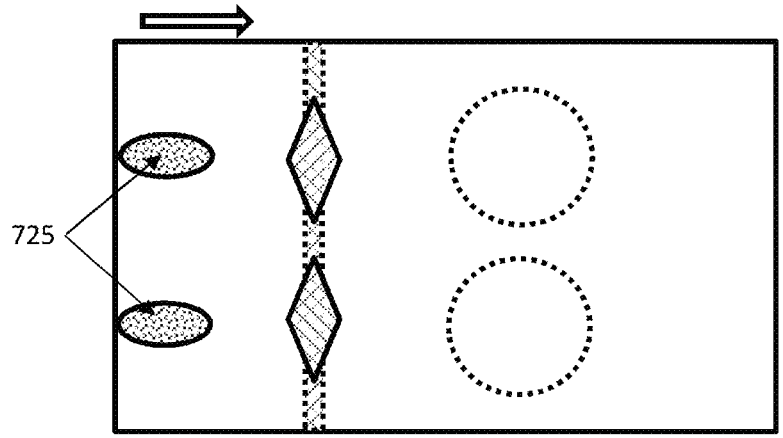
Figure 7C:
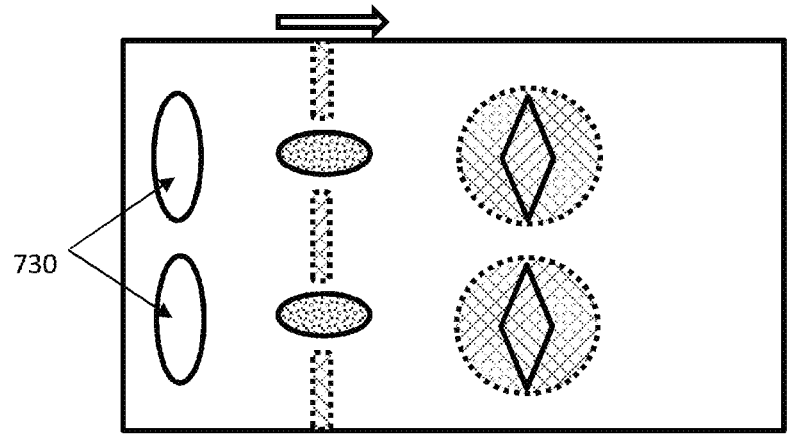
Figure 7D:
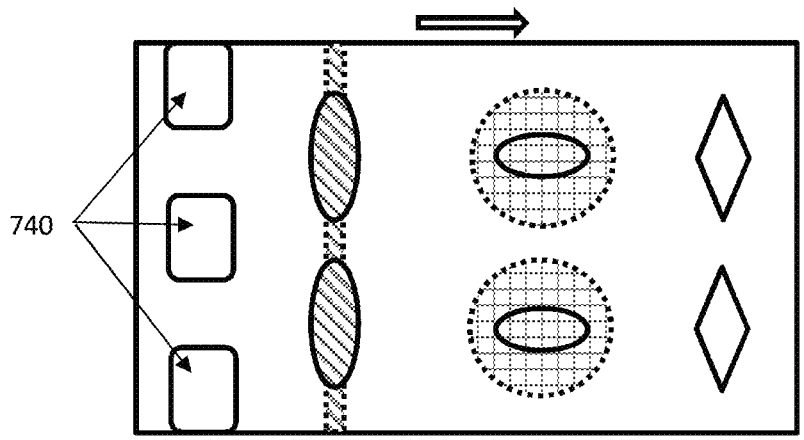

In some embodiments, the channels can be non-contiguous, allowing selective access to wells. FIGS. 7A-7D show an example of a non-contiguous loading channel (710). In one plate (dotted lines), the pooling wells (715) and non-contiguous loading channel (710) are aligned with the channel-loaded loading wells (720) of the other plate (solid lines). The alignment allows the loading channel (710) to load the channel-loaded loading wells (720) when the plates are slid to the position shown in FIG. 7B. Behind the channel-loaded loading wells (720) are pre-loaded loading wells (725). Since these wells do not need, nor want, contact with the loading channel (710), their geometry is narrowed to allow sliding past the channel without contact, as shown in FIG. 7C. A further set of channel-loaded loading wells (730) follow the pre-loaded wells (725), allowing a re-use of the loading channel (710) for supplying material, eventually, into the pooling wells (715). This being the final additive step of the example, the sequence ends with an elution channel (740), in this case also being non-contiguous, for flushing out the final product from the pooling wells (715).

The additive nature of the device can be seen in the example device shown in FIGS. 8A-8F. A channel-loaded loading well (820) is loaded with a non-merging droplet (841) from the loading channel (810), as shown in FIG. 8A. The plates are slid to the position shown in FIG. 8B, such that the first droplet (841) is dropped-in the pooling well (815). The plates are slid back, as shown in FIG. 8C, so that a second droplet (842) can be loaded into the loading well (820). The plates are slid back to position the loading well (820) over the pooling well (815), as shown in FIG. 8D, such that the second droplet (842) is dropped-in into the pooling well (815) with the first droplet (841). The sliding back-and-forth is repeated until additional droplets (843) are added to the pooling well (815). The droplets (841, 842, 843) can then by combined by, for example, the application of heat or by cycling temperatures (freeze/thaw) or by the addition of a demulsifying agent or by other mixing methods, creating a mixture of the contents of the droplets (850). This example shows the mixing being done while the loading well (820) is aligned over the loading channel (810), but in other embodiments the mixing can occur when the loading well (820) is positioned elsewhere, such as over the pooling well (815).

For some applications it is desirable to have the option to load and un-load sample into device before proceeding with the entire experiment. For example, the device as-shown can be recovered at any step before addition of the barcoded adaptors into the pooling wells. This obviates taking the device apart, cleaning, re-spotting, and re-assembling if samples that already have been dropped into the pooling wells do not need to be barcoded. To unload the pooling wells, the user needs to align the pooling wells with the recovery channels, pull the contents of the resulting fluidic path with either positive pressure, negative pressure, or both. After that, the fluidic path can be filled with carrier fluid again (e.g. PDMS oil). To have this type of complete non-wetting fluid evacuation, including the droplets that are located in the traps in pooling wells, the depth of the evacuation channels needs to be similar to the depth of the pooling wells. Some examples of depths: 100 µm pooling wells, 70 µm trap wells, 100 µm evacuation channels; 100 µm pooling wells, 70 µm trap wells, 120 µm evacuation channels; 80 µm pooling wells, 50 µm trap wells, 120 µm evacuation channels; 100 µm pooling wells, 50 µm trap wells, 100 µm evacuation channels; and 120 µm pooling wells, 80 µm trap wells, 120 µm evacuation channels.

Figure 9:
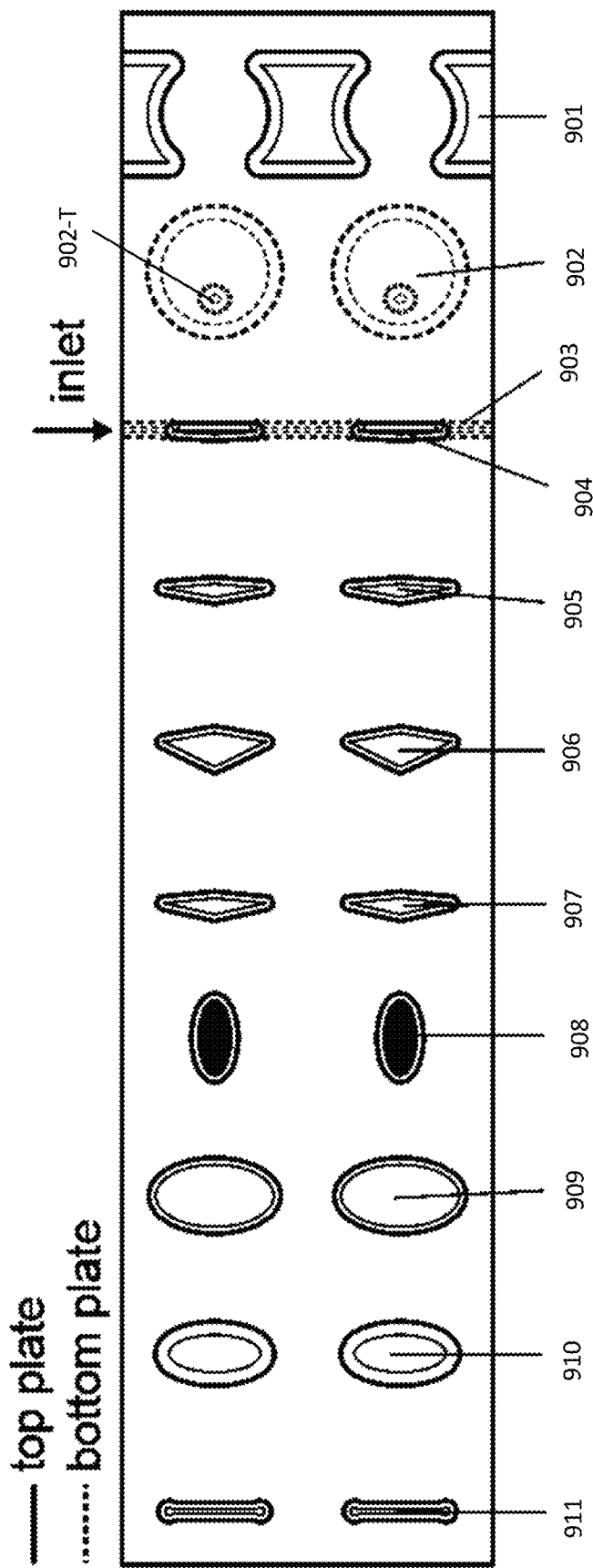
FIG. 9 shows two rows of an example device.

FIG. 9 shows two rows of an example device having multiple channel-loaded loading wells and an unloading channel. One plate contains the pooling wells (902) and loading channel (903). The pooling wells (902) also contain trapping wells (902-T). The other plate (typically the top plate) contains all the other channels and wells. Positioned behind the pooling wells (902) is a special elution channel (unloading channels) (901) that is only used if there was a mistake in any addition into the pooling well (902), e.g. an incorrect concentration of cells used from the cell loading wells (903). The first set of loading wells is the cell loading wells (903) to drop-in the initial cells to the pooling wells (902). In succession beyond the cell loading wells (903), in the order the loading channel (903) will encounter them as the plates are slid, are the lysis/extraction buffer loading wells (905), the 3'-end repair solution loading wells (906), the denaturing agent loading wells (907), the pre-dried reagent pre-loaded loading wells (908) (e.g. adapter wells), the ligation mix loading wells (909), and the PEG-rich solution loading wells (910) used for ligation reaction. Note that the pre-dried reagent pre-loaded loading wells (908) are configured to avoid contact with the non-contiguous loading channel (903). At the end of the row are elution channels (911) which are used with the loading channel (903) to allow cleaning of the loading channel (903), if needed. The loading channel (903) is etched less deeply than the wells so that the aqueous phase preferentially occupies the wells and gets pinched off by oil, thereby ensuring a more complete filling of the wells during loading. The wells are spaced such that when one set of loading wells is being loaded by the loading channel, another set of loading wells is dropping-in into the pooling wells, thereby eliminating extra sliding steps.

Figure 10:
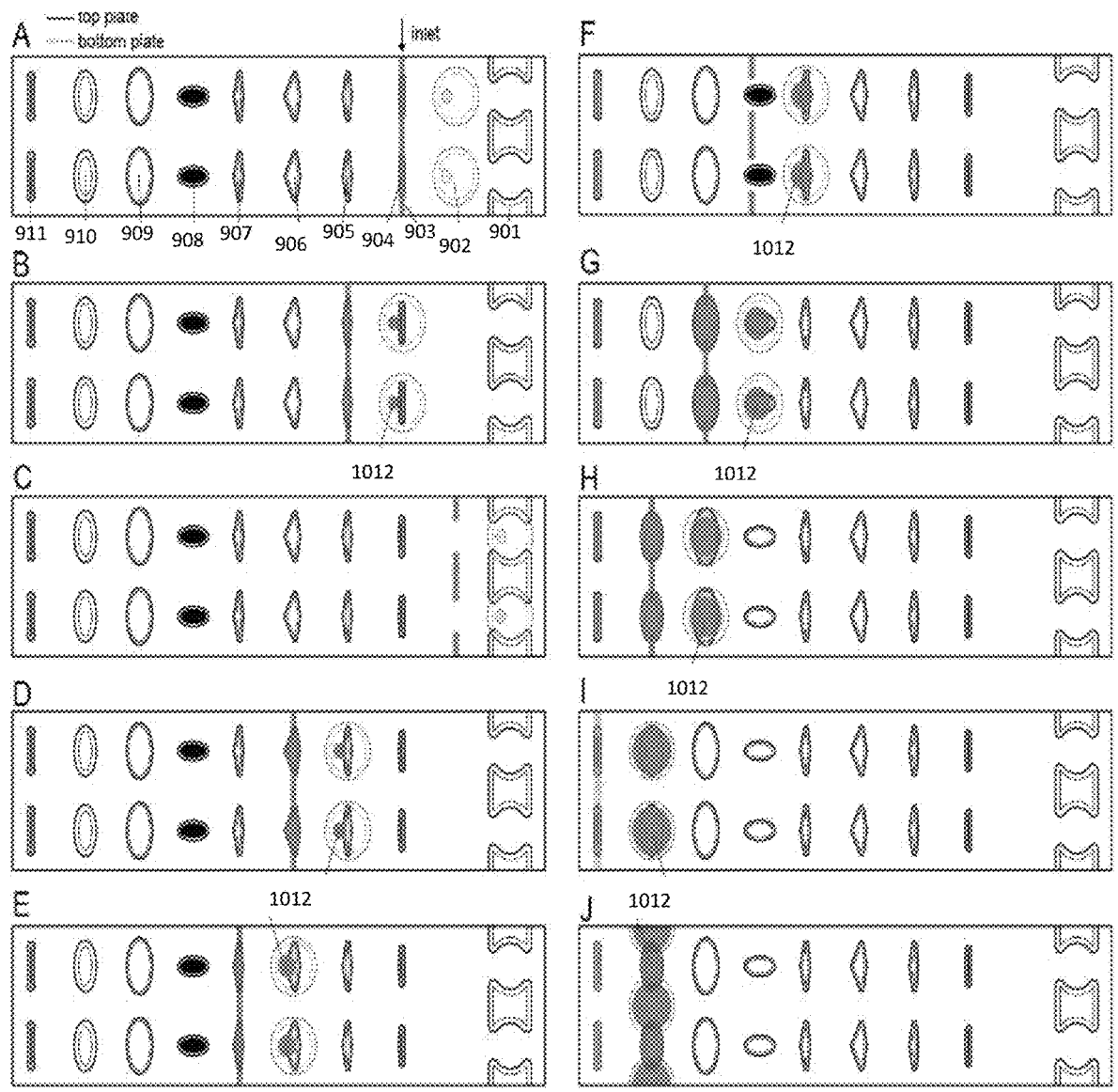
FIG. 10 shows progressive sliding of the device of FIG. 9.
Figure 30:
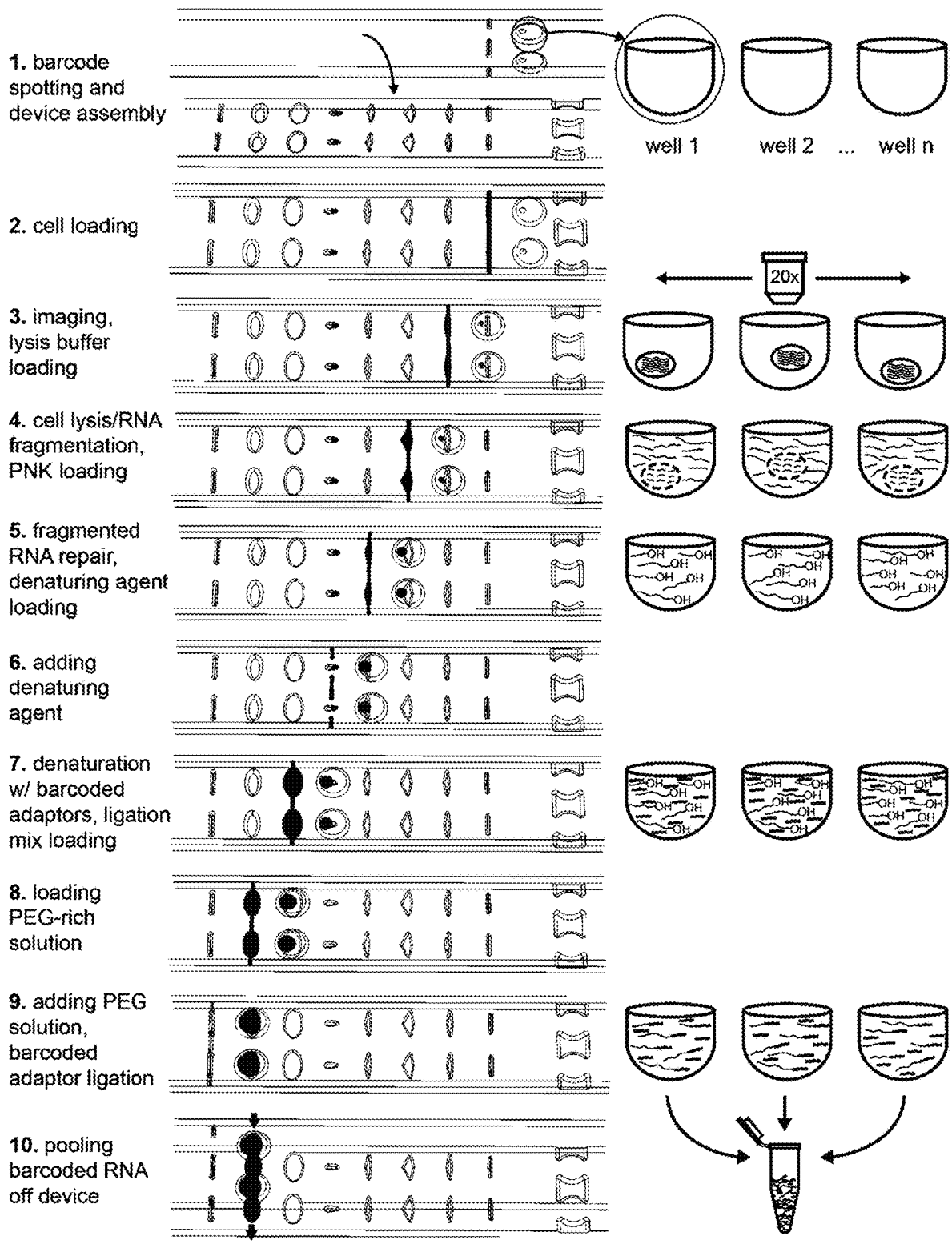
FIG. 30 shows a schematic illustrating an exemplary use of the progressive sliding method of FIG. 10.

The succession of steps for the device shown in FIG. 9 is shown in FIGS. 10 and 30. (A) cell loading step, cell wells (904) are connected with channels (903); (B) cells in wells (904) are dropped into the pooling wells (902) and lysis buffer wells (905) are aligned (and optionally loaded) with the loading channels (903); (C) if, after loading cells the device needs to be recovered (e.g. in case of cell overloading), the top plate can be slipped (slid) left to connect the pooling wells 2 with unloading channels (901). Then, the contents can be retrieved using negative relative pressure, and the wells (902) and channels (901) re-loaded with carrier fluid (e.g. oil). Then, the top plate will need to be slipped back into conformation B and lysis buffer loaded into wells (905); (D) lysis buffer, previously loaded into wells (905) in plate conformation B is dropped into wells (902) and mixed with cell-containing droplet (912) already present in wells (902).

The device can be incubated/heated to a temperature prescribed by specific protocol to lyse cells. Wells (906) are aligned with connecting channels (903) in this conformation, and the 3'-end repair solution (e.g. polynucleotide kinase) can be loaded into wells (906); (E) 3'-end repair solution is dropped into wells (902), mixed with droplet (912), and the device is incubated (e.g. 37C for 40 min). Wells (907) are aligned with loading channels (903) in this conformation, and the denaturing agent (e.g. dimethyl sulfoxide) can be loaded into wells (907); (F) denaturing agent is dropped into wells (902) and mixed with droplet (912), In this conformation, loading is not necessary because the barcoded adaptors are pre-dried in wells (908); (G) pre-dried barcoded adaptors in wells (908) are delivered to wells (902) by slipping the top plate, are dissolved in droplet (912), and the device is incubated (e.g. 65C for 2.5 min).

After the device is placed on ice immediately after to prevent re-forming of secondary structures of RNA fragments. Wells (909) are aligned with loading channels (903) in this conformation, and the ligation mix can be loaded into wells (909); (H) Ligation mix is dropped into wells (902) and mixed with droplet (912). Wells (910) are aligned with loading channels (903) in this conformation, and the PEG-rich solution can be loaded into wells (910); (I) PEG-rich solution is dropped into wells (902) and mixed with droplet (912). The device can be incubated long enough for ligation to take place (e.g. overnight at room temperature). Channels (911) are aligned with loading channels (903) in this conformation, so that the user can take out left-over contents of channels (903) if desired.

The device can be optionally frozen in this conformation to preserve samples as well; (J) when user is ready to proceed with cDNA library preparation, the top plate can be slipped up, so that pooling wells (902) and wells (910) form a continuous channel. The contents of this channel can be eluted using positive or negative pressure (or both). The separate droplets (912) in this step merge (pooling). Note that the wells and channels are all spaced such that when the loading channel (903) is loading a set of loading wells, another set of loading wells is positioned to drop-in to the pooling wells (902), thereby allowing more efficient use of each slip.

Figure 31:
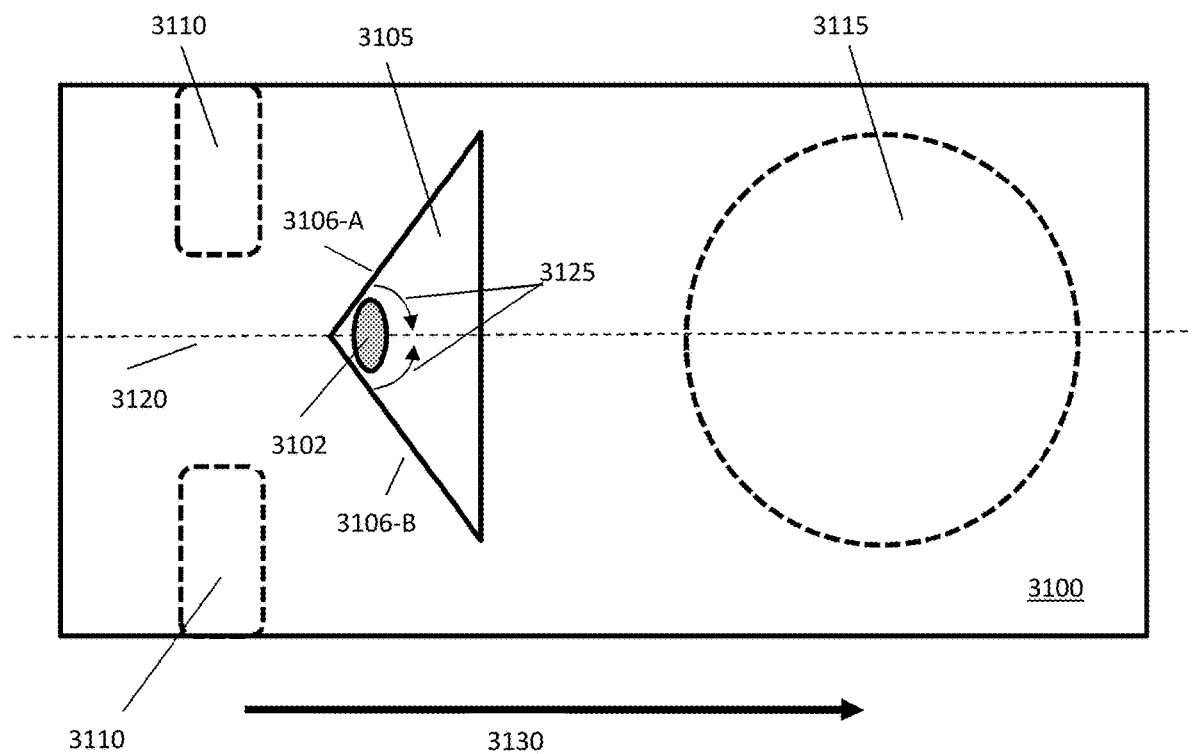
FIG. 31 shows a schematic illustrating an exemplary use of an angled channel-loaded loading well in a device with hydrophobic surfaces.

In some embodiments of the device, the loading wells cannot get filled completely, and the volume of the non-wetting sample inside these wells may not be in a single droplet. Transferring and merging multiple droplets of a reagent can cause some delays in merging time. Channel-loaded loading wells can be shaped to make it more energetically favorable for the droplet to pinch off in the center of the well after external pressure is removed (e.g. from micropipette) and the fluid flow for loading is stopped. If multiple droplets do form, the loading wells are designed to scoop these droplets toward the center of the loading wells as the slipping is performed. The centers of the loading wells are aligned with the traps inside the pooling wells, where the reagents get delivered and merged. FIG. 31 shows an example of using an angled channel-loaded loading well in a device with hydrophobic surfaces on both plates. The plates (3100; top view—top plate features in solid lines, bottom plate features in dashed lines) each have a hydrophobic surface, meaning any droplets in the wells (3105, 3115) and channels (3110) are non-wetting to the surfaces. The plates in use would be slid, top plate to bottom plate, in a relative direction (3130) from the loading channel (3110) to the pooling well (3115), perpendicular to the loading channel. The loading well (3105) is shaped to have a side, with two walls (3106-A and 3106-B), opposite the pooling well (3115) such that a bisector (3120) of the loading well (3105), parallel to the relative direction of sliding (3130) of the top plate (3100), is at an angle (3125) to each of the walls (3106-A and 3106-B) that is less than 90 degrees (i.e. the walls do not form a straight line). This allows the non-wetting droplet (3102) carried by the loading well (3105) remain in the center of the loading well despite the hydrophobic surfaces (which, without the angled walls, could be non-centered and/or divided into multiple droplets). This allows accurate delivery to the pooling well (3115) along the bisector (3120). The angles of the walls from the bisector can be any angle less than 90 degrees, preferably between 10-87.5 degrees, depending on other size and shape constraints of the wells. Example angles include 87, 80, 64, and 77.5 degrees.

Figure 32A:
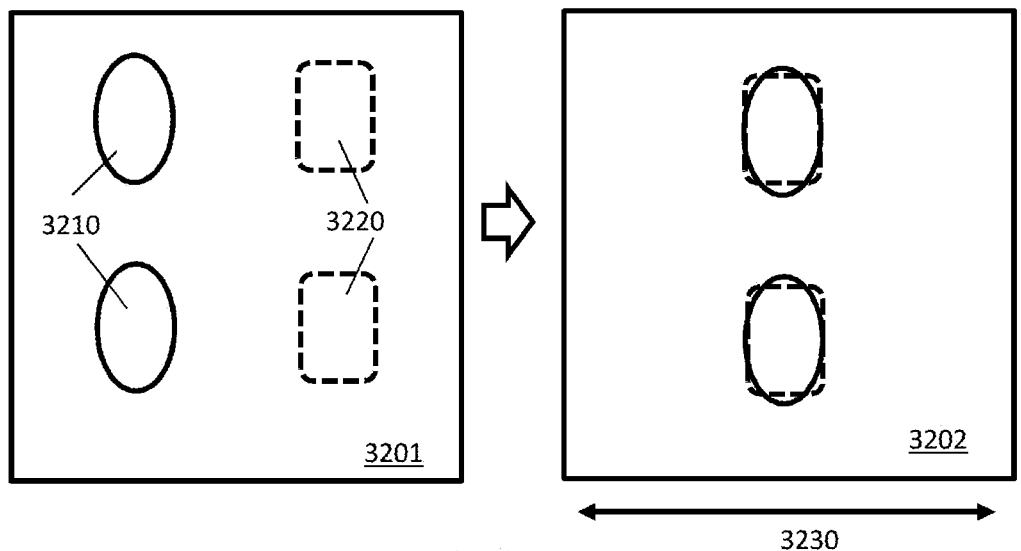
FIGS. 32A and 32B show an example of having chambers acting as both wells and channels, depending on the slip direction.
Figure 32B:
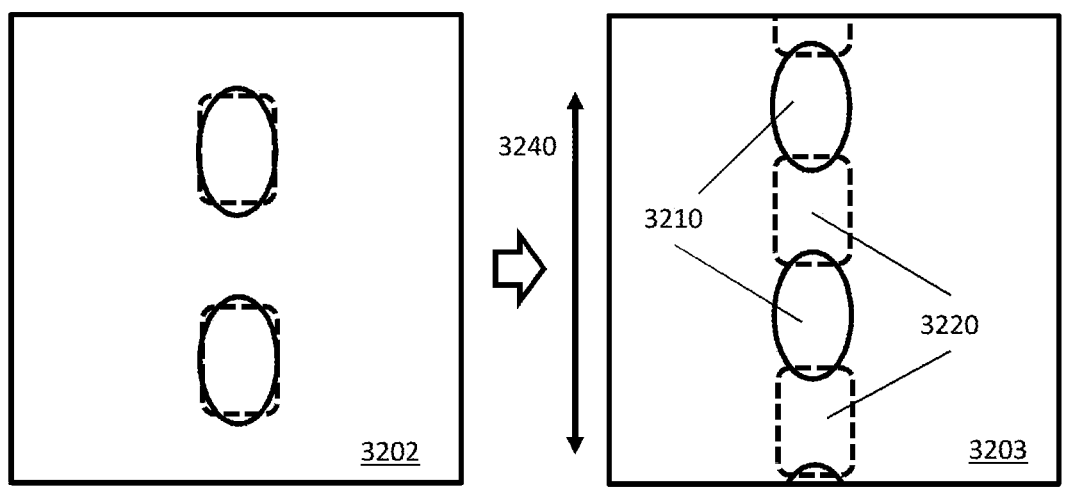

FIGS. 32A and 32B show an example of having chambers acting as both wells and channels, depending on the slip direction. FIG. 32A shows plates in one relative position (3201) with separate sets of wells, one set on the top plate (3210, solid lines) and one set on the bottom plate (3220, dashed lines). The plates are slid in one direction (3230) resulting in a new relative plate position (3202) with the wells overlapping, allowing for drop-in from one set of wells to the other. FIG. 32B shows the plates starting from the drop-in position (3202), slid perpendicularly to the first sliding direction (3240) resulting in a different relative plate position (3203) where the two sets of wells (3210 and 3220) are now configured to allow one set of the wells to act as a channel to load the other set of wells (depending on relative well depths).

Devices herein described allow performance of reactions with increased efficiency with respect to approaches performed off device. In particular, the devices together with the methods described herein allow for barcoding and subsequent analysis of nucleic acids from viruses, phages, single cells, group of cells, multiple cells, and tissues. The cells can be taken directly from a culture, or indirectly from a clinical sample, including samples in which host cells possibly have pathogens inside them.

For example, the devices herein described allows for a barcoding for a subsequent full-length strand-specific sequencing of all classes of RNA from any species including eukaryotes and prokaryotes in a multiplex manner. For example, the devices herein described allows for a barcoding for a subsequent analysis of dozens to several thousands of independent nucleic acids samples simultaneously.

In some embodiments, the devices herein described allows for efficient nucleic acids extraction from single eukaryotic cells, cells nuclei, single prokaryotic cells, and their efficient barcoding without a need in the presence of (poly)A-tails, in multiplex format. For example, a device (similar to what is shown in FIG. 9) can be arranged wherein one plate has pooling wells and a loading channel, and the other plate has at least two sets of channel-loaded loading wells (one set for channel-loading and dropping-in an extraction buffer, the other set for channel-loading and dropping-in a ligation mix) and a set of adapter wells, the adapter wells each being pre-spotted with a unique barcode of tags.

The device can be slid into a first position where the first set of loading wells gets loaded with extraction buffer (or digestion buffer) by the loading channel. The device can then be slid to a second position where the first set of loading wells can drop-in the extraction buffer to the pooling wells, thereby allowing extraction of any nucleic acid that might be in the pooling well. The plates can then be slid into a third position where the adapter wells can drop-in the adapters to the pooling wells, such that each pooling well gets a uniquely identified (barcoded) adapter. This maintains identification of the nucleic acid to its origin even after removal from the device. Optionally, the loading channel can be made non-contiguous to allow the adapter wells to slide past the loading channel without contamination from the loading channel. Then the second set of loading wells can be loaded with ligation mix. This can be done while the device is in the third position (if the well spacing is configured as such) or in a different position. The plates are then slid to a fourth position to allow the ligation mix to drop-in the pooling wells. Since the adapters are already in the pooling wells, this allows ligation of the adapters to any nucleic acid in the wells to occur in-device.

Note that herein, the use of "first", "second", "third", etc. just signify that the elements are different from each other—it does not imply a temporal or spatial order of the elements. For example, the third position of the plates might be a position between the first and second positions.

In some embodiments, the device can be used in a method for ligating an adaptor to nucleic acid by loading the first set of channel-loaded loading wells with cells or biological sample and sliding the first plate and the second plate to the second position and dropping-in the cells or biological samples from the first set of channel-loaded loading wells to the pooling wells; loading the next set of channel-loaded loading wells with an extraction buffer through the loading channel and sliding the first plate and the second plate to the next position and dropping-in the extraction buffer from the first set of channel-loaded loading wells to the pooling wells; performing incubations at optimal temperatures, to extract and/or fragment nucleic acids; sequentially loading the next sets of channel-loaded loading wells with reaction mixtures to prepare for ligation (e.g. reparation mixture, denaturation mixture) through the loading channels and sliding the first plate and the second plate to the next positions and dropping-in the conditioning mixtures from the channel-loaded loading wells to the pooling wells; performing incubations at optimal temperatures; sliding the first plate and the second plate relative to each other to combine (or dropping-in) the adapters from the adapter wells to the pooling well; performing incubations at optimal temperatures; loading a set of channel-loaded loading wells with ligation mix through the loading channel and sliding the first plate and the second plate relative to each other to a the ligation position, such that the second set of channel-loaded loading wells are aligned in a one-to-one correspondence with the pooling wells and dropping-in the ligation mix from the second set of channel-loaded loading wells to the pooling wells, while the at least two pooling wells contain both the nucleic acid and corresponding adapters.

In some embodiments, the devices herein described allows for efficient and multiplexed nucleic acids extraction and barcoding for subsequent full-length strand specific (poly)A independent single cell RNA seq applicable for eukaryotic cells, cells nuclei, single prokaryotic cells, in multiplex format. It is possible because of nucleic acids extraction and fragmentation can be performed at desired buffers with detergents and chelating agents, and at desired temperatures. At the next step reagents can be added that compensate for the previous buffers and dilute them, and use other desired temperatures. Each time the identity of the nucleic acids from the original sample is tracked geometrically through the whole workflow, and, finally, is tracked chemically after barcoding through RNA-RNA ligation.

In some embodiments, of a full-length strand-specific sequencing performed in a multiplexed manner with device and methods of the description, the nucleic acids from one cell and more can be barcoded. The barcoded nucleic acids can originate from prokaryotic cells, eukaryotic cells or cells infected by a phage or virus. The analyzed nucleic acids cells can originate from more than one type of cells, including but not limited to host and parasite, immune cell and a pathogen, mammalian cells and co-habiting bacterial or fungal cells. The barcoded nucleic acids can be prepared for transcriptome analysis, such as by multiplexed RNA sequencing. The barcoded nucleic acids can be prepared for genome analysis, such as by multiplexed DNA sequencing. The barcoded nucleic acids can be prepared for specific nucleic acids quantification performed by nucleic acid amplification including PCR, or isothermal nucleic acid amplification.

In some embodiments, of strand-specific sequencing performed with device and methods of the description, the barcoded nucleic acids are analyzed for their DNA sequences, which can determine the origin of a species in cases of bacteria, fungi, virus or other infectious agents. The barcoded nucleic acids can be analyzed for DNA and RNA mutations including insertions, inversions, deletions, point mutation, copy number variants, duplications, translocations, and many other known genetic events and changes. The barcoded nucleic acids can also be analyzed for RNA sequences, for gene expression profiling, RNA isoforms, and for repeat expansions, In some embodiments, of strand-specific sequencing performed with device and methods of the description, the barcoded nucleic acids are analyzed for detecting the changes in DNA and RNA in response to a stimulus of interest, including but not limited to antibiotics.

In some embodiments of strand-specific sequencing performed with device and methods of the description, barcoded nucleic acids can be obtained with a method and/or system described in US Application having Ser. No. 16/141,901 entitled "Methods and systems for performing single-cell analysis of molecules and molecular complexes" filed on Sep. 25, 2018 with and incorporated herein by reference in its entirety.

In particular, in those embodiments, a microfluidic device is described for isolating cells or organelles thereof into a plurality of single cells or single organelles for in-cell or in-organelle barcoding. In those embodiments device typically comprises: a first plate comprising a first surface; and a second plate with a second surface, the first surface in contact with the second surface; the first plate having on the first surface a loading channel and pooling wells; the second plate having on the second surface loading wells; wherein the loading wells are configured to be aligned in a one-to-one correspondence with the pooling wells, and the loading wells have a smaller volume than the pooling wells.

The device for isolating cells or organelles thereof into a plurality of single cells or single organelles for in-cell or in-organelle barcoding herein described can also comprise: surface energy traps (i.e. deeper portions) in the pooling wells; the loading wells having a greater depth than the loading channel; and/or the channel-loaded loading wells each having a side opposite a direction from the loading channel to the pooling wells the direction perpendicular to the loading channel, the side comprising two walls at equal angles from a bisector of the each channel-loaded loading wells parallel to the direction from the loading channel to the pooling wells, the equal angles each being less than 90 degrees.

Figure 33:
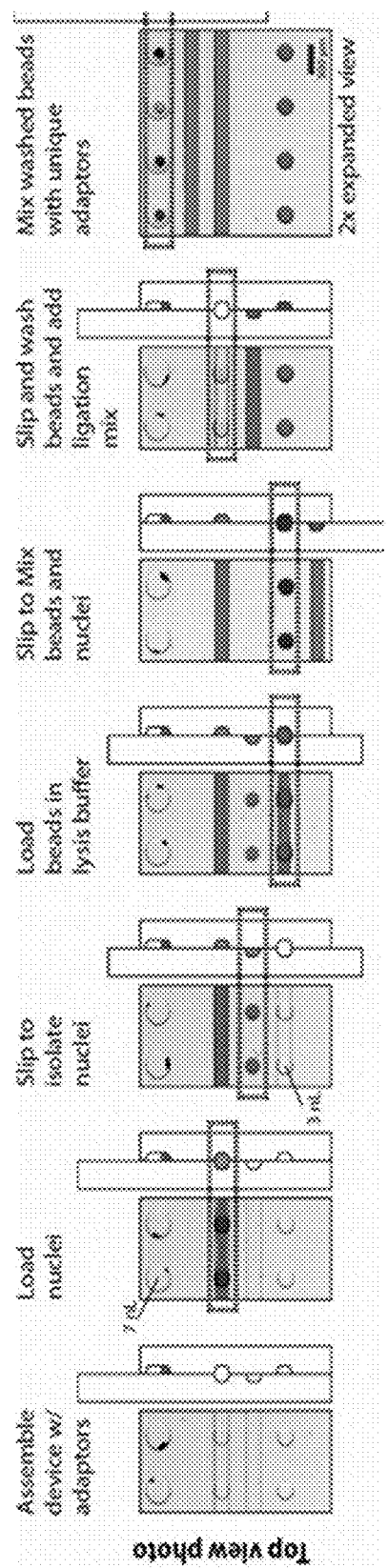
FIG. 33 shows a schematic illustrating an exemplary SlipChip device suitable for performing single cell nucleus specific barcoding. The device shown in the schematic illustration of FIG. 33, has four different programmed positions in which all required procedures can be completed. Unique adapters are spotted deterministically on the device prior to assembly.

An additional exemplary device for additive delivery configured to perform methods herein described wherein the barcoding is performed on isolate single-cells or isolated single organelle, is shown in FIG. 33. The exemplary device of FIG. 33 incorporates four different positions: two are used for loading; two are used for mixing loaded solution. In the exemplary device of FIG. 33, the user is able to visually confirm and image the loading of single nuclei, and relate sequenced results back to a specific device and compartment. The ability to relate sequenced results back to a specific well on a specific device is due to the ability to robustly and deterministically spot a precise amount of adapters onto a SlipChip device prior to assembly. This configuration is therefore advantageous compared with alternative single-cell microfluidic techniques. This configuration can also be beneficial when validating a sequencing dataset as cell loading is Poisson based, and results can be confirmed to come from a single cell as opposed to multiple.

In some embodiments, of strand-specific sequencing performed with device and methods of the description, the target organisms are enriched by pre-incubation on device.

In some embodiments, of strand-specific sequencing performed with device and methods of the description, the target organisms are pre-conditioned by pre-incubation on device.

In several embodiments, using the device provides microfluidic mixing of reagents in the additive manner, that allows various appropriate buffers and various appropriate temperature conditions (often exclusive at each step or incompatible between steps). The device can serve as a tool to perform step by step reactions, when each reaction requires unique reagents and temperature conditions. In particular the device allows efficient performance of the first reaction (e.g. sample or single cell lysis) and every downstream reaction (e.g. nucleic acids repair, denaturation, ligation, amplification, barcoding), providing a multi-step workflow without intermediate clean ups.

Additional details of strand-specific sequencing performed with device and methods of the description are reported in Examples 3-5 of the instant disclosure.

EXAMPLES

The devices, methods and system herein disclosed are further illustrated in the following examples, which are provided by way of illustration and are not intended to be limiting.

Example 1-Single Cell Nuclei Preparation

The nuclei were passed through a 25 g needle 5× and then strained through a 10 μm filter. Nuclei were counted on a C-chip: concentration of 120 nuclei/μL.
On device calculations:
Overall device layout: 48 wells with each well (ideally) containing 3.3 nL per well
Total volume over 48 wells: 158.4 nL
Loading at 30% occupancy-aiming for 14.4 cells over 158.4 nL→concentration of cells to load=90.91 cells/μL
Made a 10 μL mixture containing cells, BSA, Evagreen, and water to load onto the device (see Table 1).

TABLE 1

|  | Initial Concentration | Final Concentration | Vol. (uL) to mix |
|---|---|---|---|
| Cells (dA tailed; cells/uL) | 120 | 90.91 | 7.58 |
| BSA (mg/mL) | 20 | 1 | 0.5 |

TABLE 1-continued

|  | Initial Concentration | Final Concentration | Vol. (uL) to mix |
|---|---|---|---|
| Evagreen (X) | 20 | 1 | 0.5 |
| H2O |  |  | 1.42 |
|  |  | Total | 10.00 |

Assembly of Device
  Two devices were used—each containing 34 adapters each pre-spotted in individual adapter wells. Upon assembly of both devices, all 34 adapters were still present.
  Device 1 had 23 clumps; device 2 had 10 clumps (majority of the clumps were single cells—about 10-15% consisted of 2-4 cell clumps).
Run Through of Device:
  With the device in the first alignment to load cells, the device was flushed through with 1×PBS, 1 mM EDgTA, 0.1% Triton, and 1 mg/mL BSA and then vacuumed out (to coat the glass walls of the device with BSA to limit cell sticking).
  Cell mixture described previously was then loaded and then slid in.
  After sliding and realigning for reloading, the device was flushed again with 1×PBS, 1 mM EDgTA, 0.1% Triton, and 1 mg/mL BSA solution and then vacuumed out.
  2× instant sticky mix was then flown through and then slid to mix with the cells/spotted adapters.
  Adapter ligation was performed for 6 hours at 25° C.
  Prior to unloading off the device, the unloading channel was flushed through with 1×PBS, 1 mM EDgTA, 0.1% Triton, and 1 mg/mL BSA solution.
  Device contents were unloaded into a microcentrifuge tube.
  Contents of device were washed twice with 1×PBS, 1 mM EDgTA, and 0.1% Triton solution prior to being coupled overnight at 6° C. at 1000 rpm to 100 µL of NHS beads (beads being washed with 1 M HCl and twice with 1×PBS) immersed in urea lysis buffer.
  After coupling, the beads were washed with M2 buffer before being quenched for 3 hours at 12° C. at 1000 rpm using 1 Mrpm using 1M Tris, 0.5 mM EDgTA and 0.1% Triton.
  After quenching, the beads were washed once with LoTrEe buffer before performing barcode ligation.

Example 2-Nuclei Ligation with Adapters

Figure 3A:
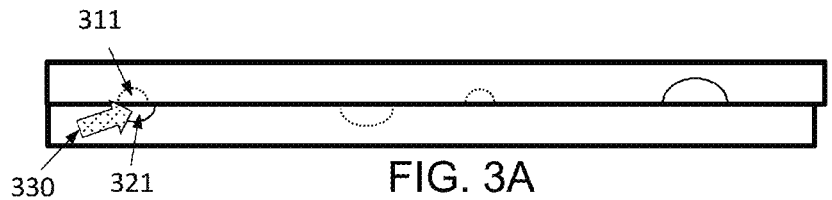
FIGS. 3A-3F shows an example use of an example (not to scale) device, shown in side (cross sectional) view.
Figure 3B:
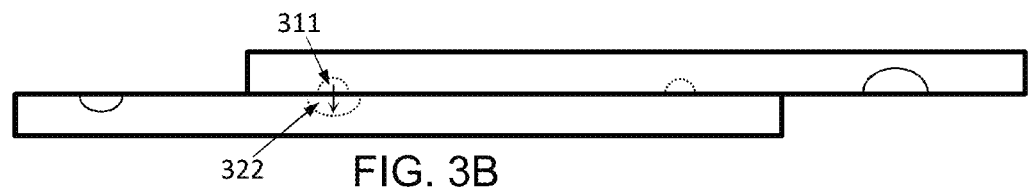

FIGS. 3A-3F show an example device (not to scale, for case of viewing) used for attaching adapters to DNA in individual nuclei, such that the nuclei remain isolated from each-other. In these figures, channels are shown in solid lines while wells are shown in dotted lines, regardless of plate. In FIG. 3A, the loading wells (311) are aligned over the loading channel (321). Note that "over" and "under" (or "top" and "bottom") are used with reference to the drawings, and the actual orientation will typically not matter as the driving forces are microfluidic and typically will not depend on the direction of gravity.

A solution containing individual nuclei is injected into the loading channel such that each loading well only has one nucleus. This can be done by Poisson distribution, or any other loading system. There is, of course, a trade-off of probability of having wells with multiple nuclei vs. number of wells effectively loaded. Once loaded, the device plates are slid to FIG. 3B, where the loading wells (311) are positioned over the pooling wells (322), with capillary action dropping the nuclei into the pooling wells.

Figure 3C:
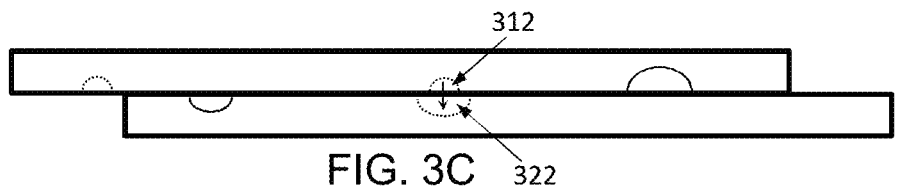

The device is then slid to a new position, as shown in FIG. 3C, where the adapter wells (312) are positioned over the pooling wells (322). In this case, instead of being loaded via a channel, the adapter wells (312) can be pre-spotted with adapters (optionally uniquely tagged adapters) which are then rehydrated by mixture with the contents of the pooling wells (322). Optionally, the use of adapter wells can be bypassed by pre-spotting the adapters directly into the pooling wells (322) instead. The adapters and the nuclei can be combined in the pooling wells (322) by mixing. Mixing can be performed by repeatedly inverting the device, or by magnetic mixing if the adapters are attached to magnetic beads, or by any standard microfluidic mixing technique.

Figure 3D:
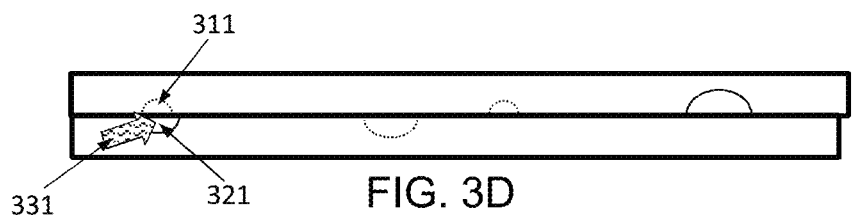

Once the adapters have been sufficiently mixed with the nuclei, the device is slid back to loading position, as shown in FIG. 3D. The loading wells (311) and loading channel (321) are cleaned, then the loading wells (311) are filled with a ligation mix (331). The ligation mix can be, for example, T4 ligase, Blunt/TA Ligase Master Mix, Instant Sicky-End Ligase Master Mix, RNA-ligase, etc.

Figure 3E:
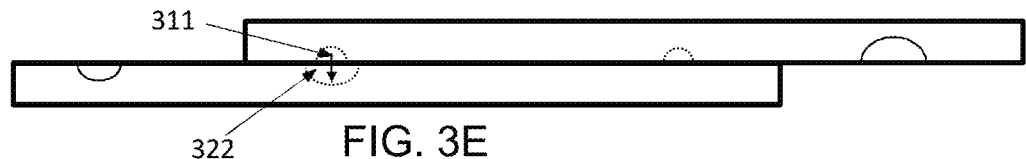

The device is slid again, as shown in FIG. 3E, such that the loading wells (311) are again aligned with the pooling wells (322), thereby allowing mixture of the ligation mix and the nuclei-adapter solution. Ligation proceeds as long as need be (e.g. 1, 2, 3, 4, 5, 6, 8, 10, 12, 16, or 20 hours).

Figure 3F:
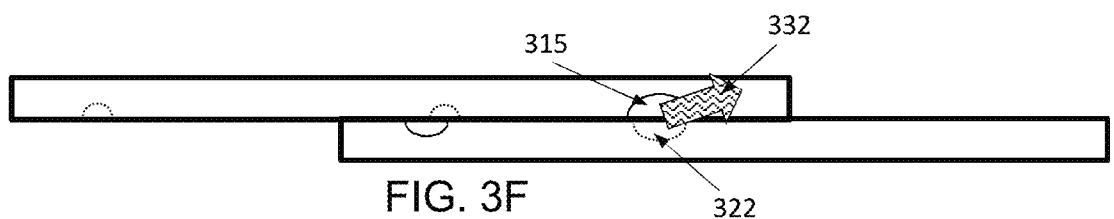

The device can be inverted at regular intervals to prevent settling. Once the ligation is complete, the device is slid to a new position, as shown in FIG. 3F, that aligns the pooling wells (322) with the elution channel (315). The elution channel (315) is flushed, thereby eluting the nuclei (now with attached adapters) out of the device, for further processing.

Figure 4:
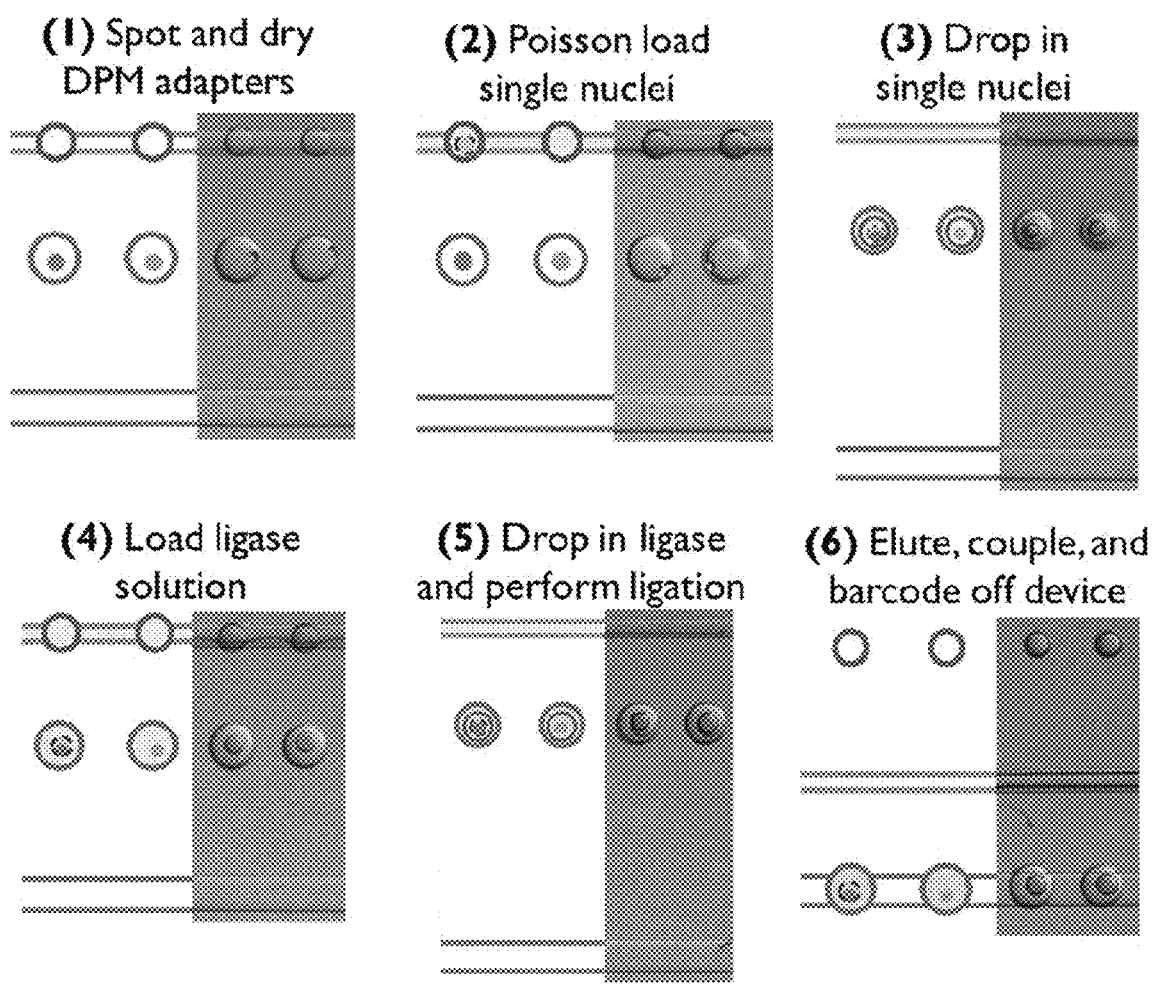
FIG. 4 shows ligation of a nucleus by the device, shown in top view.

FIG. 4 shows an example device (top view) for in-nuclei ligation of single nuclei. Single crosslinked nuclei are isolated stochastically on device, combined with pre-spotted adapters, then mixed with ligase mix (e.g. NEB Instant Sticky Mix). Nuclei are combined when eluted for downstream processing. This is similar to what was shown in FIGS. 3A-3F, except that in FIG. 4, the adapters are pre-spotted in the pooling wells, thereby eliminating the need for adapter wells.

Example 3: General Steps in Single-Cell Sequencing and Analysis of Nucleic Acids Using a Microfluidic Device of the Disclosure Organisms/cells are loaded to device in a solution containing surfactants. The organisms/cells can be loaded to the device in specific media. For example, the organisms/cells can be loaded to the device in a solution containing additives promoting their growth. The solution can also contain additives accelerating the response to a stimulus of interest and/or additives casing the subsequent nucleic acids extraction. The solution can also be a buffered solution.

The organisms/cells loaded to device can be incubated for a time from at least one minute to 15 minutes or more. In particular, the incubation time can be from 5 minutes to 10 minutes, from 10 min to 15 minutes or longer than 15 minutes.

The organisms/cells loaded to device can be incubated at the temperatures possible to have for these organisms under their environmental/physiological conditions, as well as under the artificial conditions of interest. The temperature can range from about 0° C. to about 80° C. In particular, the incubation temperature can range from about 0° C. to about 5° C., 5° C. or above, 10° C. or above, 15° C. or above, 20° C. or above, 35° C. or above, 40° C. or above, 65° C. or above, or 80° C. or above.

The organisms/cells loaded to device are then moved into a mixing well. In the mixing well, the organisms/cells loaded to device are mixed with extraction buffer. The extraction buffer contains surfactants (e.g. BSA). The extraction buffer can contain non-ionic detergents such as Triton™ X-100, Nonidet™ P40, Tween™ 20, and/or reagents stabilizing PH (such as Tris-HCl), chelating agents (such as EDTA), salts (such as KCl, LiCl), RNA protection agents (such as DTT, TCEP, beta2Mercaptoethanol, commercial RNAses inhibitors), and/or lysozyme. The extraction buffers can be commercially available (e.g. from Lucigen™, Bio-Rad™, Zygem™). In one experiment, the cells were mixed with extraction buffer containing 100 mM Tris PH8. The organisms/cells loaded to device mixed with extraction buffer are exposed to a temperature incubation (such as 37° C.+/−4° C. 72° C.+/−2° C., or 95° C.+/−5° C.) for the time ranges starting from few seconds, >1 min, >2 min, >3 min, >4 min, >5 min, and up to >30 min.

The extraction buffer can be loaded to device and combined to the organisms/cells loaded to device in a mixing well.

The nucleic acids from the organisms/cells loaded to device and mixed with extraction buffer can be fragmented, for example, using temperature such as 91° C. for RNA, using divalent cations, using enzymatic fragmentation both for DNA and RNA, using short-time amplification, using limited length amplification-such as posing inhibitors for amplification linger than desirable length, or using ultrasound.

The nucleic acids from organisms/cells loaded to device can also be mixed with variable types of the next "repair" solution and are end-repaired for subsequent ligation step such as to restore their 3'OH groups.

The repair solution can contain surfactants such as BSA, RNA protecting agents such as DTT, RNAses inhibitors, enzymes adding or removing phosphates (e.g. phosphatases, or kinases—such as T4 PNK). The solutions mixed for repair of nucleic acids from organisms/cells loaded to device can compensate for the components introduced from the previous steps. For example, EDTA from extraction buffer can be compensated by $Mg^{2+}$.

The nucleic acids from organisms/cells loaded to device can be incubated for a time period of 1-40 minutes and at a temperature range of 37° C.+/−3° C. for repair.

The repair solution can also be loaded to device and combined to the nucleic acids extracted from the organisms/cells loaded to device in a mixing well.

The nucleic acids from organisms/cells loaded to device are then mixed with denaturing agents (variable types of denaturing solutions) and are exposed to denaturing conditions in a presence of barcoded adaptors (e.g. adding DMSO to final concentrations of about 10%, 15%, 20%, 25% to about 65%). The denaturing solution may contain surfactants such as BSA.

The denaturing solution can be loaded to device and combined to the repaired nucleic acids extracted from the organisms/cells to loaded device in a mixing well.

In some examples, the wells containing the barcoded adaptors are also combined with a mixing well, containing the repaired nucleic acids extracted from the organisms/cells and a "denaturing" solution, so barcodes and nucleic acids are denatured together An immediate cooling down (e.g. placing devices on ice) can be followed after denaturation.

The nucleic acids from organisms/cells loaded to device and barcoded adaptors (either DNA or RNA adaptors, single or double stranded, optionally in a form of DNA/RNA heteromers) are covalently connected to the extracted nucleic acids, using variable types of a linking solution. At this step, barcoded adaptors are directly connected to the extracted nucleic acids.

In some examples, a poly A RNA is targeted by reverse transcription primer directly, containing poly T sequence, barcode, and a part of sequencing adaptor.

The linking solution may contain surfactants such as BSA.

In some examples, nucleic acids from organisms/cells loaded to device and barcoded adaptors are covalently in ligation reaction.

In some example, the 3' ends of barcoded adaptors are blocked to prevent ligation. The 5' ends of barcoded adaptors contain barcodes (e.g. 3-10 bases nucleotide sequences)

In some examples, 5' ends of barcoded adaptors are blocked to avoid their ligation, and 3' ends of barcoded adaptors contain barcodes (e.g. 3-10 bases nucleotide sequences)

In some example, in the same linker a combination of known molecular identifier (3-10 bases) and unique unknown molecular identifiers (3-10 bases) is used.

In some examples, the barcoded adaptors are pre-dried on devices and are unique for each well, possibly having an organism of interest to bar code its nucleic acids.

The unique barcoded adaptors can be added to each ligation reaction in a liquid state. The unique barcoded adaptors added to each ligation reaction can be functionalized on a surface such as bead or device well.

The unique barcoded adaptors can be added to each ligation reaction in a pre-dried state, e.g. they can be pre-dried in the adaptors wells from a solution of adaptor and trehalose nuclease free water).

The ligation solution may contain RNA ligases and relevant buffers and reaction components (e.g. ATP, RNAses inhibitors, DMSO, ligase buffers, PEG). The ligation solution may also contain DNA ligases and relevant buffers and reaction components. In some examples, a linking solution contains transposase Tn5 to insert linkers directly to DNA.

The linking solution can be combined to the repaired and denatured nucleic acids and to barcoded adaptors in a mixing well. Means of mixing such as magnetic beads are added to the linking solution to promote mixing option.

In some examples, the linking solution may contain crowding agents such as PEG 8000. PEG 8000 can be provided at a concentration from about 10% to about 25%, particularly at about 15%. Crowding agents can be added to a mixing well at a separate step, or pre-mixed with some volume of the linking solution ingredients. A crowding agent can be pre-mixed with magnetic beads or with other means for mixing Linking of barcoded adapters to extracted nucleic acids in microfluidic device wells involves mixing. For example, linking of barcoded adapters to extracted nucleic acids in microfluidic device can be done by ligation at the temperature ranges optimal for selected enzymes (e.g. room temperature, or 25° C.+/−12° C. for T4 RNA ligase), in a time ranges from 20 min to few hours (e.g. 1-3 hours for T4 RNA ligase).

In some examples, pooling wells containing ligation products from the above recombined together and form a channel to collect the nucleic acids from the device.

A washing buffer can be applied. The washing buffer may contain surfactants (e.g. non-ionic detergents, BSA) and/or agents stopping the linking reaction (e.g. EDTA).

Example 4: Experimental Set-Up for RNAseq Multiple Library Prep

Figure 11:
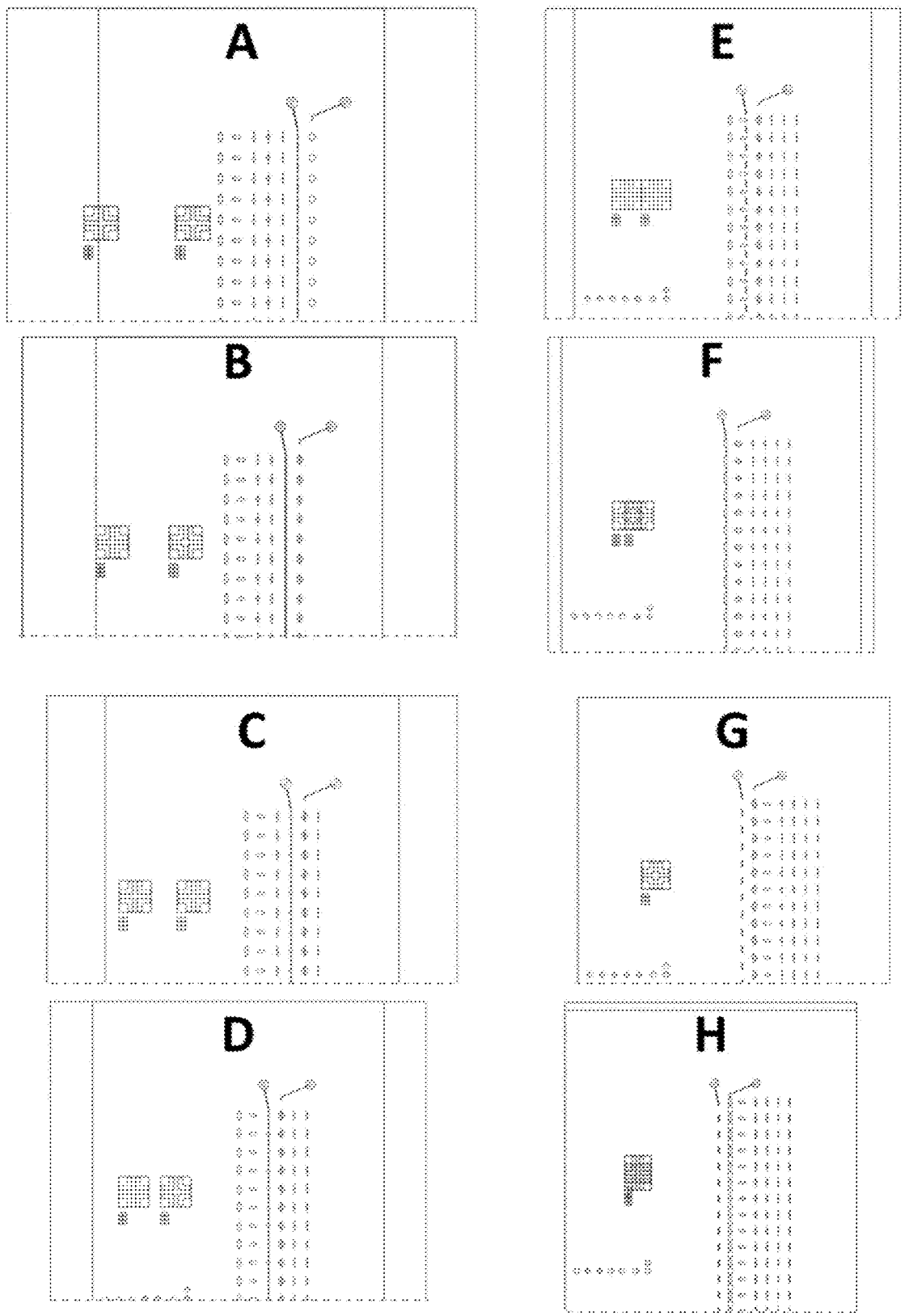
FIG. 11 shows a schematic of the operation of one embodiment of RNAseq barcoding with an example device.

FIG. 11 illustrates zoomed-out schematics of the operation of one version of the device, used for RNAseq barcoding. One end of device shown, to demonstrate one example the positioning of the via holes relative to other features. (A) Cell loading conformation. (B) Cell drop-in into the mixing well/extraction buffer loading. (C) Extraction buffer drop-in into the mixing well, heat treatment conformation. After that, RNA repair mix loading in the same conformation. (D) RNA 3'-end repair mix drop-in into the mixing well and 37° C. incubation conformation. After that, denaturing agent (e.g. DMSO) loading in the same conformation. (E) DMSO drop-in into the mixing well. (F) Adaptor addition to the mixing wells and 65° C. incubation conformation. After that, ligation mix loading in the same conformation. (G) Ligation mix drop-in into the mixing wells and incubation at room temperature conformation. (H) Conformation connecting all the mixing wells for pooling and extraction off device. Scale bar is 5 mm.

Some steps may require mixing. Mixing on-device can be accomplished by passive diffusion, magnetic bead agitation, sonication, slipping (sliding) the two glass slides slightly relative to one another to induce convection inside droplets but not enough to disconnect the wells or make any new connections, other methods, or combination of methods. Magnetic beads can also be useful for droplet manipulation or anchoring, instead or in addition to slipping or drop-in method, by holding a magnet in appropriate position relative to device.

RNA barcode (adaptor) spotting. The layout shown in FIG. 11 is designed for a barcode spot at each adaptor well (horizontal ovals), located approximately 1 mm apart. The spotting can be performed by hand, or by commercially available patterning instruments. The current spotting process is done with trehalose as adhesive/stabilizing agent (e.g. 200 nL of 10 mM trehalose, 550 nM adaptor, dried for an hour produces a spot that works well with current well size, but these volumes/concentrations are not essential and can be changed/optimized.

Figure 12:
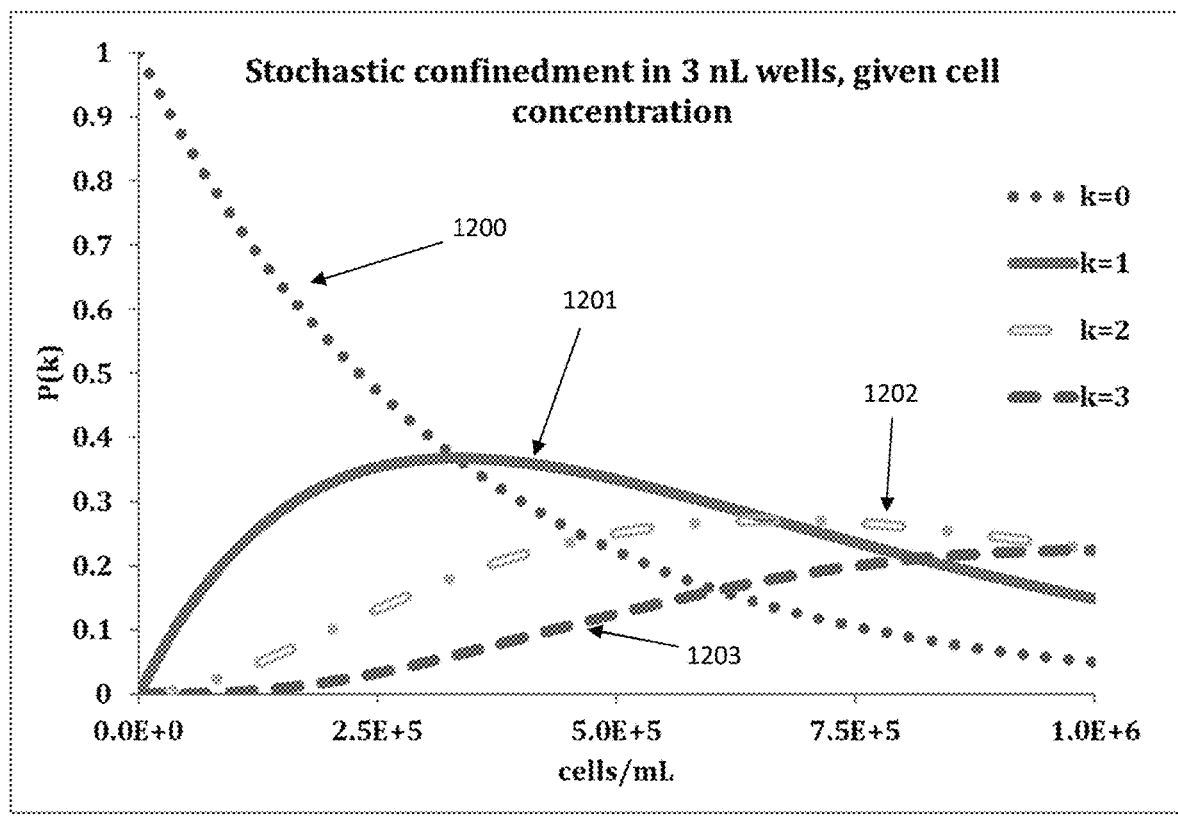
FIG. 12 shows in a plot Poisson and example probability distribution for loading 4.7 nL wells.

Cell loading. Next, after the device has been pre-spotted with adaptors and assembled with lubricating fluid, the cells can be loaded in media, or buffered csolutions—and distributed to the device's wells using trapping by sizes, active trapping, or utilizing Poisson loading (FIG. 11, panels A-B). For the Poisson loading the operator can use an appropriate concentration of initial cell suspension based on how many cells/well is desired. The volume of wells that the cells are loaded into dictates the concentrations. One example (with 4.7 nL wells) is shown in FIG. 12. Ideally, one would want to load as many wells with single cells. However, if one simply maximizes the probability of single well loading using Poisson distribution (which would correspond to 2.1× $10^5$ cells/mL, with ~37% of wells loaded with single cells), one will also increase the probability of having more wells with two or more cells to unacceptable levels (FIG. 12).

FIG. 12 shows in a plot Poisson probability distribution for loading 4.7 nL wells, for k=0 (1200), k=1 (1201), k=2 (1202), and k=3 (1203), where k is the number of occurrences (e.g. cells/well). The most wells used for single cell interrogation (k=1) is ~37%.

Cell lysis & RNA fragmentation. After the cells are loaded, the operator may want to incubate them on device, or lyse them immediately (FIG. 11, panels B-C). The lysis procedure is empirically optimized and extraction buffers can be selected applicable for the samples. The extraction buffer needs to lyse cells efficiently, and typically includes non-ionic detergents and EDTA. But the same reagents would prevent activity of many enzymes needed at the next steps for barcoding. Using the device ensures the broad choice and concentration of detergents and other reagents selected to lyse variable types of samples (e.g. eukaryotic cells, cell nuclei, or prokaryotic cells), that would be limited in other methods—e.g. droplets. Also, using the device enables the needed temperature incubation steps without reducing activity of enzymes and reagents needed at the next steps (as they are loaded later). Therefore, using the device provides both efficient lysis and efficient downstream reactions, that all happen in the additive manner, with no need for any intermediate clean ups. It provides for the rich choice of strategies for barcoding and enables targeting non-polyadenylated RNA.

Cells are lysed in the presence of chelating agents, detergents and salts, and RNA protecting agents at temperatures from room temperature to ~ 72C, depending on the cell's type. An example of the used buffer has been published at genome.cshlp.org/content/early/20Nov. 5, 2002/ gr.116103.110.abstract (Kang, 2011)[6]. Next, the short incubation at elevated temperature fragments RNA (e.g. 1-5 min at 89-91C). Other methods of fragmentation can also be used instead of thermal fragmentation (e.g. enzymatic, chemical, other, or combination of other methods). One may want to fragment the RNA for library construction, because that would increase the number of reads per gene during sequencing, reduce the secondary structure-related ligation bias, and because Illumina sequencing is optimized for certain fragment length range.

RNA 3' end repair. Next, to get the RNA fragments ready for adaptor ligation, the new ends of fragments can be repaired (FIG. 11, panels C-D). One possible method of achieving this can be by enzymatic process (e.g. T4 PNK). The adaptor will be ligated to the 3' end of the fragment (FIG. 13), which will have to be repaired after fragmentation. T4 Polynucleotide Kinase was used to do this repair, by adding the repair mix and incubating at 37° C. for 30 min. Note that the adaptors have a blocking group on their 3' ends to avoid self-ligation. The device uniquely enables compensation for the components of the extraction buffer by adding all needed components after extraction is done. Particularly, at the RNA repair step bivalent ions (Mg2+) compensate for the chelating agents (EDTA) in the lysis buffer; detergent is diluted, commercial RNAse inhibitors, inactivated at the previous steps due to heating to 72C (extraction) and 91C (fragmentation) steps, are added back as fresh reagents; concentrated buffer for the next step reaction (T4PNK repair) is added to have ideal final condition for T4 PNK activity in the total volume of the reagents present in the mixing well after adding the needed reagents.

Denaturation of repaired nucleic acids and adaptors. Once the fragment ends are repaired, we add dimethyl sulfoxide (DMSO) to the reaction mix (FIG. 11, panels D-E). After DMSO addition, the wells with the pre-dried adaptor/trehalose spots are also slipped into contact with the main reaction mix (FIG. 11F). DMSO has been long noted for its ability to relax the secondary structures of RNA.[58] In addition to relying on DMSO, we encourage the denaturation of RNA by incubating the device at 65° C. for 2 min and immediately place the device on ice (to have the RNA strands stuck in a more open conformation to help ligase "find" the fragments 3' and 5' ends). This heat treatment also deactivates the T4 PNK enzymes from RNA fragment end repair step. In the denatured state, the ligation is carried out more effectively and uniformly, mitigating the bias from template to template.

Single strand RNA/single strand RNA adaptor ligation. Next on-device step can be ligation itself (FIG. 11, panels F-G). T4 RNA ligase was used, which can be loaded in the ligation buffer, with crowding agents added either simultaneously or separately. Due to high viscosity of some crowding agents (e.g. PEG 8000), effective mixing can be optionally provided during ligation. Magnetic beads were used for mixing, but other mixing methods are acceptable as well. The particular method of mixing is not essential.

Pooling the barcoded RNA from the device. Once sufficient time has been allotted for ligation (1-12 hours at appropriate temperature (e.g. 23° C.), the samples are ready to be pooled and taken off the device. By slipping the device into the final conformation (FIG. 11, panel H) the ligation mix loading wells and the reaction mix wells form a channel that is connected to drilled holes on both ends. The reactions wells are evacuated with a micropipette through one of the holes and a wash buffer (containing chelating agents (e.g. EDTA), and optionally containing Tris PH 7.5, non-ionic detergents (e.g. Triton™ X100 or Nonidet™ P40), BSA, and RNAses inhibitors) is loaded through the other hole. The EDTA chelates Mg2+ in the solution, which stops ligase activity. The loaded buffer is collected; new wash buffer might be loaded repeatedly to collect any reaction mix that was left in the device. This washing step may be repeated.

The slipping can be done either by hand or automated. Features housing washers can be used to guide slipping. Automated and/or guided slipping will increase slipping precision, which will allow for more wells per given area of device. The number of wells on device varies from as little as 1 to as much as 10,000. Active trapping on-device can be used (e.g. trapping based on size)

Figure 13:
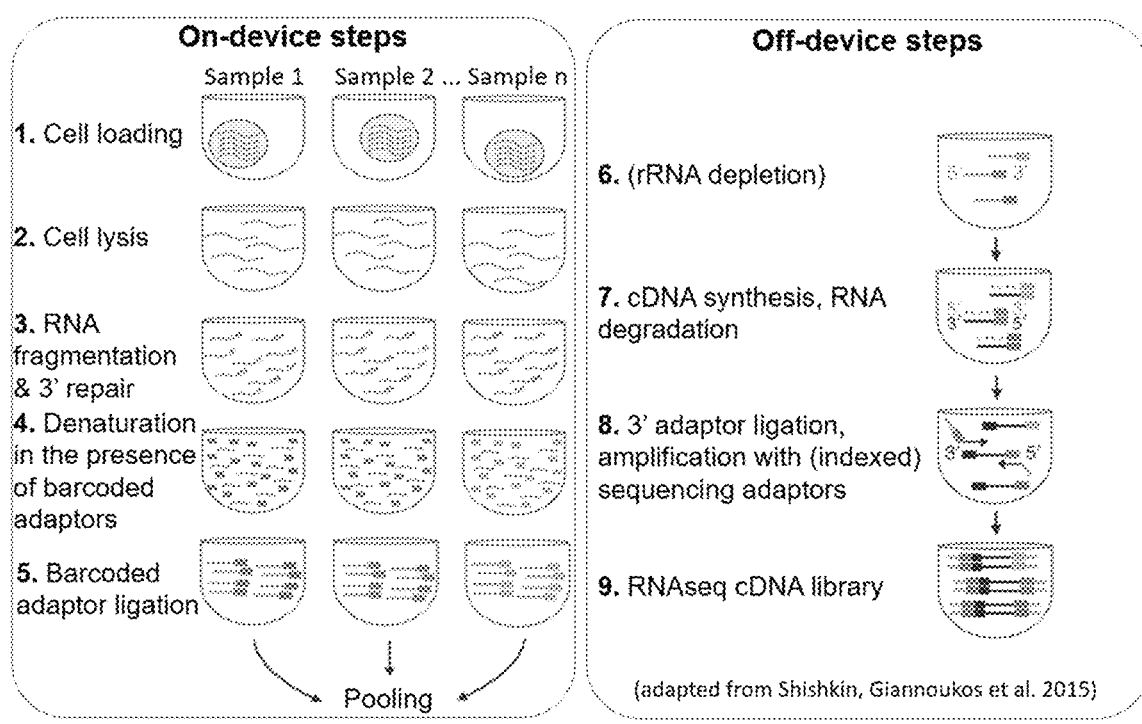
FIG. 13 illustrates a simplified schematic of RNAtag-Seq method.

FIG. 13 illustrates a simplified schematic of RNAtag-Seq method. Barcoded adaptor ligation is performed in device, and the rest of the RNAtag-Seq is performed off-device as described by Shishkin et al. (2015)[8]. The different blocks represent unique sequence barcodes: Illumina sequencing adaptors and Illumina index barcodes. Black blocks represent adaptors ligated to provide region of complementarity for index-containing primers (grey blocks). Note that the barcoded adaptors (added during first ligation) end with a constant region as well, providing the region of complementarity for the sequencing adaptor primers.

Following on-device barcoded adaptor ligation, off-device part of the RNAseq protocol is carried out as described by Shishkin et al. (2015)[8]. Briefly, the linkers and adaptors are washed away using optimized ethanol concentrations and sorbtion of nucleic acids that are longer than a certain length using magnetic beads, while the barcoded RNA samples are cleaned and concentrated on a silane beads or silica column, and optionally depleted of rRNA (if desired). Each barcode that we ligated to the RNA fragments ends with a constant region, which is complementary to the RT primer, allowing reverse transcriptase enzyme to synthesize the first strand of cDNA. RT-primer is then degraded using exonucleases and washed away using silane beads. RNA is then degraded by exposing it to both chemically (NaOH solution) and thermally (12 min at 70° C. incubation), while the barcoded cDNA is washed and concentrated.

Next, one more ligation can be performed, adding a single stranded adaptor to the 3' end of cDNA fragments to provide a constant region that the PCR primers will be able to bind to during amplification. In addition to providing binding site for the 3' PCR primers, the adaptor ligated to the 3' end contains a unique molecular identifier that is used in bioinformatics assays to correct for PCR biases and duplication rates. Now that a cDNA from transcript fragment is enclosed between constant regions of known sequence, it is ready for amplification with PCR primers carrying the adapters for NGS. For example, the PCR primers can include Illumina sequences standard adaptors for sequencing cDNA library.

Example 5: Single Cell RNAseq Protocol

The following steps were performed on-device. The adaptors were pre-dried on one of the SlipChip™ glass slides. Table 1 shows examples of barcoded adaptor sequences.

TABLE 2

Examples of barcoded adaptor sequences

| A01 | AAGCAA U | /5Phos/rArUrU rGrCrU rUrArG rArUrC rGrGrA rArGrA rGrCrG rUrCrG rUrGrU rArG/3SpC3/ | SEQ ID NO: 3 |
|---|---|---|---|
| B01 | AAUUCA U | /5Phos/rArUrG rArArU rUrArG rArUrC rGrGrA rArGrA rGrCrG rUrCrG rUrGrU rArG/3SpC3/ | SEQ ID NO: 4 |

200 nL droplets with 10 mM trehalose and desired concentration of adaptors were prepared, containing 10-40 fmoles of each adaptor, within a range of 5-200 fmoles. Trehalose is used to stabilize the nucleic acids and to help with sticking of the adaptors to silanized glass. The etched pattern will dictate the spots for droplets.

The following steps (steps 1-12) were then carried out:
1. Adjust concentration of cells for Poisson loading or provide trapping by size or active trapping
   50e3 cells/mL maximizes the probability of single cell loading (P~. 187, per Poisson distribution) at sufficiently low probability of having wells with 2 cells (P~. 022)
   Load cells using the $1^{st}$ array of wells, 3 nL each
   Loading can be done in media
2. Load extraction buffer (any variant, including described in the claims)
   Load using the $2^{nd}$ array of 5 nL wells
   Ingredients and their functions:
   Lysozyme (weakens cell membrane); will not need for mammalian cells or G-bacteria
   Tris-HCl-stabilizes PH, at room temperature and when the buffer is heated.
   EDTA (destabilizes cell membrane, takes up $Mg^{2+}$ ions (undesired property, will need to replenish $Mg^{2+}$ in the next step))
   Non-ionic detergents (de-stabilize cell membrane, denature proteins to release RNA)
   DTT (reducing agent, prevents RNAse action)
   SUPERase inhibitor (RNAse inhibitor, protects RNA)
   BSA (minimizes protein/RNAse inhibitor losses at interfaces)
   KCl (increases protein solubility, frees up RNA from said proteins)
3. Incubate:
   72-73C 2 min (preparing cells to lyse)
   skip this step for mammalian cells
   91° C. for 2 min (cell lysis and RNA fragmentation)

4. Add RNA repair mix
  Load in the 3rd array of 8 nL wells
  Ingredients:
    Regular T4 PNK (NEB M0201L)
      In absence of ATP removes 3'-P
      Repairs 3' ends of fragments and makes them available for ligation
    T4 PNK buffer
    Superase inhibitor (RNAse inhibitor)
    MgCl (to compensate for removal of $Mg^{2+}$ by EDTA in previous step)
5. Incubate:
  37° C. for 20-30 min
6. DMSO addition
  Load in 4th array of 5.4 nL wells
  Relaxes the secondary structures of RNA fragments and adaptors, helps to denature adaptors and template, minimizes the ligation biases
7. Slip to add the pre-dried adaptors to the mix
  $5^{th}$ array of wells for pre-drying
8. Incubate:
  65° C. for 2.5-3 min
    To denature the RNA adaptors, unfold RNA fragments, and deactivate T4 PNK
  Put on ice immediately
    To reduce the renaturing of RNAs to their most stable conformations
9. Add ligation reaction mix
  Load in the 6th array of 20 nL wells
  Ligate the adaptors to the transcripts for barcoding
  Barcoded adaptors need 5'-P and 3' ddC (or 3'-C3 spacer)
  Ingredients:
    T4 RNA ligase
    NEB ligase buffer
    DMSO (helps ligation by stabilizing strands in unfolded state)
    ATP (ligase energy source)
    Superase inhibitor (RNAse inhibitor)
10. Add PEG 8000 (crowding of RNA/adaptors/ligase) with magnetic beads washed in ddH20 and added at 1/10 v/v.
11. Allow 40 min-2 hours for ligation at room temperature, with magnetic mixing
12. Slip into the final conformation, where the wells are overlapped, and the final reaction mixture can be evacuated off the device
  Take the reaction mixture from device (total volume is 2.7 μL currently)
  Use wash buffer (10 mM Tris, 5 mM EDTA, pH 7.5, NP40 0.1%) to wash the device 2 additional times (total combined volume of 20 μL)
  EDTA binds $Mg^{2+}$ ions and stops enzymes activity
The following steps (steps 13-18) were carried out off-device.
13. Bind the pooled samples to MyOne Silane beads, 3×RLT and 0.6 v total 100% EtOH
14. Quick protocol for Ribo-Zero™ rRNA removal kit
  rRNA very abundant, has identical sequences
15. Silane beads (Invitrogen) linker cleanup
16. First strand cDNA synthesis
  Take 9 μL rRNA depleted RNA (use all the material from above)
  Add 1 μL (5 pmoles) of R14s primer (5 μM)
    5'-/5SpC3/CTACACGACGCTCTTCC-3'=R14S, 17 bp, Sequence-specific primer for first-strand cDNA synthesis
  Mix well
  Heat the mixture to 70° C. for 2 min and immediately place on ice (on cold block on ice)
  Make RT mix below: For multiple samples, a mastermix can be prepared ahead of time and added to the RNA/AR2 tube on ice.
  Add (in order on ice):

| | |
|---|---|
| RT Mix | 1 reaction |
| Water | 4 μL |
| 10x AffinityScript RT Buffer(or other) | 2 μL |
| DTT (0.1M) | 2 μL |
| 25 mM dNTP Mix (25 mM each) | 0.8 μL |
| RNase inhibitor, murine (40 U/μL) | 0.4 μL |
| AffinityScript RT Enzyme (or other(or other RNAseH (minus))) | 0.8 μL |
| rRNA depleted RNA + R14s primer | 10 μL |
| Total | 20 μL |

Add 10 μL of RT mix to the 10 μL rRNA depleted RNA+R14s RT primer on ice
  Mix well and spin for 5 sec
  Place in HOT (55° C.) incubator or thermocycler. Incubate at 54° C. for 45 minutes
17. ExoSap—It primer removal after RT:
  add 3 μL ExoSap—It to 20 μL RT reaction, incubate at 37 C for 15 min, add 1 μL EDTA 0.5M.
18. RNA degradation after RT and Silane beads cleanup
  Add 1/23 reaction vol. of 3N NaOH (1 μL) to each reaction
  Incubate at 70° C. for 12 minutes
  Neutralize with 1 μL of 3M HCL acid; mix well
  Total volume=26 μL
Reverse Transcription primer removal/cDNA cleanup were carried out as follows with MyOneSilane beads to remove enzyme and reaction buffer.
  add 7 ul silane beads, add some RLT to the beads to rinse storage buffer, remove SUPernatant.
  Bind with 3.0× of fresh RLT (with beads) and 0.6× (RNA+RLT volume) EtOH, mix well.
  Incubate at room temperature for 10 min, mix well
  Place on magnet for 1 min or until solution is clear
  Aspirate out and discard clear solution
  Wash beads in 123 ul of 70% EtOH twice, incubate for 30 sec
  Aspirate out and discard the clear solution
  Add full tube of fresh 70% EtOH without removing from magnet and incubate for 30 sec
  Aspirate out and discard the clear solution and let air dry for 3-10 min
Second ligation (ssDNA/ssDNA) of 3' linker on beads were carried out as follows:
  Keep Silane beads-do not transfer to new tubes, add on top 5.6 ul of solution, containing 2.4 ul of water, 1.2 ul of low TE, 80 pmoles of 38-linker in 1 ul and 1 ul DMSO.
  Heat beads and solution at 70C for 2 min, Place on cold block on ice
  38 adaptor: 5'-ANNNNNNNNAGATCG-GAAGAGCACACGTCT-3' (Needs: 5'-Phosphate and 3'-ddC or 3'-C3 spacer)
  Make ligation reaction mix: For multiple samples, a mastermix can be prepared ahead of time and added to the cDNA/38-linker tube at ROOM TEMPERATURE.
  2nd Ligation Mix, add 15 ul to cDNA+adapter mix: 1 reaction

| | |
|---|---|
| Water, H₂O | 1.8 µL |
| 10x T4 Ligase Buffer | 2 µL |
| DMSO (100%) | 0.8 µL |
| ATP (100 mM) | 0.2 µL |
| PEG 8000 (50%) | 9 µL |
| T4 RNA Ligase 1 (30,000 U/mL) | 1.2 µL |
| Total | 20 µL |

Swirl the cDNA/beads/water with pipet tip PRIOR to dispensing 15 µL ligation mix Mix well by pipetting up and down ~10× or cap tubes and shake at mixer several times; solution is viscous Do not spin Incubate overnight at 22° C., shake sometimes Coupling MyOneSilane beads to second linker were carried out as follow: add extra 3 ul silane beads per sample, rinse with RLT, remove supernatant, bind with 3V fresh RLT and 0.5V (RLT+beads+sample) EtOH Incubate at room temperature for 7 min, mix well Place on magnet for 1 min or until solution is clear Aspirate out and discard clear solution Add twice 123 µL of fresh 70% EtOH without removing from magnet Aspirate out and discard the clear solution Add fresh 70% EtOH to the top of a tube without removing from magnet and incubate for 30 sec Aspirate out and discard the clear solution and let air dry for 3-10 min (beads stop shining)

Elute in 23 ul of mixture (2V of water+1V of low TE)

PCR Enrichment using all ligated cDNA to PCR reaction was carried out according to the follow procedures.

Primers sequences are:

```
P_Universal:
                                    SEQ ID NO: 2
5'-AATGATACGGCGACCACCGAGATCTACACTCTTTCCCTACACGACGC
TCTTCCGATCT-3'

Example of indexed primer 2P_504:
                                    SEQ ID NO: 1
5'-CAAGCAGAAGACGGCATACGAGATCCTGGTAGGTGACTGGAGTTCAG
ACGTGTGCTCTTCCGATCT-3'
```

A PCR mix was prepared as follows:

| PCR Mix | 1 Reaction |
|---|---|
| cDNA+ | 23 µl |
| Primer mix, 25 µM each (2P_Univ + 2P_indexed) | 2 µl |
| NEBNext Q5 HotStart mix (or other high-fidelity hot start mix) | 25 µl |
| Total | 50 µl |

The time and temperature for each PCR cycle is shown in the following Table 3:

TABLE 3

| | | |
|---|---|---|
| 98° C. | 40 Sec | |
| 98° C. | 20 sec | 6 cycles |
| 70° C. | 30 sec | |
| 72° C. | 60 sec | |
| 98° C. | 20 sec | 10 cycles |
| 72° C. | 1 min | |
| 72° C. | 1 min | |

SPRI beads clean up can be carried out to remove reaction buffer and PCR primers:
a. Add 1.2× or less AMPure beads directly to PCR mixture, and mix up/down 15×
b. Incubate at RT for 10 min
c. Place on magnet for 5 min or until solution is clear
d. Aspirate out and discard clear solution
e. Add 200 µL fresh 70% EtOH without removing from magnet and incubate for 30 sec
f. Aspirate out and discard the clear solution
g. Add 200 µL fresh 70% EtOH without removing from magnet and incubate for 30 sec
h. Aspirate out and discard the clear solution and let air dry for 2-5 min
i. Elute off beads with 21 µL sterile low TE buffer Additional cycles can be added after SPRI beads clean up. 1 ul of the eluate is then analyzed on DNA High-sensitivity BioAnalyzer.

Figure 14:
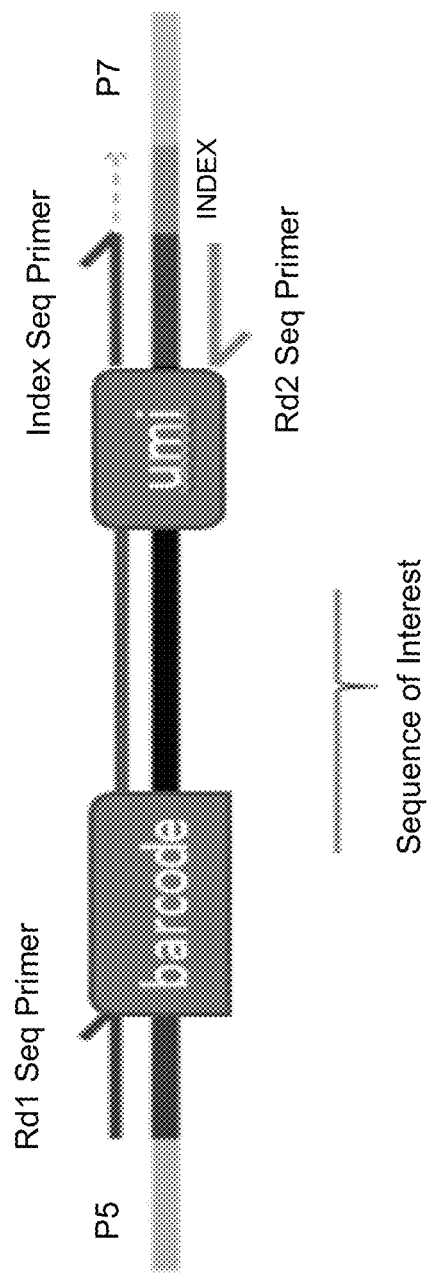
FIG. 14 illustrates an exemplary structure of a ready-to-sequence RNA seq library for Illumina paired-end sequencing.

FIG. 14 illustrates an exemplary structure of a ready-to-sequence RNA seq library for Illumina paried-end sequencing.

Figure 15:
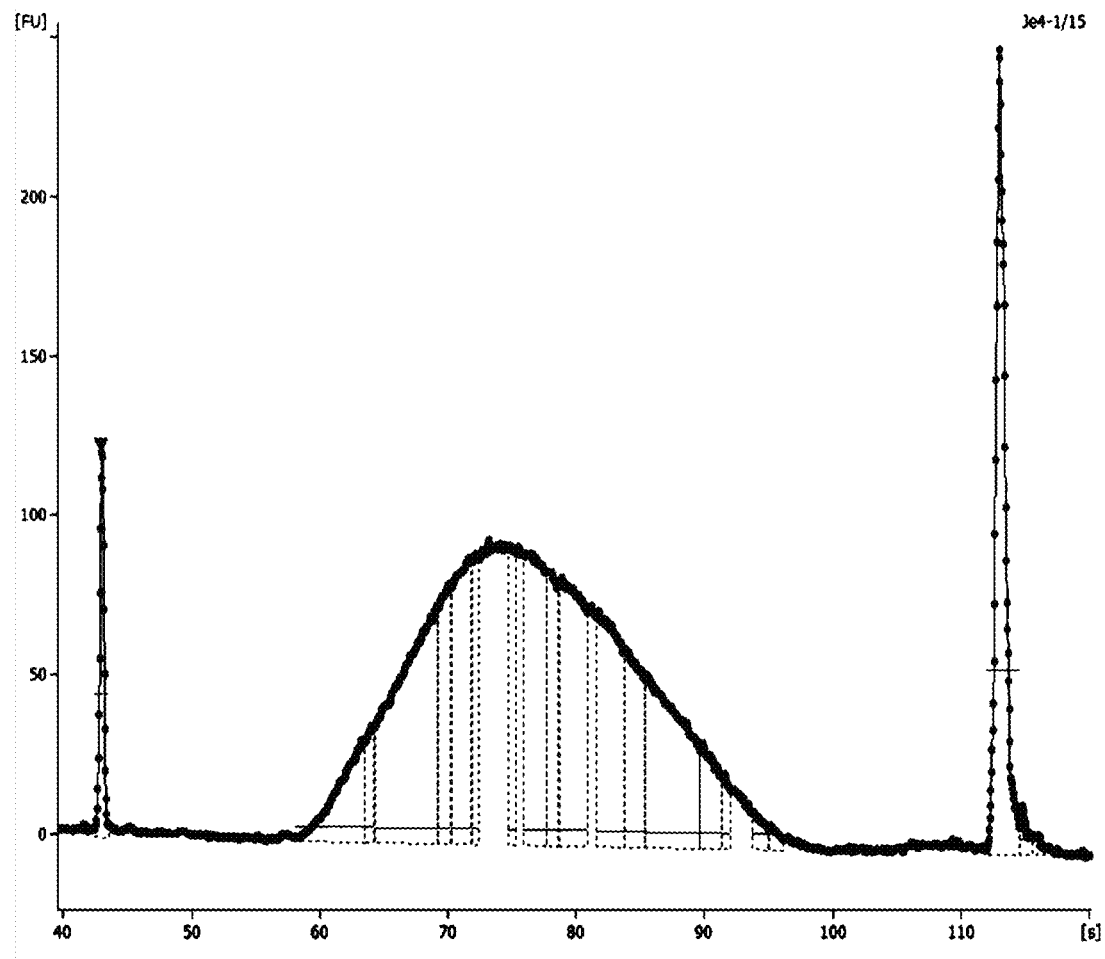
FIG. 15 shows Agilent Bioanalyzer image of an example RNAseq library.

FIG. 15 shows bioanalyzer image of the RNAseq library produced from 8.5 pg of K562 with extracted and repaired RNA loaded in each device well.

Sensitivity of RNAseq using the device herein described is estimated using ERCC spike-in control RNA and compared to the published scRNA method DropSeq (Macosko 2015)[1] that targets poly(A) RNA only and does not allow full-length sequencing.

Figure 16:
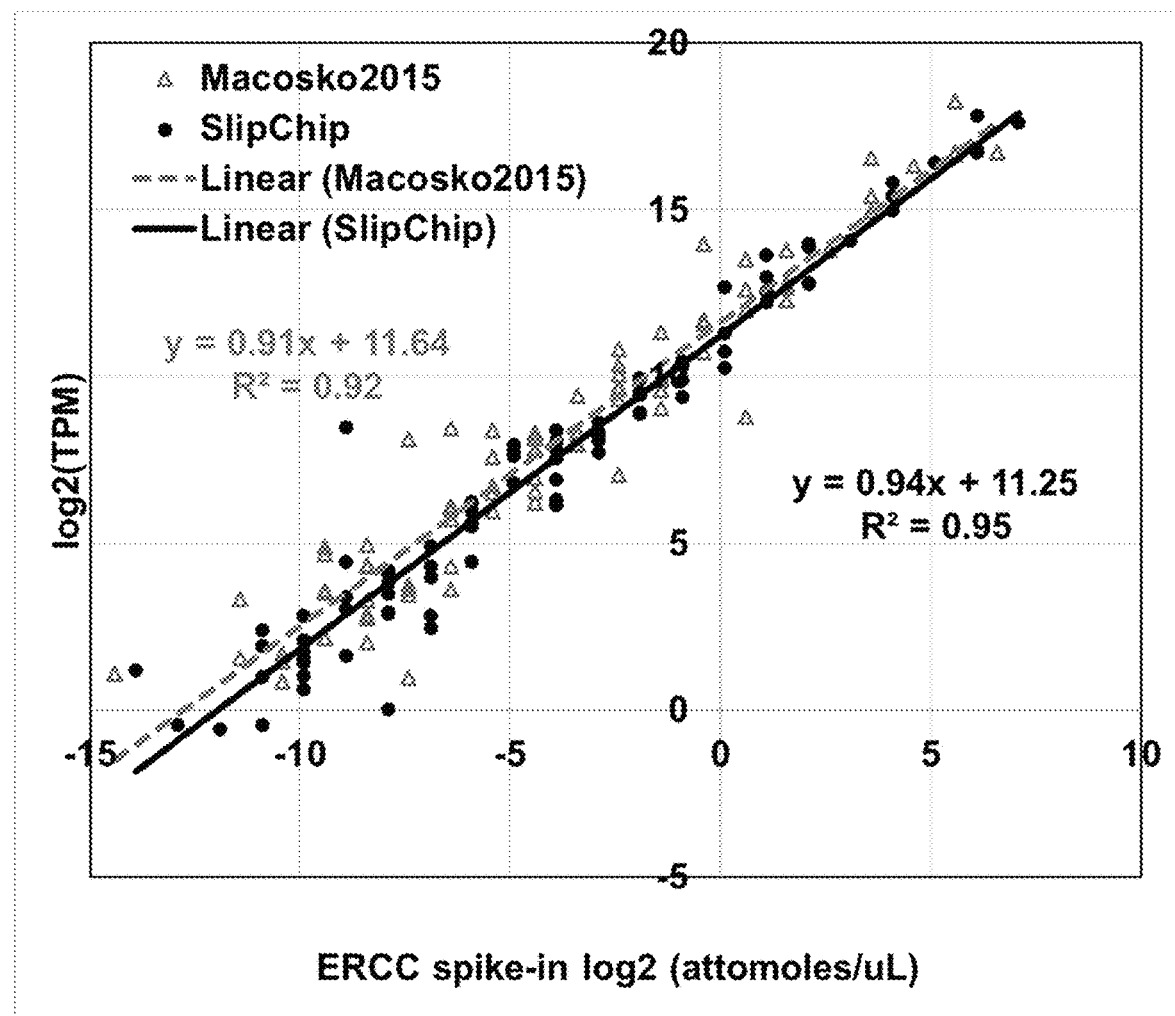
FIG. 16 shows in a plot dose-response slopes of ERCC spike-in transcripts using an example device, and comparing it to equivalent data from another published technology, Drop-seq.

FIG. 16 shows in a plot dose-response slopes of ERCC spike-in transcripts using the device herein described and compared with Drop-seq data set published in Macosko et al., 2015[1]. The data are in close agreement.

Figure 17:
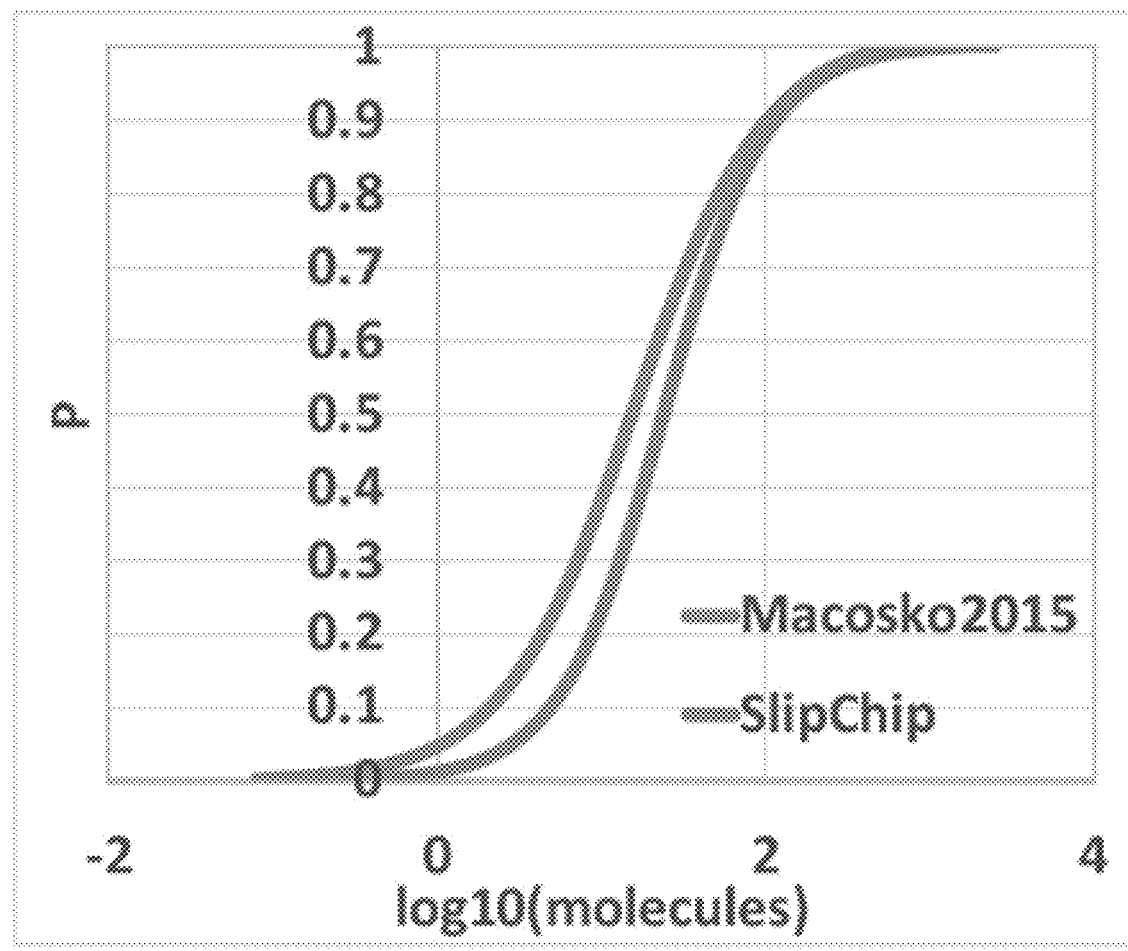
FIG. 17 shows in a plot detection probability of spike-in control (ERCC) for example device RNAseq and Drop-seq methods.

FIG. 17 shows in a plot detection probability of spike-in control (ERCC) for example device RNAseq and Drop-seq methods. The method herein described requires 23.8 ERCC molecules for 50% probability of detection compared to 12.2 molecules for Drop-seq method of Macosko 2015[1].

Figure 18:
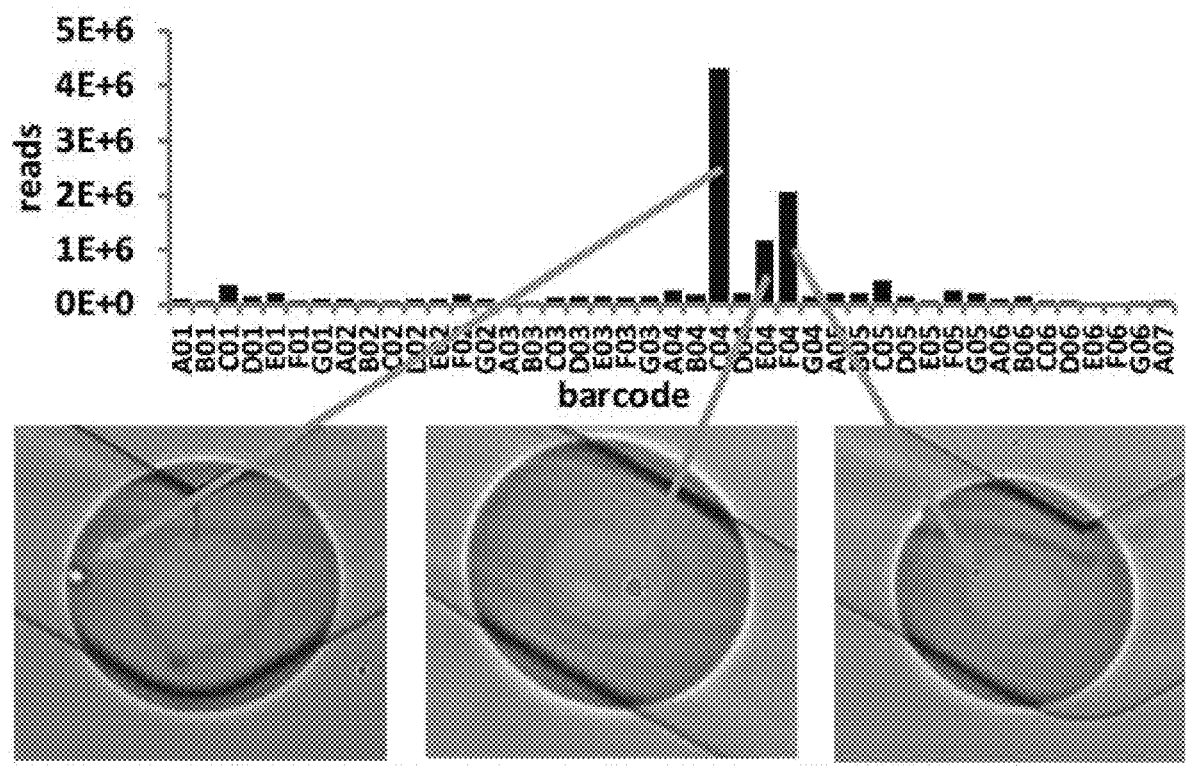
FIG. 18 shows RNA-Seq reads from single mouse ES v6.5 cells.

FIG. 18 shows RNA-Seq reads from single mouse ES v6.5 cells to illustrate the connection between on-device images and sequencing. The data shows that the barcoded device wells produce the specific relevant barcodes read sequences in the RNAseq data.

Figure 19:
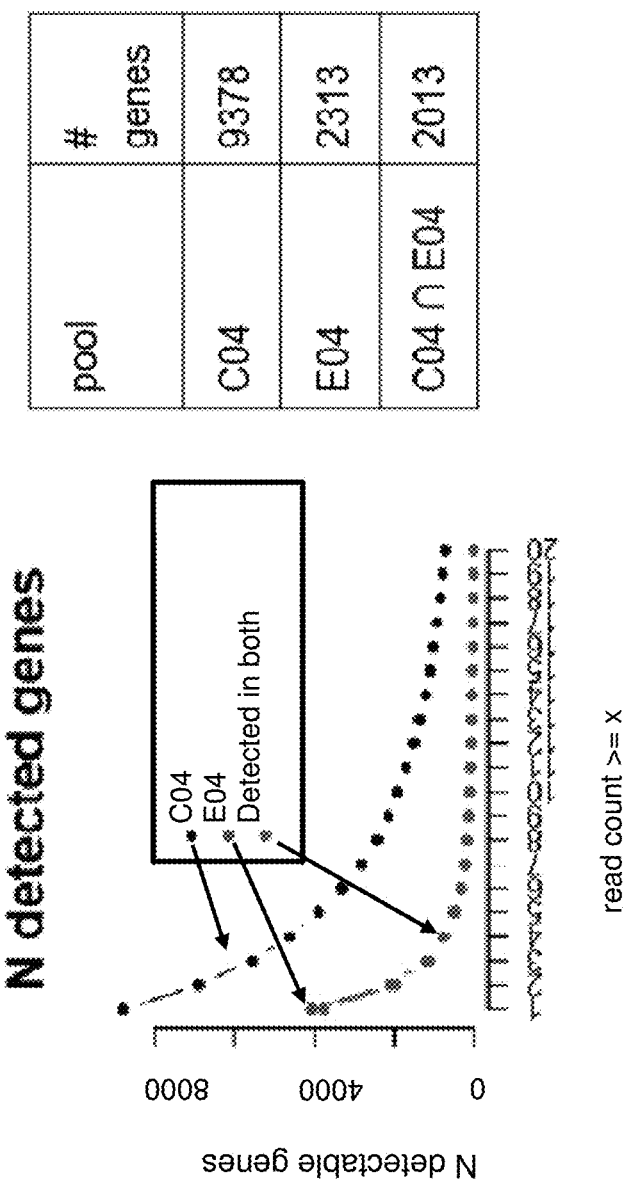
FIG. 19 shows in a plot the number of genes detected in single eukaryotic cells

FIG. 19 shows in a plot the number of genes detected in single eukaryotic cells. The number of detected genes is similar to what is usually detected by other sc RNAseq methods. C04 and E04 are ID's of two different barcodes, corresponding to two different single cells. FIG. 19 shows the number of different genes detected for each, along with the reads distribution (e.g. 4000 genes in both cells were detected with at least 1 read, 2000 genes in both cells were detected with at least 2 reads, etc.).

Figure 20:
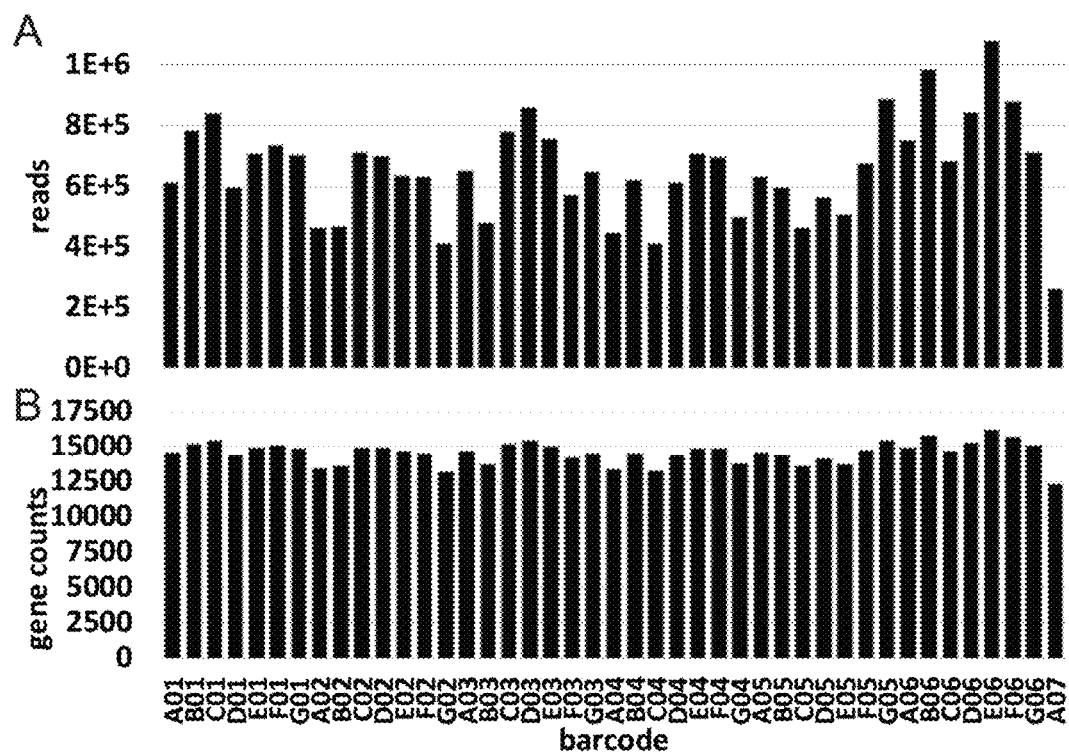
FIG. 20 shows the number of gene counts for each barcode for an example RNAseq.

Repaired human RNA (67.2 pg/8 nl well) is used to check for on-device bias. FIG. 20 shows the number of gene counts for each barcode. Barcodes are shown according to spatial replacement within the device. (A) total reads per barcode; (B) gene count per barcode. Sequencing depth 3.7e7 paired-end reads. A well-to-well uniformity of detection is demonstrated.

Figure 21:
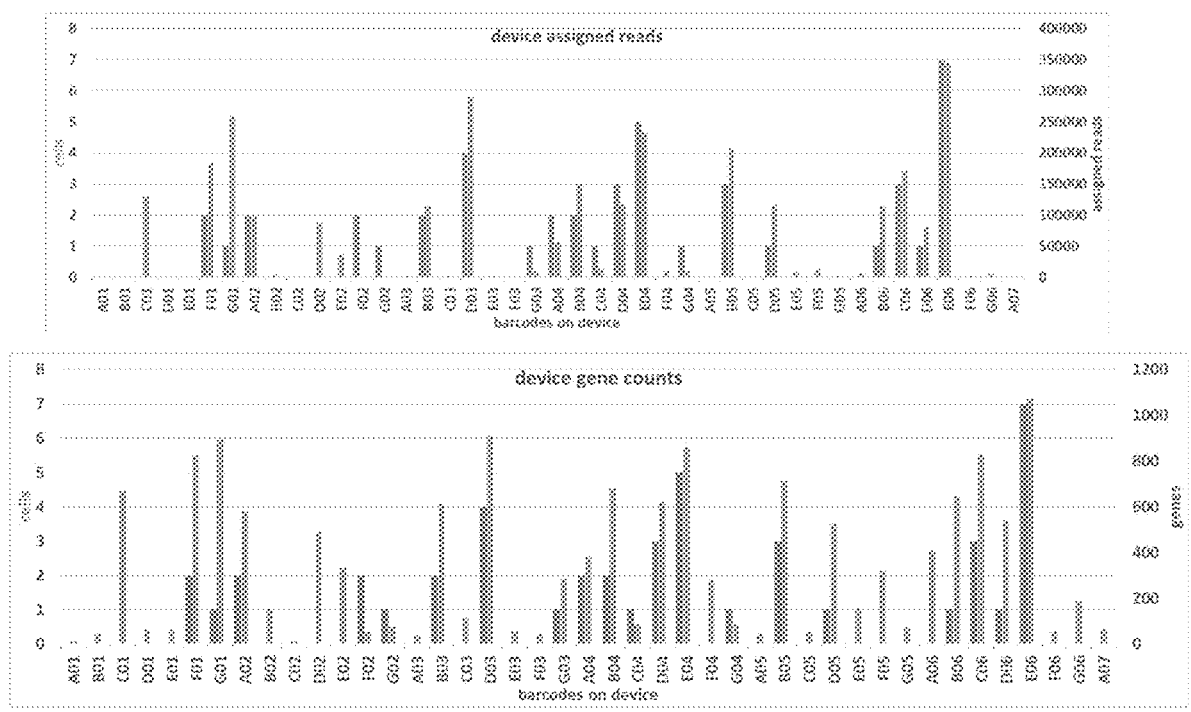
FIG. 21 illustrates a correlation between *E. coli* cell imaging and read allocation to barcode data.

In one example, *E. coli* DH10B were loaded on device, imaged, sequenced, and corresponding genes were detected through RNAseq. FIG. 21 demonstrates the correlation between cell imaging and read allocation to barcode data. FIG. 21 shows the connection between imaging data and sequencing data: Top=bacteria detected by imaging on left axis, assigned reads on the right axis; Bottom=bacteria detected by imaging on left axis, genes detected on the right axis.

Figure 22:
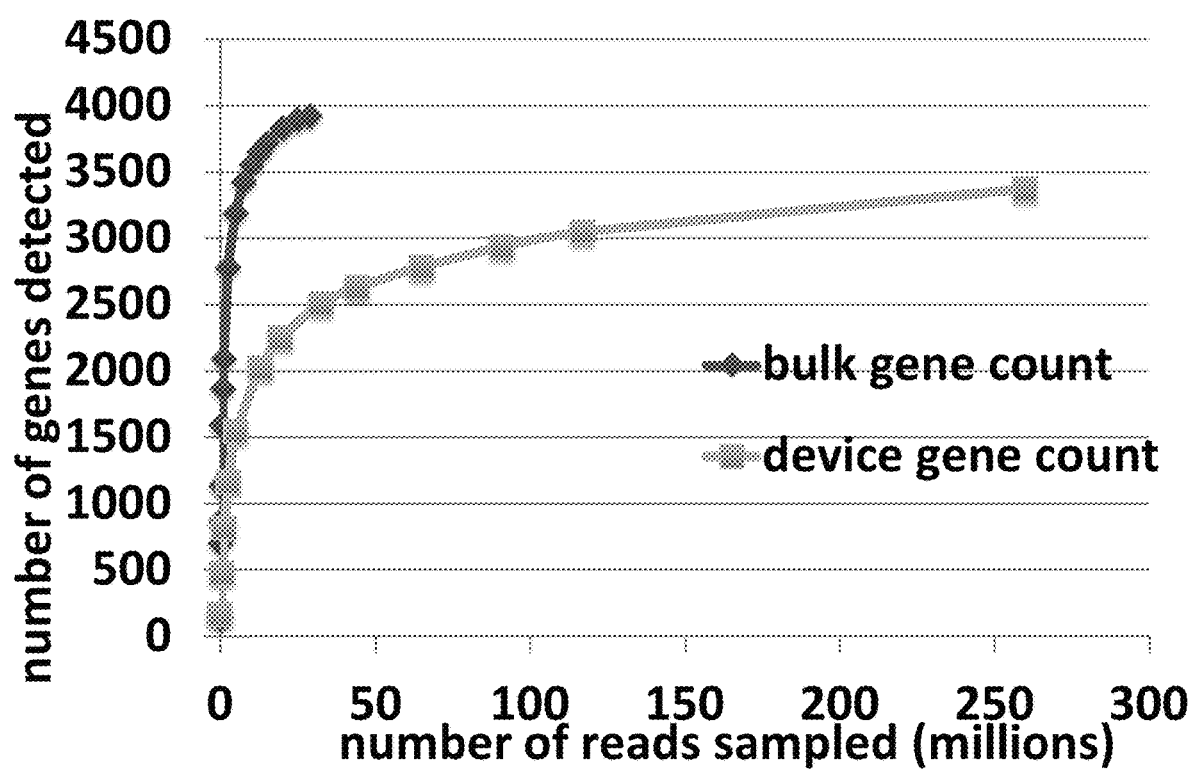
FIG. 22 shows an example graph of number of *E. coli* genes detected versus number of reads sampled in bulk vs. by device.

FIG. 22 shows an example graph of number of genes detected versus number of reads sampled in bulk vs. by device.

Figure 23:
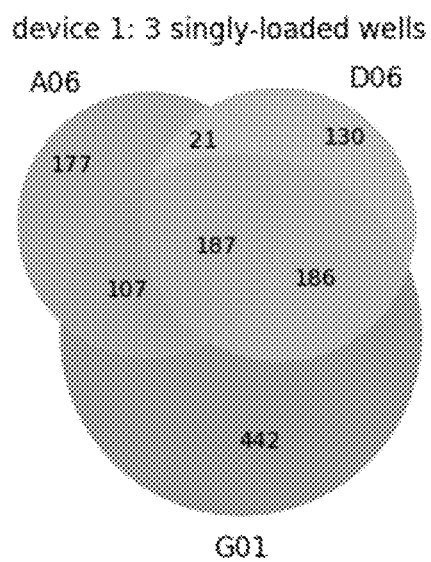
FIG. 23 shows a schematic illustrating heterogeneity of gene expression in single *E. coli* cells.
Figure 23:
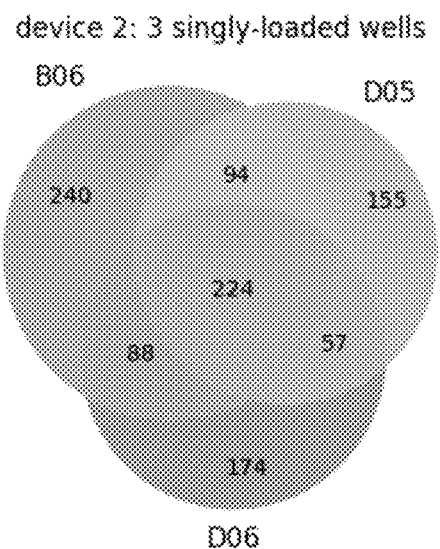
Figure 23:
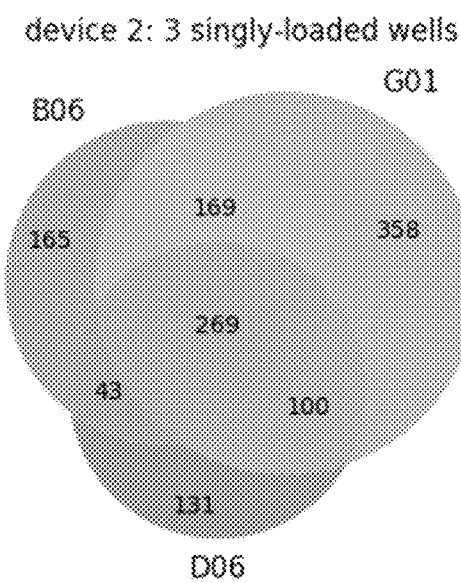

FIG. 23 shows a schematic, illustrating heterogeneity of gene expression in single cells, with A06, B06, D01, D06, and G01 being different barcodes for single cell wells.

Figure 24:
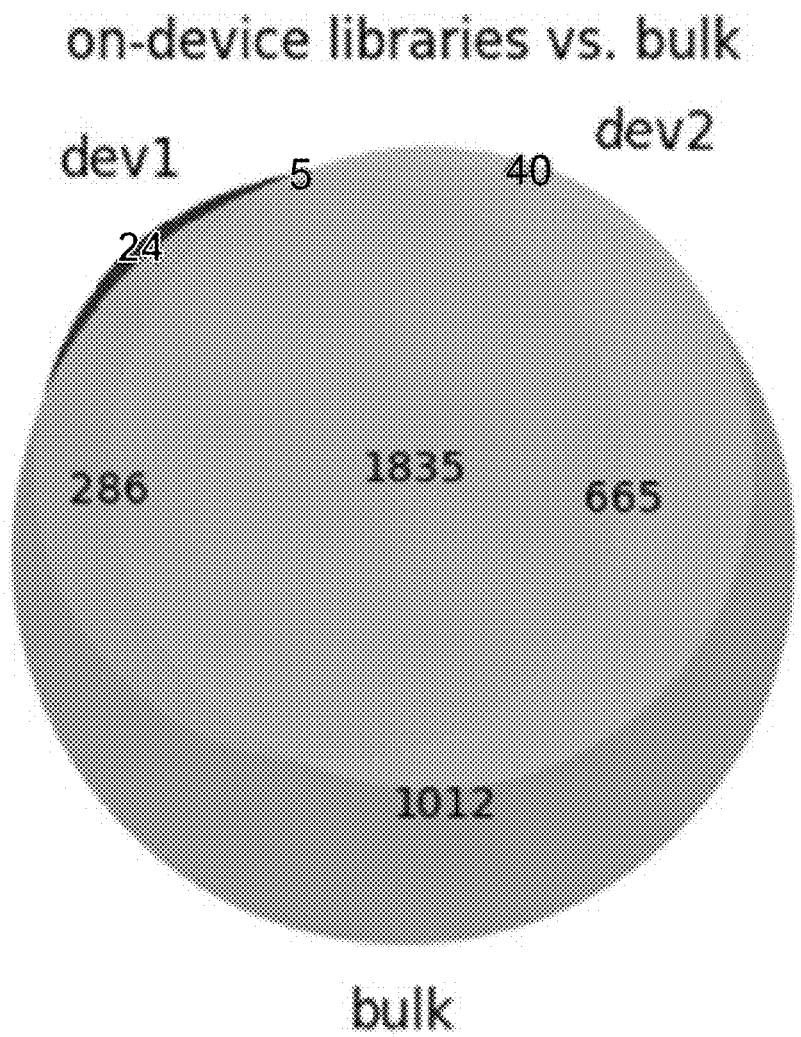
FIG. 24 shows a schematic illustrating the sum of all *E. coli* genes detected on-device vs. in bulk

FIG. 24 shows a schematic, illustrating the sum of all genes detected on-device vs. in bulk (for two test devices).

Figure 25:
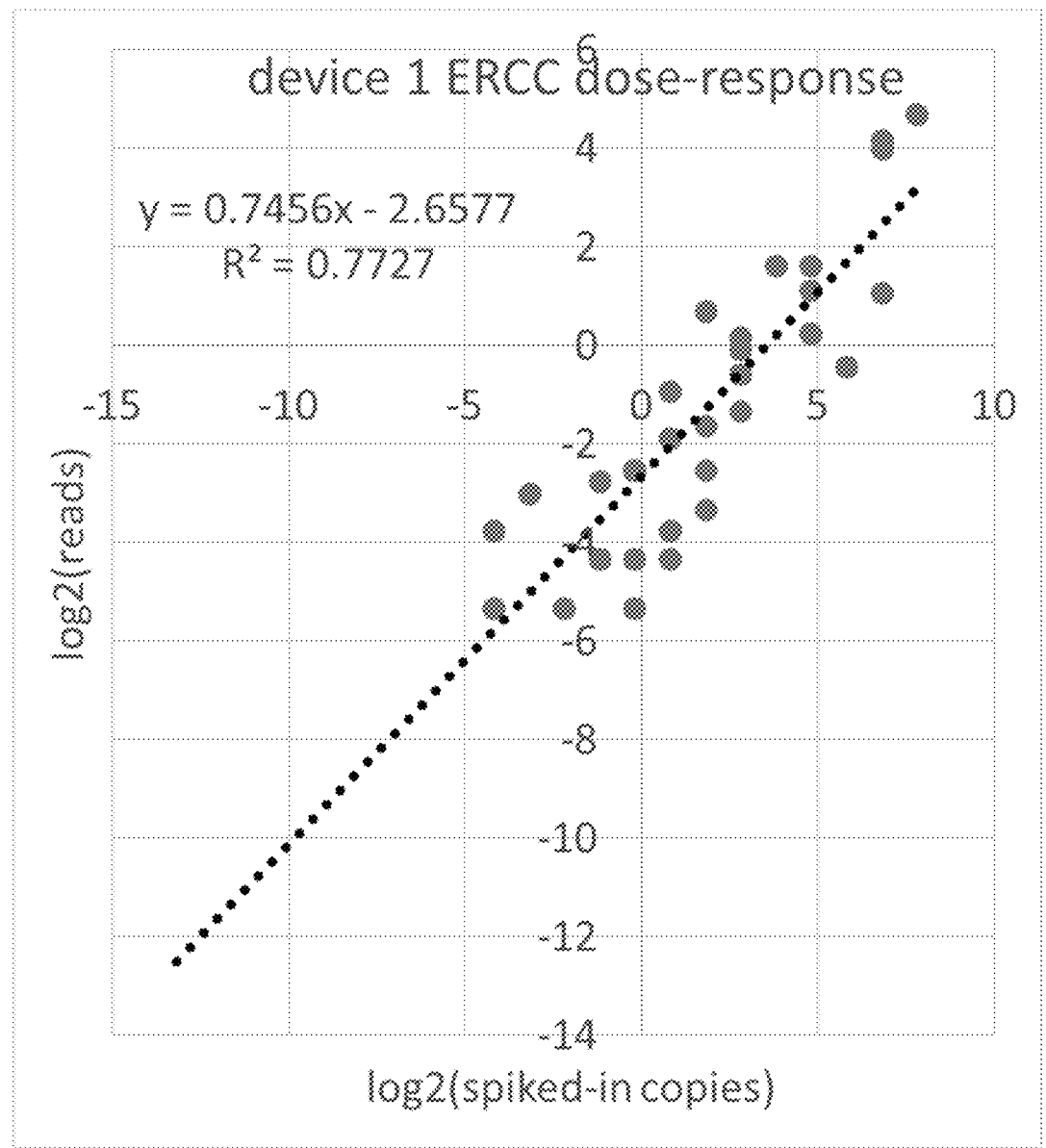
FIGS. 25-26 shows diagrams illustrating results of experiments showing the on-device detection efficiency of an example device.
Figure 26:
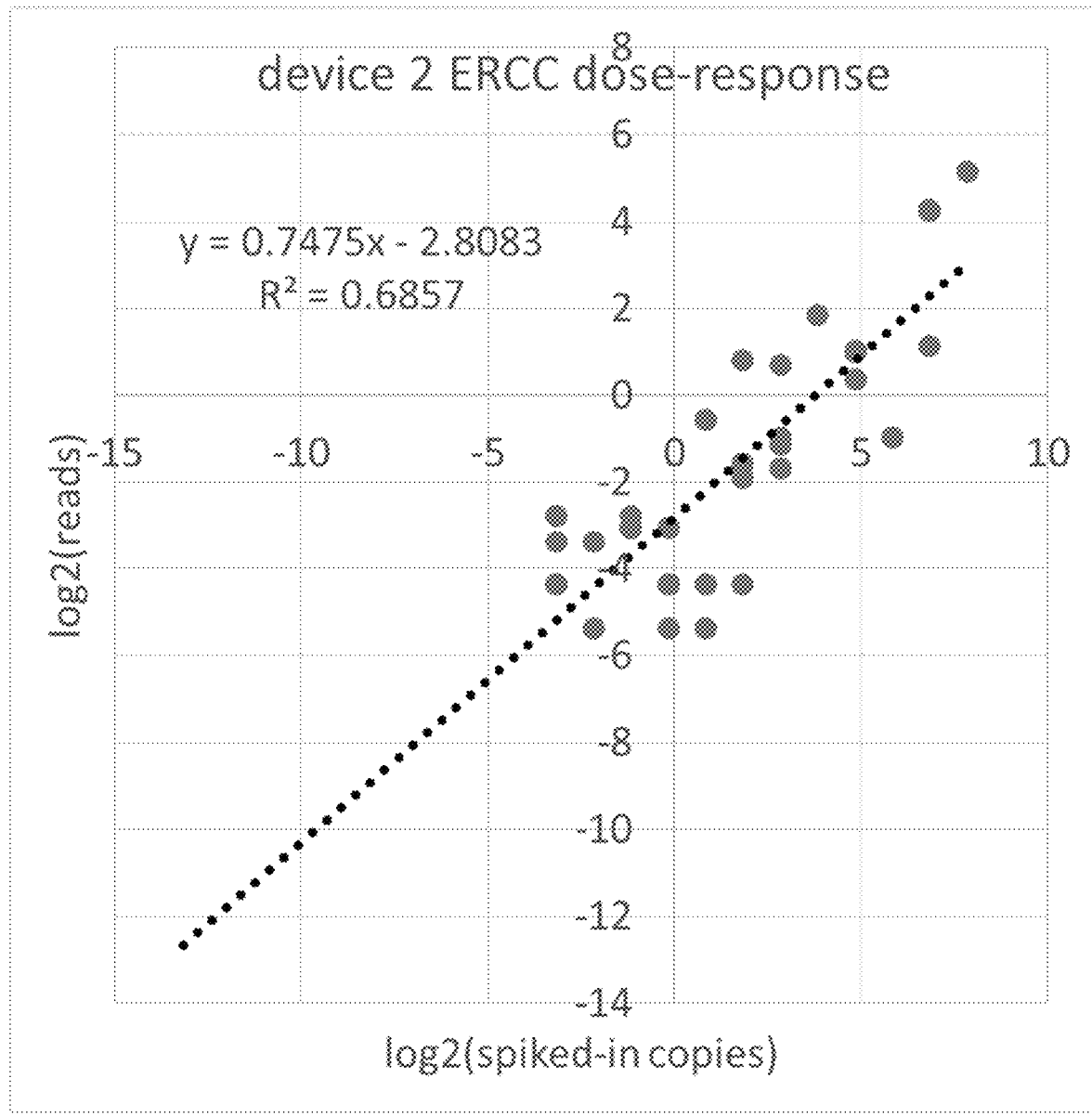

FIGS. 25-26 show the on-device detection efficiency of the test devices of FIG. 24, based on dose-response of ERCC spike-ins: 0.143 for device 2 and 0.158 for device 1.

Figure 27:
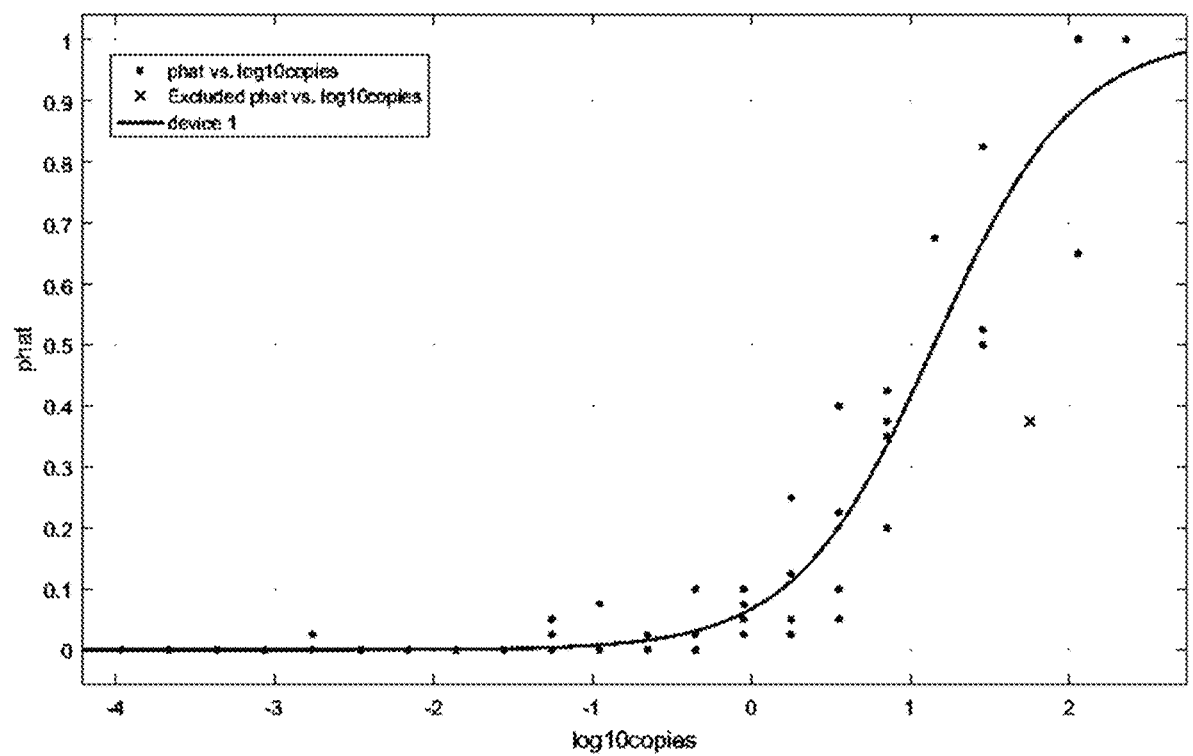
FIGS. 27-28 shows diagrams illustrating results of experiments showing an example on-device detection probability.
Figure 28:
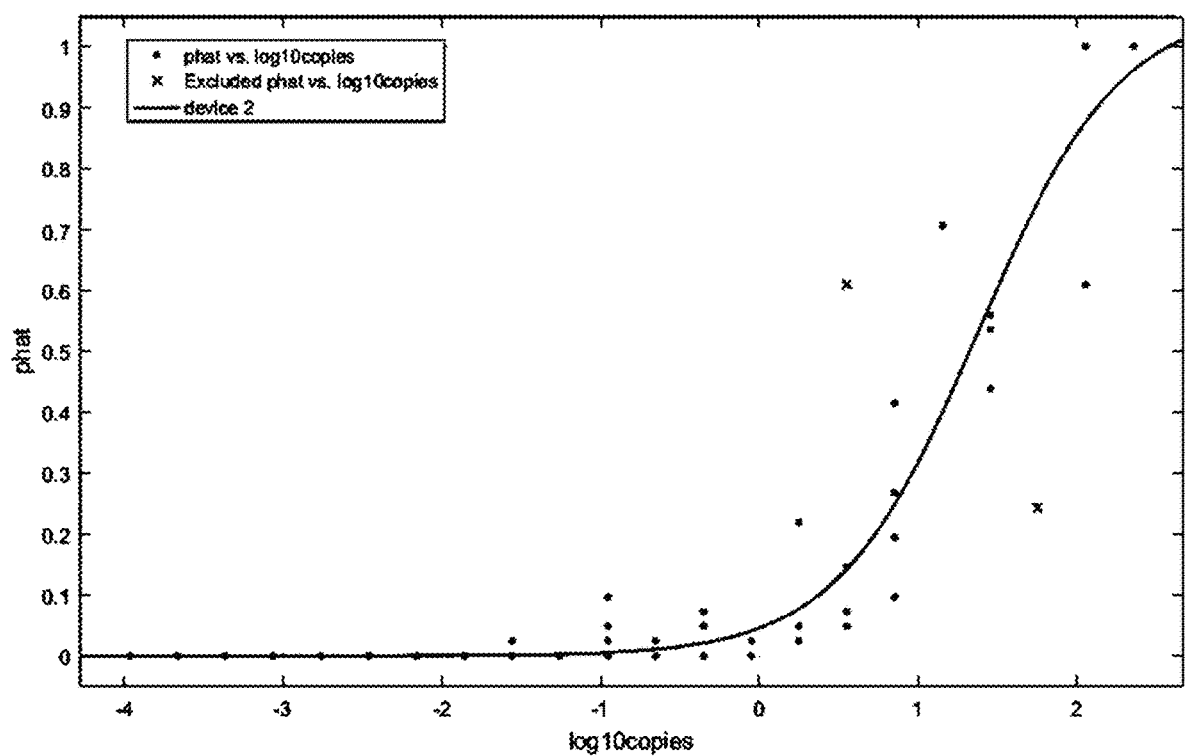

FIGS. 27-28 show the on-device detection probability, based on ERCC spike-in detection: 14.0 (device 1) and 20.9 (device 2) copies for 50% detection probability.

Figure 29:
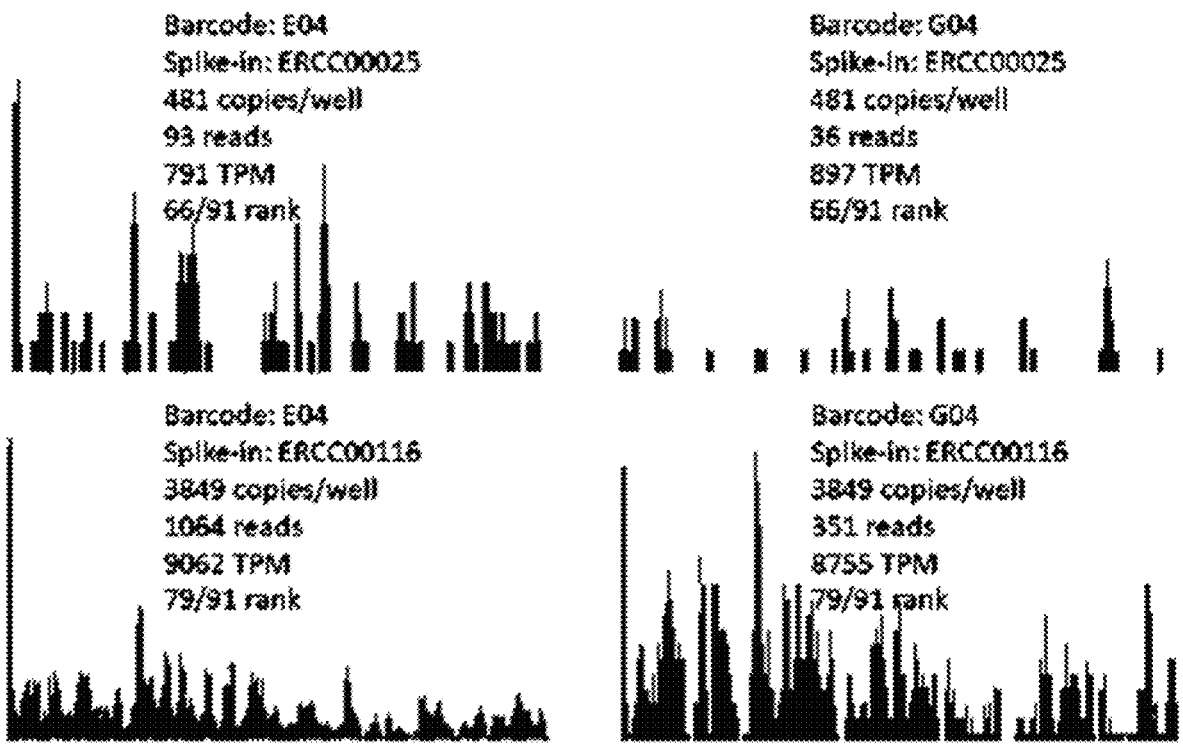
FIG. 29 shows diagrams illustrating results of experiments showing an example coverage on-device demonstrated on ERCC spike-in molecules.

Uniform coverage on-device is demonstrated on ERCC spike-in molecules (FIG. 29). Detection of two spiked-in transcripts of different abundance (ERCC00025 and ERCC00116) were analyzed for two different barcodes (E04 and G04). These plots show reads coverage of the transcripts and illustrate full-length transcript coverage of the method.

In summary, provided herein is a device for allowing compartmentalized reactions with minimized cross-contamination between the compartments, utilizing a delivery of material by loading wells to pooling wells, such that the pooling wells can be additively provided with reactants while maintaining isolation between the pooling wells. The use of geometric properties in devices of the disclosure is used to facilitate transmission of fluids/droplets without the need for hydrophilic surfaces.

The examples set forth above are provided to give those of ordinary skill in the art a complete disclosure and description of how to make and use the embodiments of the materials, compositions, systems and methods of the disclosure, and are not intended to limit the scope of what the inventors regard as their disclosure. Those skilled in the art will recognize how to adapt the features of the exemplified methods and systems according to various embodiments and scope of the claims.

All patents and publications mentioned in the specification are indicative of the levels of skill of those skilled in the art to which the disclosure pertains.

The entire disclosure of each document cited (including webpages patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence. Further, the computer readable form of the sequence listing of the ASCII text file P2301-US-Seq-List-ST25 is incorporated herein by reference in its entirety.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a." "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure.

Whenever a range is given in the specification, for example, a temperature range, a frequency range, a time range, or a composition range, all intermediate ranges and all subranges, as well as, all individual values included the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations, which is not specifically disclosed herein.

"Optional" or "optionally" means that the subsequently described circumstance may or may not occur, so that the description includes instances where the circumstance occurs and instances where it does not according to the guidance provided in the present disclosure. For example, the phrase "optionally substituted" means that a non-hydrogen substituent may or may not be present on a given atom, and, thus, the description includes structures wherein a non-hydrogen substituent is present and structures wherein a non-hydrogen substituent is not present. It will be appreciated that the phrase "optionally substituted" is used interchangeably with the phrase "substituted or unsubstituted." Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned can be identified in view of the desired features of the compound in view of the present disclosure, and in view of the features that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

REFERENCES

1. Evan Z. Macosko, A. Basu, R. Satija, J. Nemesh, K. Shekhar, M. Goldman, I. Tirosh, Allison R. Bialas, N. Kamitaki, Emily M. Martersteck, John J. Trombetta, David A. Weitz, Joshua R. Sanes, Alex K. Shalek, A. Regev and Steven A. McCarroll, *Cell,* 2015, 161, 1202-1214.
2. J. Nilsson, M. Evander, B. Hammarström and T. Laurell, *Analytica Chimica Acta,* 2009, 649, 141-157.
3. R. R. Pompano, C. E. Platt, M. A. Karymov and R. F. Ismagilov, *Langmuir,* 2012, 28, 1931-1941.
4. P. Abbyad, R. Dangla, A. Alexandrou and C. N. Baroud, *Lab on a Chip,* 2011, 11, 813-821.
5. R. Dangla, S. Lee and C. N. Baroud, Physical review letters, 2011, 107, 124501.
6. Y. Kang, M. H. Norris, J. Zarzycki-Siek, W. C. Nierman, S. P. Donachie and T. T. Hoang, *Genome research,* 2011.
7. J. H. Strauss, R. B. Kelly and R. L. Sinsheimer, *Biopolymers,* 1968, 6, 793-807.
8. A. A. Shishkin, G. Giannoukos, A. Kucukural, D. Ciulla, M. Busby, C. Surka, J. Chen, R. P. Bhattacharyya, R. F. Rudy and M. M. Patel, *Nature methods,* 2015, 12, 323.

The invention claimed is:

1. A device comprising:
a first plate comprising a first surface; and
a second plate with a second surface, the first surface in contact with the second surface, both the first surface and the second surface being hydrophobic;
the first plate having on the first surface that comprises:
a loading channel that includes respective vias at an inlet end and an outlet end of the loading channel, and a serpentine structure in a region of the outlet end;
a plurality of rows of alignment wells; and
pooling wells; and
the second plate having on the second surface that comprises:
channel-loaded loading wells having a greater depth than the loading channel;
an elution channel; and
a row of alignment protuberances aligned to fit in corresponding alignment wells of each of the plurality of rows of alignment wells of the first plate to provide relative positioning of the first and second plates according to a plurality of positions;
wherein:
the loading channel is defined by a single continuous opening having: a length that is greater than a length representing an entire extension of the channel-loaded loading wells, and a width that is substantially equal to a width of each of the channel-loaded loading wells,
the elution channel is defined by a single continuous opening having: a length that is greater than a length representing an entire extension of the pooling wells, and a width that is substantially equal to a width of each of the pooling wells,
the channel-loaded loading wells are configured be aligned in a one-to-one correspondence with the pooling wells when the first plate and the second plate are in a first position with respect to each other and are configured to be aligned with the loading channel such that reagents in the loading channel can access the channel-loaded loading wells when the first plate and the second plate are in a second position with respect to each other,
the pooling wells are configured to gather, in the first position, from the channel-loaded loading wells, reagents for reactions compartmentalized inside the pooling wells, by having i) a greater depth than the channel-loaded loading wells and ii) a greater longitudinal extension than the channel-loaded loading wells to accommodate multiple reagents transferred in additive fashion, in the first position, through dropping, by the channel-loaded loading wells, and
the greater depth of the pooling wells is dimensioned such that, in the first position, the reagents from the channel-loaded loading wells are transferred from the channel-loaded loading wells and deposited into the pooling wells by a capillary action through a surface tension driving force between the channel-loaded loading wells and the pooling wells in absence of hydrophilic surfaces.

2. The device of claim 1, wherein depth of the pooling wells is at least two times greater than depth of the channel-loaded loading wells.

3. The device of claim 2, wherein the depth of the pooling wells is at least three times greater than the depth of the channel-loaded loading wells.

4. A microfluidic slipchip comprising:
a first plate comprising a first surface; and
a second plate with a second surface, the first surface in slidable contact with the second surface for sliding according to a first direction;
the first plate comprising:
a loading channel having a single substantially rectangular continuous opening at the first surface with a loading channel length according to a second direction that is orthogonal to the first direction; and
a plurality of pooling wells of a same geometry arranged in-line according to the second direction and extending over a pooling wells length, each of the pooling wells having a circular opening at the first surface; and
the second plate comprising:
a plurality of channel-loaded loading wells of a same geometry arranged in-line according to the second direction and extending over a channel-loaded loading wells length, each of the channel-loaded loading wells having a circular opening at the second surface; and
an elution channel having a substantially rectangular opening at the second surface with an elution channel length according to the second direction that is substantially equal to the loading channel length;
wherein:
the loading channel includes respective vias at an inlet end and an outlet end of the loading channel, the respective via configured for pumping of a fluid through the loading channel,
the loading channel length is greater than the channel-loaded loading wells length,
the elution channel length is greater than the pooling wells length,
each circular opening at the first surface has a center that is aligned in the second direction with a center of a corresponding circular opening at the second surface,
a width of the circular opening at the first surface is substantially greater than a width of the circular opening at the second surface,
a width of the rectangular opening at the second surface is substantially greater than a width of the rectangular opening at the first surface,
the width of the rectangular opening at the first surface is substantially equal to the width of the circular opening at the second surface,
a depth of the pooling wells is at least twice a depth of the channel-loaded loading wells, and
the depth of the channel-loaded loading wells is greater than a depth of the loading channel.

5. The microfluidic slipchip of claim 4, wherein:
the first plate further comprises three rows of alignment wells arranged according to the second direction and distanced from one another according to the first direction,
the second plate further comprises one row of alignment protuberances arranged according to the second direction to fit in corresponding alignment wells of each of the three rows of alignment wells of the first plate to provide relative positioning of the first and second plates according to a plurality of positions according to the first direction, comprising:

a first position for alignment of the plurality of channel-loaded loading wells with the loading channel;

a second position for alignment of the plurality of channel-loaded loading wells with the plurality of pooling wells; and a third position for alignment of the plurality of pooling wells with the elution channel.

6. The device of claim 1, further comprising a PDMS oil carrier fluid.

7. The device of claim 1, wherein the plurality of rows of alignment wells are three rows of alignment wells positioned to correspond to i) loading well to loading channel, ii) loading well to pooling well, and iii) pooling well to elution channel.

8. The device of claim 1, wherein the pooling wells are pre-spotted with dehydrated adapters.

9. The device of claim 1, wherein the elution channel is configured to allow removal of material from the pooling wells through the elution channel when the first plate and the second plate are in a third position with respect to each other.

10. The device of claim 1, wherein the channel-loaded loading wells each have a side opposite a direction from the loading channel to the pooling wells the direction perpendicular to the loading channel, the side comprising two walls at equal angles from a bisector of the each channel-loaded loading wells parallel to the direction from the loading channel to the pooling wells, the equal angles each being less than 90 degrees.

* * * * *

SEQUENCE LISTING

```
<160> NUMBER OF SEQ ID NOS: 4

<210> SEQ ID NO 1
<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 1
caagcagaag acggcatacg agatcctggt aggtgactgg agttcagacg tgtgctcttc     60
cgatct                                                                66

<210> SEQ ID NO 2
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 2
aatgatacgg cgaccaccga gatctacact ctttccctac acgacgctct tccgatct       58

<210> SEQ ID NO 3
<211> LENGTH: 58
<212> TYPE: RNA
<213> ORGANISM: Artificial Sequence
<220> FEATURE:
<223> OTHER INFORMATION: Synthetic polynucleotide

<400> SEQUENCE: 3
rarururgrc rururargra rurcrgrgra rargrargrc rgrurcrgru rgrurarg       58

<210> SEQ ID NO 4
<211> LENGTH: 58
<212> TYPE: RNA
<213> ORGANISM: Artificial Sequence
<220> FEATURE:
<223> OTHER INFORMATION: Synthetic polynucleotide

<400> SEQUENCE: 4
rarurgrara rururargra rurcrgrgra rargrargrc rgrurcrgru rgrurarg       58
```